(12) United States Patent
Gibson et al.

(10) Patent No.: US 6,479,516 B1
(45) Date of Patent: Nov. 12, 2002

(54) 4-ARYLPIPERIDINE DERIVATIVES FOR THE TREATMENT OF PRURITUS

(75) Inventors: Stephen Paul Gibson; Ivan Tommasini, both of Sandwich (GB); Brian Scott Bronk, Gales Ferry, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/577,081

(22) Filed: May 23, 2000

(30) Foreign Application Priority Data

May 28, 1999 (GB) .............................. 9912410

(51) Int. Cl.[7] ..................... C07D 211/12; A61K 31/445
(52) U.S. Cl. ........................ 514/317; 546/192; 546/216
(58) Field of Search ................................ 546/192, 216; 514/317

(56) References Cited

U.S. PATENT DOCUMENTS

| | | | |
|---|---|---|---|
| 4,081,450 A | 3/1978 | Zimmerman | 546/185 |
| 4,191,771 A | 3/1980 | Zimmerman | 514/317 |
| 4,977,166 A | 12/1990 | Hardy et al. | 514/323 |
| 5,136,040 A | 8/1992 | Werner | 546/218 |
| 5,459,151 A | 10/1995 | Lombardo | 514/318 |
| 5,495,022 A | 2/1996 | Baumgarth et al. | 546/165 |
| 5,498,718 A | 3/1996 | Werner | 546/348 |

FOREIGN PATENT DOCUMENTS

| | | |
|---|---|---|
| DE | 4341403 | 6/1995 |
| EP | 0013078 | 7/1980 |
| EP | 0136863 | 4/1985 |
| EP | 0506468 A1 | 9/1992 |
| EP | 0506478 A1 | 9/1992 |
| EP | 0287339 | 8/1994 |
| EP | 0506468 B1 | 4/1995 |
| EP | 0657428 | 6/1995 |
| EP | 0506478 B1 | 9/1997 |
| EP | 09638898 | 9/1999 |
| GB | 1525584 | 9/1978 |
| GB | 2038812 | 11/1979 |
| WO | 9515327 | 6/1995 |
| WO | 9710207 | 3/1997 |
| WO | 9959971 | 11/1999 |
| WO | 0039089 | 7/2000 |

OTHER PUBLICATIONS

Gessner, et al.; Synthesis and Dihydropteridine Reductase Inhibitory Effects of Potential Metabolites of the Neurotoxin 1–Methyl–4–phenyl–1,2,3,6–tetrahydropyridine; Journal of Medicinal Chemistry; (1985) vol. 28, No. 3, pp 311–317—XP–002153365.

P. Mittra, et al.; Synthesis and Fungitoxicity of Some Bicyclic Compounds; J. Indian Chem.; Soc. 58(9), (1981) pp 921.

Mitch, et al.; 3,4–Dimethyl–4– (3–hydroxyphenyl)piperidines: Opioid Antagonists with Potent Anorectant Activity; J. Med. Chem. (1993) 2842–2850.

Zimmerman; Structure–Activity Relationship of trans–3, 4–dimethyl–4–(3–hydroxypheyl)piperidine Antagonists for $\mu$–and $\kappa$–Opioid Receptors; J. Med. Chem. (1993) 283–2850.

*Primary Examiner*—Zinna Northington Davis
(74) *Attorney, Agent, or Firm*—Peter C. Richardson; Paul H. Ginsburg; Kristina L. Konstas

(57) ABSTRACT

There is provided a compound of formula I,

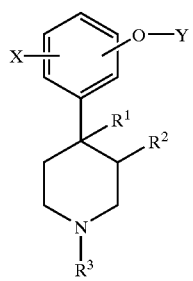

wherein $R^1$, $R^2$, $R^3$, X and Y have meanings given in the description, which are useful in the prophylaxis and in the treatment of pruritus.

34 Claims, No Drawings

4-ARYLPIPERIDINE DERIVATIVES FOR THE TREATMENT OF PRURITUS

PRIORITY APPLICATION

The present application is claiming priority of Great Britian Application Serial No. GB 9912410.9, filed May 28, 1999.

FIELD OF THE INVENTION

This invention relates to novel 4-phenylpiperidines having utility in the treatment of pruritic dermatoses including allergic dermatitis and atopy in animals and humans, and processes for the preparation of and intermediates used in the preparation of such compounds.

BACKGROUND OF THE INVENTION

Itching or pruritus is a common dermatological symptom which can give rise to considerable distress, in both humans and animals. Pruritus is often associated with inflammatory skin disease which can commonly be caused by hypersensitivity reactions, such as reaction to insect bites e.g. flea bites, or to environmental allergens such as house dust mite or pollen; or by bacterial and fungal infections of the skin or ectoparasite infections. Previous treatments for pruritus include the use of corticosteroids and antihistamines, however both have undesired side effects. Other therapies include the use of essential fatty acid dietary supplements which are slow to act and offer only limited efficacy against allergic dermatitis. A variety of emollients such as soft paraffin, glycerine and lanolin are also employed but with limited success and there is a continuing need for an effective remedy.

Certain 1,3,4-trisubstituted 4-aryl-piperidine derivatives are disclosed in GB-A-1525584 as potent narcotic antagonists which also display analgesic properties. These compounds are also claimed in EP-B-0287339 as opioid antagonists which block the effect of agonists at the mu or kappa receptors having potential utility in treating a variety of disorders associated with these receptors such as eating disorders, opiate overdose, depression, smoking, alcoholism, sexual dysfunction, shock, stroke, spinal damage and head trauma; utility as an appetite suppressant for weight loss has also been suggested. Further related 1-N-substituted-4-aryl piperidines are disclosed in EP-A-0506468 and EP-A-0506478. Potential utility is suggested in preventing peripherally mediated undesired opiate effects and in relieving the symptoms of idiopathic constipation and irritable bowel syndrome.

According to the present invention we provide novel 4-phenylpiperidines which are, and/or are prodrugs of, potent and effective antipruritic agents.

SUMMARY OF THE INVENTION

Thus, the present invention provides compounds of formula I:

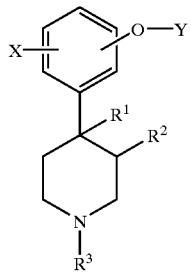

wherein
  $R^1$ and $R^2$ are each independently H or $C_{1-4}$ alkyl;
  $R^3$ represents aryl (optionally substituted by one or more substituents selected from OH, nitro, halo, CN, $CH_2CN$, $CONH_2$, $C_{,1-4}$ alkyl, $C_{1-4}$ alkoxy, $C_{1-5}$ alkanoyl (which latter three groups are optionally substituted by one or more halo atoms) and $—N(R^{4a})(R^{4b}))$, $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{5c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $—W—A^1—N(R^{5b})(R^{5c})$;
  n is 0, 1 or 2;
  W represents a single bond, C(O) or $S(O)_p$;
  $A^1$ represents a single bond or $C_{1-10}$ alkylene;
  provided that when both W and $A^1$ represent single bonds, then the group $—N(R^{5b})(R^{5c})$ is not directly attached to an unsaturated carbon atom;
  p is 0, 1 or 2;
  $R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;
  provided that $R^{4d}$ does not represent H when n represents 1 or 2;
  $R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $Het^3$, or $R^{5b}$ and $R^{5c}$ together represent unbranched $C_{2-6}$ alkylene which alkylene group is optionally interrupted by O, S and/or an $N(R^7)$ group and is optionally substituted by one or more $C_{1-4}$ alkyl groups;
  $R^6$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;

$R^7$ represents H, $C_{1-6}$ alkyl, $C_{3-8}$ cycloalkyl, $A^2$—($C_{3-8}$ cycloalkyl) or $A^2$-aryl;

$A^2$ represents $C_1$ alkylene;

$Het^1$, $Het^2$ and $Het^3$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents —C(=E)NR$^8$R$^9$, C(O)R$^{10}$, C(O)OR$^{10}$, C(O)CH(R$^{10a}$)N(G)G$^a$, R$^{11}$, CH(R$^{12b}$)C(O)OR$^{12a}$, CH(R$^{12b}$)OCO$_2$R$^{12a}$, C(O)C(R$^{13a}$)=C(R$^{13b}$)NH$_2$, C(O)CH(R$^{13a}$)CH(NH$_2$)(R$^{13b}$) or PO(OR$^{14}$)$_2$;

E represents O or S;

$R^8$ and $R^9$ independently represents H, $C_{1-10}$ alkyl, $C_{3-10}$ alkenyl (which latter two groups are optionally substituted by one or more aryl or $C_{4-7}$ cycloalkyl groups (which two groups are optionally substituted by one or more selected from halo, $C_{1-4}$ alkyl, $C_{1-4}$ alkoxy, $C_{1-4}$ haloalkyl or $C_{1-4}$ haloalkoxy)), aryl, $C_{4-7}$ cycloalkyl (optionally substituted by one or more substituents selected from halo, $C_{1-4}$ alkyl and $C_{1-4}$ alkoxy (which latter two groups are optionally substituted by one or more halo atoms)), or $R^8$ and $R^9$, together with the N-atom to which both are attached, represent Het$^4$;

Het$^4$ represents a 5- to 8-membered heterocyclic ring comprising at least one nitrogen atom and optionally one or more additional heteroatoms selected from oxygen and sulfur, which heterocyclic ring is optionally substituted by one or more $C_{1-4}$ alkyl groups;

$R^{10}$ represents H, Het$^5$, $C_{4-7}$ cycloalkyl (optionally substituted by one or more $C_{1-4}$ alkyl groups), $C_{1-11}$ alkyl (optionally substituted by one or more substituents selected from aryl (optionally substituted by one or more substituents selected from OH, halo, $C_{1-4}$ alkanoyl, $C_{1-4}$ alkanoyloxy, N(R$^8$)(R$^9$), C(O)N(R$^8$)(R), $C_{1-4}$ alkyl, $C_{1-4}$ alkoxy, $C_{1-4}$ haloalkyl and $C_{1-4}$ haloalkoxy) or $C_{4-7}$ cycloalkyl (which latter group is optionally substituted by one or more $C_{1-4}$ alkyl groups)) or aryl (optionally substituted by one or more substituents selected from OH, halo, $C_{1-4}$ alkanoyl, $C_{1-4}$ alkanoyloxy, N(R$^8$)(R$^9$), C(O)N(R$^8$)($^9$), $C_{1-4}$ alkyl and $C_{1-4}$ alkoxy (which latter two groups are optionally substituted by one or more halo atoms));

$R^{10a}$ represents H, $C_{4-7}$ cycloalkyl, $C_{1-10}$ alkyl (optionally substituted by one or more substituents selected from aryl or $C_{4-7}$ cycloalkyl), aryl, or $R^{10a}$ (optionally in conjunction with G$^a$) represents a naturally occurring amino acid substituent;

G and G$^a$ independently represent H, an amino protective group, or G$^a$, together with R$^{10a}$, represents a naturally occurring amino acid substituent;

$R^{11}$ represents H, $C_{4-7}$ cycloalkyl (optionally substituted by one or more $C_{1-4}$ alkyl groups), aryl (optionally substituted by one or more substituents selected from OH, halo, $C_{1-4}$ alkanoyl, $C_{1-4}$ alkanoyloxy, N(R$^8$)(R$^9$), C(O)N(R$^8$)(R$^9$), $C_{1-4}$ alkyl and $C_{1-4}$ alkoxy (which latter two groups are optionally substituted by one or more halo atoms)), $C_{1-10}$ alkyl, $C_{3-10}$ alkenyl, which alkyl or alkenyl group is optionally substituted by one or more substituents selected from C(O)NH$_2$, Het$^6$, $C_{4-7}$ cycloalkyl (optionally substituted by one or more $C_{1-4}$ alkyl groups), aryl, aryloxy or aryl($C_{1-4}$)alkoxy (which latter three groups are optionally substituted by one or more substituents selected from OH, halo, $C_{1-4}$ alkanoyl, $C_{1-4}$ alkanoyloxy, N(R$^8$)(R$^9$), C(O)N(R$^8$)(R$^9$), $C_{1-4}$ alkyl and $C_{1-4}$ alkoxy (which latter two groups are optionally substituted by one or more halo atoms)) or $R^{11}$ represents Het$^7$;

Het$^5$ to Het$^7$ independently represent 4- to 6-membered heterocyclic rings, which rings contain at least one heteroatom selected from oxygen, sulfur, and/or nitrogen, which rings are optionally fused to a benzene ring, and which rings are optionally substituted in the heterocyclic and/or fused benzene ring part by one or more substituents selected from OH, =O, nitro, amino, halo, CN, aryl, $C_{1-4}$ alkyl, $C_{1-4}$ alkoxy, $C_{3-6}$ cycloalkyl and $C_{1-5}$ alkanoyl (which latter four groups are optionally substituted by one or more halo atoms);

$R^{12a}$ and $R^{12b}$ independently represent H, $C_{4-7}$ cycloalkyl (optionally substituted by one or more $C_{1-4}$ alkyl groups), $C_{1-10}$ alkyl (optionally substituted by one or more substituents selected from aryl or $C_{4-7}$ cycloalkyl (which latter group is optionally substituted by one or more $C_{1-4}$ alkyl groups)) or aryl (optionally substituted by one or more substituents selected from OH, halo, $C_{1-4}$ alkanoyl, $C_{1-4}$ alkanoyloxy, $C_{1-4}$ alkyl and $C_{1-4}$ alkoxy (which latter two groups are optionally substituted by one or more halo atoms));

$R^{13a}$ and $R^{13b}$ independently represent H, $C_{4-7}$ cycloalkyl (optionally substituted by one or more $C_{1-4}$ alkyl groups), $C_{1-10}$ alkyl, $C_{2-10}$ alkenyl (which alkyl and alkenyl groups are optionally substituted by one or more substituents selected from aryl or $C_{4-7}$ cycloalkyl (which latter group is optionally substituted by one or more $C_{1-4}$ alkyl groups)), or aryl (optionally substituted by one or more substituents selected from OH, halo, $C_{1-4}$ alkanoyl, $C_{1-4}$ alkanoyloxy, $C_{1-4}$ alkyl and $C_{1-4}$ alkoxy (which latter two groups are optionally substituted by one or more halo atoms));

$R^{14}$ represents H, $C_{4-7}$ cycloalkyl (optionally substituted by one or more $C_{1-4}$ alkyl groups), $C_{1-10}$ alkyl (optionally substituted by one or more substituents selected from aryl or $C_{4-7}$ cycloalkyl (which latter group is optionally substituted by one or more $C_{1-4}$ alkyl groups)), or aryl (optionally substituted by one or more substituents selected from OH, halo, $C_{1-4}$ alkanoyl, $C_{1-4}$ alkanoyloxy, $C_{1-4}$ alkyl and $C_{1-4}$ alkoxy (which latter two groups are optionally substituted by one or more halo atoms));

X represents one or more substituents on the benzene ring, which substituents are independently selected from halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy or N(R$^{15a}$)(R$^{15b}$)), C(O)R$^{16a}$, C(O)OR$^{16b}$, OC(O)R$^{16c}$, S(O)$_r$OR$^{16d}$, S(O)$_r$R$^{17a}$, OR$^{16e}$, N(R$^{18a}$)(R$^{18b}$), C(O)N(R$^{18c}$)(R$^{18d}$), OC(O)N(R$^{18e}$)(R$^{18f}$), N(R$^{18g}$)C(O)R$^{16f}$, N(R$^{18h}$)C(O)OR$^{19}$, N(R$^{18i}$)C(O)N(R$^{18j}$)(R$^{18k}$), N(R$^{18m}$)S(O)$_2$R$^{17b}$ or B(OR$^{15c}$)$_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from halo, nitro, OH, $C_{1-4}$ alkyl or $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from halo, nitro, OH, $C_{1-4}$ alkyl or $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from halo, nitro, OH, $C_{1-4}$ alkyl or $C_{1-4}$ alkoxy), $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from halo, nitro, OH, $C_{1-4}$ alkyl or $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from oxygen, sulfur and/or nitrogen, and which rings are optionally substituted by one or more substituents selected from OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms); or pharmaceutically, or veterinarily, acceptable derivatives thereof; which compounds are referred to together hereinafter as "the compounds of the invention".

DETAILED DESCRIPTION OF THE INVENTION

In the definitions used herein, alkyl, alkylene, alkoxy, alkoxy carbonyl, alkanoyl, alkanoyloxy, alkenyl, alkynyl and the alkyl parts of alkylphenyl and aryl alkoxy groups may, when there is a sufficient number of carbon atoms, be straight or branched-chain and/or optionally interrupted by one or more oxygen and/or sulfur atom(s). The term halo includes fluoro, chloro, bromo or iodo. The term "aryl" includes optionally substituted phenyl, naphthyl and the like, and "aryloxy" includes optionally substituted phenoxy and naphthyloxy and the like. Unless otherwise specified, aryl and aryloxy groups are optionally substituted by one or more (e.g. one to three) substituents selected from OH, nitro, amino, halo, CN, $CH_2CN$, $CONH_2$, $C_{1-4}$ alkyl, $C_{1-4}$ alkoxy $C_{1-4}$ alkoxy carbonyl and $C_{1-5}$ alkanoyl (which latter four groups are optionally substituted by one or more halo atoms).

The heterocyclic rings that $Het^1$, $Het^2$, $Het^3$, $Het^4$, $Het^5$, $Het^6$, $Het^7$, $Het^8$, $Het^9$, $Het^{10}$ and $Het^{11}$ represent may be fully saturated, partially unsaturated and/or wholly or partially aromatic in character. Specific rings that may be mentioned include: for $Het^5$, pyridine or pyridine-N-oxide.

For the avoidance of doubt, when Het ($Het^1$, $Het^2$, $Het^3$, $Het^4$, $Het^5$, $Het^6$, $Het^7$, $Het^8$, $Het^9$, $Het^{10}$ and $Het^{11}$) groups are at least part-saturated, possible points of substitution include the atom (e.g. the carbon atom) at the point of attachment of the Het group to the rest of the molecule. Het groups may also be attached to the rest of the molecule via a heteroatom.

The piperidine moiety in compounds of formula I may be in N-oxidised form. Sulfur atoms that may interrupt (e.g. alkyl) substituents in compounds of formula I may be present in oxidised form (e.g. as sulfoxides or sulfones). All $Het^1$, $Het^2$, $Het^3$, $Het^4$, $Het^5$, $Het^6$, $Het^7$, $Het^8$, $Het^9$, $Het^{10}$ and $Het^{11}$ groups may also be in N- or S-oxidized forms.

The term "amino protective group" as used herein will be understood by the skilled person to include those mentioned in "Protective Groups in Organic Synthesis", $2^{nd}$ edition, TW Greene & PGM Wutz, Wiley-Interscience (1991), in particular those indexed at pages 218 to 222 of that reference, the disclosure in which document is hereby incorporated by reference.

Specific examples of amino protective groups thus include carbamate groups (e.g. methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-trimethylsilylethyl, 2-methylthioethyl, 2-methylsulfonylethyl, 2(p-toluenesulfonyl)ethyl, 2-phosphonioethyl, 1,1-dimethylpropynyl, 1,1-dimethyl-3-(N,N-dimethylcarboxamido)propyl, 1,1-dimethyl-3-(N,N-diethylamino)propyl, 1-methyl-1-(1-adamantyl)ethyl, 1-methyl-1-phenylethyl, 1-methyl-1-(3,5-dimethoxyphenyl) ethyl, 1-methyl-1-(4-biphenylyl)ethyl, 1-methyl-1-(p-phenylazophenyl)ethyl, 1,1-dimethyl-2-haloethyl, 1,1-dimethyl-2,2,2-trichloroethyl, 1,1-dimethyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4,6-tri-t-butylphenyl, m-nitrophenyl, S-phenyl, 8-quinolinyl, N-hydroxypiperidinyl, 4-(1,4-dimnethylpiperidinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitrobenzyl, o-nitrobenzyl, 3,4-dimethoxy-6-nitrobenzyl, p-bromobenzyl, chlorobenzyl, 2,4-dichloro-benzyl, p-cyanobenzyl, o-(N,N-dimethylcarboxamidobenzyl) benzyl, m-chloro-p-acyloxybenzyl, p-(dihydroxyboryl) benzyl, p-(phenylazo)-benzyl, p-(p'-methoxyphenylazo) benzyl, 5-benzisoxazolyl-methyl, 9-anthrylmethyl, diphenylmethyl, phenyl(o-nitrophenyl)methyl, di(2-pyridyl) methyl, 1-methyl-1-(4-pyridyl)ethyl, isonicotinyl or S-benzyl carbamate groups), amide groups (e.g. N-formyl, N-acetyl, N-chloro-acetyl, N-dichloroacetyl, N-trichloroacetyl, N-trifluoroacetyl, N-o-nitrophenylacetyl, N-o-nitrophenoxyacetyl, N-acetoacetyl, N-acetyl-pyridinium, N-3-phenylpropionyl, N-3-(p-hydroxyphenyl) propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-isobutyryl, N-o-nitrocinnamoyl, N-picolinoyl, N-(N'-acetylmethionyl), N-(N'-benzoylphenylalanyl), N-benzoyl, N-p-phenylbenzoyl, N-p-methoxybenzoyl, N-o-nitrobenzoyl or N-o-(benzoyloxymethyl)benzoyl amide groups), alkyl groups (e.g. N-allyl, N-phenacyl, N-3-acetoxypropyl, N-(4-nitro-1-cyclohexyl-2-oxo-pyrrolin-3-yl), N-methoxymethyl, N-chloro-ethoxymethyl, N-benzyloxymethyl, N-pivaloyloxymethyl, N-2-tetrahydro-pyranyl, N-2,4-dinitrophenyl, N-benzyl, N-3,4-dimethoxybenzyl, N-o-nitrobenzyl, N-diep-methoxyphenyl) methyl, N-triphenylmethyl, N-p-methoxyphenyl) diphenylmethyl, N-diphenyl-4-pyridylmethyl, N-2-picolyl N'-oxide or N-dibenzosuberyl groups), phosphinyl and phosphoryl groups (e.g. N-diphenylphosphinyl, N-dimethylthiophosphinyl, N-diphenylthiophosphinyl, N-diethylphosphoryl, N-dibenzylphosphoryl or N-phenylphosphoryl groups), sulfenyl groups (e.g. N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl or N-triphenylmethylsulfenyl groups), sulfonyl groups (e.g. N-benzenesulfonyl, N-p-methoxybenzenesulfonyl, N-2,4,6-trimethylbenzenesulfonyl, N-toluenesulfonyl, N-benzylsulfonyl, N-p-methylbenzylsulfonyl, N-trifluoromethylsulfonyl or N-phenacylsulfonyl) or the N-trimethylsilyl group.

The term "naturally occurring amino acid" as used herein includes the amino acids glycine, alanine, valine, leucine, isoleucine, phenylalanine, tryptophan, tyrosine, histidine, serine, threonine, methionine, cysteine, aspartic acid, glutamic acid, asparagine, glutamine, lysine, arginine and proline.

The term "pharmaceutically, or veterinarily, acceptable derivatives" includes non-toxic salts. Salts which may be mentioned include: acid addition salts, for example, salts formed with sulfuric, hydrochloric, hydrobromic, phosphoric, hydroiodic, sulfamic, organo-sulfonic, citric, carboxylic (e.g. acetic, benzoic, etc.), maleic, malic, succinic, tartaric, cinnamic, ascorbic and related acids; base addition salts; salts formed with bases, for example, the sodium, potassium and $C_{1-4}$ alkyl ammonium salts.

The compounds of the invention may also be in the form of quaternary ammonium salts, e.g. at the piperdine moiety, which salts may be formed by reaction with a variety of alkylating agents, such as an alkyl halide or an ester of sulfuric, or an aromatic sulfonic acid.

The compounds of the invention may exhibit tautomerism. All tautomeric forms of the compounds of formula I are included within the scope of the invention.

The compounds of the invention contain one or more asymmetric centres and thus they can exist as enantiomers and diastereomers. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. The invention includes the use of both the separated individual isomers as well as mixtures of isomers.

Also included within the scope of the invention are radiolabelled derivatives of compounds of formula I which are suitable for biological studies.

According to a further aspect of the invention, there is provided a compound of formula I, as hereinbefore defined, provided that when Y is H or 2-methyl-2-propionamide, OY is attached to the benzene ring at the meta-position relative to the piperidine ring (which ring is not in N-oxidised form), and X is one or two substituents independently selected from halo, $C_{1-4}$ alkyl or $C_{1-4}$ alkoxy (which latter two groups are optionally substituted by one or more halo atoms, but are otherwise unsubstituted), then $R^3$ represents:

optionally substituted aryl;

optionally substituted $C_{3-10}$ alkenyl or $C_{3-10}$ alkynyl (which two groups are both interrupted by at least one oxygen and/or sulfur atoms);

$C_{2-10}$ alkyl, interrupted by at least two oxygen atoms and/or at least one sulfur atom;

$C_{1-10}$ alkyl, $C_{3-10}$ alkenyl or $C_{3-10}$ alkynyl, which groups are all optionally interrupted by one or more oxygen and/or sulfur atoms, and are substituted and/or terminated by one or more of:

$S(O)_nR^{4d}$, $N(R^{5a})S(O)_2R^6$, $Het^1$ (substituted by one or more substituents selected from nitro, amino and $C_{1-5}$ alkanoyl (which latter group is optionally substituted by one or more halo atoms)), aryl (substituted by one or more substituents selected from nitro, amino and $C_{1-5}$ haloalkanoyl) or adamantyl (which latter group is substituted by one or more of the relevant substituents identified hereinbefore); or $OR^{4c}$, in which $R^{4c}$ represents $C_{7-10}$ alkyl, $C_{3-10}$ alkenyl, $C_{3-10}$ alkynyl or $Het^2$ (which latter four groups are all optionally substituted by one or more of the relevant substituents identified hereinbefore), or $R^{4c}$ represents $C_{1-10}$ alkyl, $C_{1-4}$ alkylphenyl, $C_{3-8}$ cycloalkyl or aryl (which latter four groups are all substituted by one or more of the relevant substituents identified hereinbefore);

—W—$A^1$—N($R^{5b}$)($R^{5c}$), in which $R^{5b}$ and/or $R^{5c}$ independently represent $C_{1-4}$ alkylphenyl (which latter group is optionally substituted by one or more of the relevant substituents identified hereinbefore), $C_{1-10}$ alkyl, $C_{3-10}$ alkenyl, $C_{3-10}$ alkynyl, $C_{3-8}$ cycloalkyl (which latter four groups are all substituted by one or more of the relevant substituents identified hereinbefore), or aryl (substituted by one or more substituents selected from nitro, amino and $C_{1-5}$ haloalkanoyl);

which compounds may also be termed "compounds of the invention".

According to a further aspect of the invention, there is provided a compound of formula I, as hereinbefore defined, with the additional proviso that when OY represents O—$C_{1-4}$ alkyl, OY is attached to the benzene ring at the meta-position relative to the piperidine ring (which ring is not in N-oxidised form), and X is one or two substituents independently selected from halo, $C_{1-4}$ alkyl or $C_{1-4}$ alkoxy (which latter two groups are optionally substituted by one or more halo atoms, but are otherwise unsubstituted), then $R^3$ does not represent:

straight or branched-chain $C_{1-10}$ alkyl (optionally substituted by one or more substituents selected from unsubstituted aryl or unsubstituted $C_{3-8}$ cycloalkyl);

which compounds may also be termed "compounds of the invention".

Preferred compounds of the invention include those wherein:

The group OY is attached to the benzene ring in the position meta-relative to the piperidine group;

the substituent(s) X is/are attached to the benzene ring in position(s) that are ortho- and/or para-relative to the piperidine group;

$R^1$ represents $C_{1-2}$ alkyl;

$R^2$ represents H or $C_{1-2}$ alkyl;

$R^3$ represents $C_{1-8}$ alkyl, $C_{3-8}$ alkenyl or $C_{3-8}$ alkynyl wherein said alkyl, alkenyl or alkynyl groups are optionally substituted and/or terminated by one or more substituents selected from $C_{3-8}$ cycloalkyl, $OR^{4c}$, CN, $Het^1$ or aryl (which latter group is optionally substituted by one or more substituents selected from OH, $C_{1-2}$ alkyl, $C_{1-2}$ alkoxy or halo);

$R^{4c}$ represents H, $C_{1-6}$ alkyl, $C_{4-6}$ cycloalkyl, aryl or $Het^2$;

$Het^1$ and $Het^2$ independently represent 5- to 7-membered heterocyclic groups, which groups contain at least one heteroatom selected from oxygen, sulfur and/or nitrogen, and which groups are optionally substituted by one or more $C_{1-2}$ alkyl groups (which alkyl groups are optionally substituted by one or more halo atoms);

Y represents $C(=E)NR^8R^9$, $C(O)R^{10}$ or $R^{11}$;

$R^8$ and $R^9$ independently represent H or $C_{1-4}$ alkyl;

$R^{10}$ represents $C_{1-6}$ alkyl (substituted by one or more phenyl groups) or aryl (optionally substituted by one or more substituents selected from OH, halo, $C_{1-2}$ alkanoyloxy, $NH_2$, $C(O)NH_2$ and $C_{1-2}$ alkyl (which latter group is optionally substituted by one or more halo atoms));

$R^{11}$ represents H, $C_{1-10}$ alkyl or $C_{3-10}$ alkenyl, which latter two groups are optionally substituted by one or more substituents selected from $Het^6$ and phenyl;

$Het^6$ represents a 5- to 6-membered heterocyclic ring, which ring contains at least one heteroatom selected from oxygen, sulfur and/or nitrogen, which ring is optionally fused to a benzene ring, and which ring is optionally substituted in the heterocyclic and/or fused benzene ring part by one or more substituents selected from OH, =O and $C_{1-4}$ alkyl);

$Het^6$ is in S-oxidised form;

X represents one to three substituents selected from halo, nitro, $C_{2-6}$ alkenyl, $C_{1-6}$ alkyl (which alkyl group is optionally substituted and/or terminated by a substituent selected from OH, $C_{1-4}$ alkoxy or $N(R^{15a})(R^{15b})$, $C(O)R^{16a}$, $C(O)OR^{16b}$, $S(O)_{TR}{}^{17a}$, $N(R^{18a})(R^{18b})$, $C(O)N(R^{18c})(R^{18d})$, $N(R^{18g})C(O)R^{16f}$, $N(R^{18h})C(O)OR^{19}$, $N(R^{18i})C(O)N(R^{18j})(R^{18k})$ or $N(R^{18m})S(O)_2R^{17b}$;

$R^{15a}$ and $R^{15b}$ independently represent H or $C_{1-4}$ alkyl;

$R^{16a}$ to $R^{16f}$ independently represent H or $C_{1-6}$ alkyl (which latter group is optionally substituted by one or more halo atoms);

$R^{17a}$ and $R^{17b}$ independently represent $C_{1-4}$ alkyl (optionally substituted by one or more halo atoms) or $N(R^{20a})(R^{20b})$;

$R^{18a}$ to $R^{18m}$ independently represent H, $C_{1-6}$ alkyl, or $R^{18j}$ and $R^{18k}$ together represent unbranched $C_{3-6}$ alkylene optionally interrupted by oxygen;

$R^{19}$ represents $C_{1-4}$ alkyl;

$R^{20a}$ and $R^{20b}$ independently represent H or $C_{1-4}$ alkyl.

More preferred compounds of the invention include those wherein:

the substituent(s) X is/are attached to the benzene ring in the position(s) that are ortho- and/or para-relative to the OY group;

$R^1$ represents methyl;

$R^2$ represents H or methyl;

$R^3$ represents linear, saturated $C_{1-7}$ alky, which alkyl group is optionally substituted and/or terminated by one or more substituents selected from $C_{4-7}$ cycloalkyl, $OR^{4c}$, CN, $Het^1$ or phenyl (which latter group is optionally substituted by one or more $C_{1-2}$ alkyl groups);

$R^{4c}$ represents H, $C_{1-4}$ alkyl, $C_{4-6}$ cycloalkyl or phenyl;

$Het^1$ represents a 5- or 6-membered saturated heterocyclic group, which groups contains one heteroatom selected from oxygen, sulfur or nitrogen;

$R^8$ and $R^9$ independently represent $C_{1-2}$ alkyl;

$R^{10}$ represents $C_{1-6}$ alkyl;

$R^{11}$ represents H or $C_{1-5}$ alkyl;

X represents a substituent selected from nitro, $C_{2-4}$ alkenyl, $C_{1-2}$ alkyl (which alkyl group is optionally substituted and/or terminated by OH or $N(R^{15a})(R^{15b})$), $C(O)R^{16a}$, $C(O)OR^{16b}$, $S(O)_2R^{17a}$, $N(R^{18a})(R^{18b})$, $C(O)N(R^{18c})(R^{18d})$, $N(H)C(O)R^{16f}$, $N(H)C(O)OR^{19}$, $N(H)C(O)N(R^{18j})(R^{18k})$ or $N(H)S(O)_2R^{17b}$, or X represents one to three halo (e.g. F, Cl, and/or Br) atoms;

$R^{15a}$ and $R^{15b}$ independently represent H or $C_{1-3}$ alkyl;

$R^{16a}$ to $R^{16f}$ independently represent H or $C_{1-5}$ alkyl (which latter group is optionally substituted by one or more halo atoms);

$R^{17a}$ and $R^{17b}$ independently represent $C_{1-2}$ alkyl (optionally substituted by one or more halo atoms) or $N(R^{20a})(R^{20b})$;

$R^{18a}$ to $R^{18k}$ independently represent H or $C_{1-5}$ alkyl;

$R^{20a}$ and $R^{20b}$ independently represent H or $C_{1-2}$ alkyl.

Particularly preferred compounds of the invention include those wherein:

$R^1$ and $R^2$ represent methyl groups in the mutually trans configuration;

Y represents H;

$R^3$ represents linear, saturated $C_{1-6}$ alkyl, which alkyl group is optionally substituted and/or terminated by one or more $C_{4-7}$ cycloalkyl groups;

X represents fluoro or N(H)C(O)Et in the position ortho-relative to the OY group.

Preferred compounds of the invention include the compounds of the Examples described hereinafter.

Thus, according to a further aspect of the invention, there is provided a compound of formula I which, irrespective of any of the foregoing definitions, is:

(±)-N-hexyl-trans-3,4-dimethyl-4-(4-bromo-3-hydroxyphenyl)piperidine;

(±)-N-hexyl-trans-3,4-dimethyl-4-(3-hydroxy-4-nitrophenyl)piperidine;

(±)-N-hexyl-trans-3,4-dimethyl-4-(2,4-dibromo-3-hydroxyphenyl)piperidine;

(±)-N-hexyl-trans-3,4-dimethyl-4-(4-amino-3-hydroxyphenyl)piperidine;

(±)-N-hexyl-trans-3,4-dimethyl-4-[3-hydroxy-4-(2-methyl-butanoyl)-phenyl]piperidine;

(±)-N-hexyl-trans-3,4-dimethyl-4-(4-allyl-3-hydroxyphenyl)piperidine;

(±)-N-hexyl-trans-3,4-dimethyl-4-(3-hydroxy-4-methylphenyl)piperidine;

(±)-N-hexyl-trans-3,4-dimethyl-4-(4-acetylamino-3-hydroxyphenyl)piperidine;

(±)-N-hexyl-trans-3,4-dimethyl-4-(3-hydroxy-4-hydroxymethylphenyl)piperidine;

(±)-N-hexyl-trans-3,4-dimethyl-4-(3-hydroxy-4-trifluoromethanesulfonyl-aminophenyl)piperidine;

(±)-N-hexyl-trans-3,4-dimethyl-4-(4-ethyl-3-hydroxyphenyl)piperidine;

(±)-N-hexyl-trans-3,4-dimethyl-4-[4-(2,2-dimethylpropanoylamino)-3-hydroxyphenyl]piperidine;

(±)-N-hexyl-trans-3,4-dimethyl-4-(3-hydroxy-4-methylaminomethyl-phenyl)piperidine;

(±)-N-hexyl-trans-3,4-dimethyl-4-(4-ethylaminomethyl-3-hydroxy-phenyl)piperidine;

(±)-N-hexyl-trans-3,4-dimethyl-4-(4-dimethylaminomethyl-3-hydroxy-phenyl)piperidine;
(±)-N-hexyl-trans-3,4-dimethyl-4-(3-hydroxy-2-methylphenyl)piperidine;
(±)-N-hexyl-trans-3,4-dimethyl-4-(3-hydroxy-4-methoxycarbonylphenyl)piperidine;
(±)-N-hexyl-trans-3,4-dimethyl-4-(4-ethoxycarbonyl-3-hydroxyphenyl)piperidine;
(±)-N-hexyl-trans-3,4-dimethyl-4-(4-N'-methylaminocarbonyl-3-hydroxyphenyl)piperidine;
(±)-N-hexyl-trans-3,4-dimethyl-4-(4-N',N'-dimethylaminocarbonyl-3-hydroxyphenyl)piperidine;
(±)-N-hexyl-trans-3,4-dimethyl-4-(4-N',N'-diethylaminocarbonyl-3-hydroxyphenyl)piperidine;
(±)-N-hexyl-trans-3,4-dimethyl-4-(3-hydroxy-4-propionylaminophenyl)piperidine;
(±)-N-hexyl-trans-3,4-dimethyl-4-(4-N',N'-dimethylaminocarbonylamino-3-hydroxyphenyl)piperidine;
(±)-N-hexyl-trans-3,4-dimethyl-4-(3-hydroxy-4-N'-methylaminocarbonylaminophenyl)piperidine;
(±)-N-hexyl-trans-3,4-dimethyl-4-(3-hydroxy-4-methoxycarbonylaminophenyl)piperidine;
(±)-N-hexyl-trans-3,4-dimethyl-4-(4-formylamino-3-aminophenyl)piperidine;
(±)-N-hexyl-trans-3,4-dimethyl-4-(4-N',N'-dimethylaminosulfonylamino-3-hydroxyphenyl)piperidine;
(±)-N-hexyl-trans-3,4-dimethyl-4-(3-hydroxy-4-pentanoylaminophenyl)piperidine;
(±)-N-hexyl-trans-3,4-dimethyl-4-(2,4-dichloro-3-hydroxyphenyl)piperidine;
(±)-N-hexyl-trans-3,4-dimethyl-4-[3-hydroxy-4-(2-methylpropionylamino)phenyl]piperidine;
(±)-N-hexyl-trans-3,4-dimethyl-4-[3-hydroxy-4-(2-methylbutanoyl)phenyl]piperidine;
(±)-N-hexyl-trans-3,4-dimethyl-4-(3-hydroxy-4-butanoylaminophenyl)piperidine;
(±)-N-hexyl-trans-3,4-dimethyl-4-(3-hydroxy-4-methanesulfonylaminophenyl)piperidine;
(±)-N-hexyl-trans-3,4-dimethyl-4-(4-formyl-3-hydroxyphenyl)piperidine;
(±)-N-hexyl-trans-3,4-dimethyl-4-(3-hydroxy-2,4,6-trichlorophenyl)piperidine;
(±)-N-hexyl-trans-3,4-dimethyl-4-(3-aminosulfonyl-3-hydroxyphenyl)piperidine;
(±)-N-hexyl-trans-3,4-dimethyl-4-(4,6-dichloro-3-hydroxyphenyl)piperidine;
(±)-N-hexyl-trans-3,4-dimethyl-4-(3-hydroxy-4-N'-isopropylaminocarbonylphenyl)piperidine;
(±)-N-hexyl-trans-3,4-dimethyl-4-(4-chloro-3-hydroxyphenyl)piperidine;
(±)-N-hexyl-trans-3,4-dimethyl-4-(6-chloro-3-hydroxyphenyl)piperidine;
(±)-N-hexyl-trans-3,4-dimethyl-4-(4-aminocarbonyl-3-hydroxyphenyl)piperidine;
(±)-N-hexyl-trans-3,4-dimethyl-4-(4-fluoro-3-hydroxyphenyl)piperidine;
(±)-N-hexyl-trans-3,4-dimethyl-4-(2-fluoro-3-hydroxyphenyl)piperidine;
(±)-N-3-cyclohexylpropyl-trans-3,4-dimethyl-4-(3-hydroxy-4-nitrophenyl)piperidine;
(±)-N-(3-cyclohexylpropyl)-trans-3,4-dimethyl-4-(4-amino-3-hydroxyphenyl)piperidine;
(±)-N-(3-cyclohexylpropyl)-trans-3,4-dimethyl-4-(3-hydroxy-4-acetylaminophenyl)piperidine;
(±)-N-(3-cyclohexylpropyl)-trans-3,4-dimethyl-4-(3-hydroxy-4-propionylaminophenyl)piperidine;
(±)-N-hexyl-trans-3,4-dimethyl-4-(4-N',N'-dimethylamino-3-hydroxyphenyl)piperidine;
(±)-N-hexyl-trans-3,4-dimethyl-4-(3-hydroxy-4-isopropenylphenyl)piperidine;
(±)-N-hexyl-trans-3,4-dimethyl-4-(4-allyl-3-N',N'-diethylcarbamyloxyphenyl)piperidine;
(±)-N-hexyl-trans-3,4-dimethyl-4-(3-N',N'-diethylcarbamyloxy-4-methylphenyl)piperidine;
(±)-N-hexyl-trans-3,4-dimethyl-4-(3-N',N'-diethylcarbamyloxy-4-ethylphenyl)piperidine;
(±)-N-hexyl-trans-3,4-dimethyl-4-(3-N',N'-diethylcarbamyloxy-4-N''-methylaminocarbonylphenyl)piperidine;
(±)-N-hexyl-trans-3,4-dimethyl-4-(3-N',N'-diethylthiocarbamyloxy-4-fluorophenyl)piperidine; or
(±)-N-hexyl-trans-3,4-dimethyl4-(3-N',N'-diethylcarbamyloxy-4-formylphenyl)piperidine,
which compounds may also be termed "compounds of the invention".

According to a further aspect of the invention there is provided processes for the preparation of compounds of the invention, as illustrated below.

The following processes are illustrative of the general synthetic procedures which may be adopted in order to obtain the compounds of the invention.

1. Compounds of formula I wherein $R^3$ represents $C_1$ alkyl optionally substituted by $C_{3-8}$ cycloalkyl, Het$^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $R^3$ represents $C_{2-10}$ alkyl, $C_{3-10}$ alkenyl or $C_{3-10}$ alkynyl (which three groups are all optionally substituted by one or more of the relevant substituents identified hereinbefore in respect of $R^3$), which alkyl, alkenyl or alkynyl groups are attached to the piperidine nitrogen atom via a $CH_2$ group, wherein Het$^1$ is as hereinbefore defined, may be prepared by reduction of a corresponding compound of formula II,

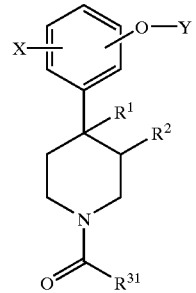

II wherein $R^{31}$ represents H, $C_{3-8}$ cycloalkyl, Het$^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{4e}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, Het$^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or —W—A¹—N(R$^{5b}$)(R$^{5c}$), and R¹, R², R$^{4c}$, R$^{4d}$, R$^{5a}$ to R$^{5c}$, R⁶, Het¹, n, X, Y, W and A¹ are as hereinbefore defined, using a suitable reducing agent (e.g. lithium aluminium hydride or a borane derivative), for example as described hereinbefore.

Compounds of formula II may be prepared by reaction of a corresponding compound of formula III,

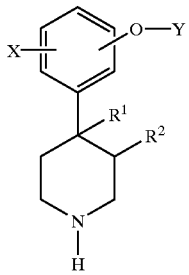

wherein R¹, R², X and Y are as hereinbefore defined with a compound of formula IV,

    IV or a suitable (e.g. carboxylic acid) derivative thereof (e.g. an acid halide or anhydride), wherein R$^{31}$ is as hereinbefore defined, using coupling conditions known to those skilled in the art.

Compounds of formula III may be prepared from appropriate precursors by analogy with other methods disclosed herein that describe the production of compounds of formula I.

2. Compounds of formula I may also be prepared by reaction of a corresponding compound of formula III, as hereinbefore defined, with a compound of formula V,

    V wherein L¹ represents a leaving group (such as halo, alkanesulfonate, perfluoroalkanesulfonate or arenesulfonate) and R³ is as hereinbefore defined, under conditions that are known to those skilled in the art, which include, for example, alkylation at between room temperature and reflux temperature in the presence of a reaction-inert organic solvent (e.g. N,N-dimethylformamide) and a suitable base (e.g. NaHCO₃), and arylation at between room temperature and reflux temperature in the presence of a suitable catalyst system (e.g. tris(dibenzylideneacetone) palladium(0) combined with tri-o-tolylphosphine), an appropriate strong base (e.g. sodium tert-butoxide) and a reaction-inert solvent (e.g. toluene).

3. Compounds of formula I wherein R³ represents C₁ alkyl, which, in place of being optionally substituted by the substituents as defined hereinbefore, is instead optionally substituted by R$^{31}$, wherein R$^{31}$ is as hereinbefore defined, may be prepared by reaction of a corresponding compound of formula III, as hereinbefore defined, with a compound of formula VI,

    VI wherein R$^{31}$ is as hereinbefore defined, for example in the presence of a suitable reducing agent (e.g. sodium borohydride, sodium cyanoborohydride or sodium triacetoxyborohydride) and an appropriate solvent (e.g. methanol).

4. Compounds of formula I wherein R³ is a C$_{1-10}$ alkyl, C$_{4-10}$ alkenyl or C$_{4-10}$ alkynyl group that is fully saturated from 1- to 3-C (relative to the piperidine N-atom), and which R³ group is substituted at 2-C (relative to the piperidine N-atom) by S(O)R$^{4d}$, S(O)₂R$^{4d}$, alkanoyl, cycloalkanoyl, alkoxy carbonyl, CN, —C(O)—A¹—N(R$^{5b}$)(R$^{5c}$), —S(O)—A¹—N(R$^{5b}$)(R$^{5c}$), or —S(O)₂—A¹—N(R$^{5b}$)(R$^{5c}$), wherein R$^{4d}$, R$^{5b}$, R$^{5c}$ and A¹ are as hereinbefore defined, may be prepared by reaction of a corresponding compound of formula III, as hereinbefore defined, with a compound of formula VII,

    VII wherein R$^{3a}$ represents R³ as hereinbefore defined except that it does not represent aryl, and that the R$^{3a}$ chain contains an additional carbon-carbon double bond α,β to the Z-substituent, and Z represents S(O)R$^{4d}$, S(O)₂R$^{4d}$, alkanoyl, cycloalkanoyl, alkoxy carbonyl, CN, —C(O)—A¹—N(R$^{5b}$)(R$^{5c}$), —S(O)—A¹—N(R$^{5b}$)(R$^{5c}$), or —S(O)₂—A¹—N(R$^{5b}$)(R$^{5c}$), wherein R$^{4d}$, R$^{5b}$, R$^{5c}$ and A¹ are as hereinbefore defined, for example at between room and reflux temperature in the presence of a reaction-inert solvent (e.g. THF).

5. Compounds of formula I in which Y represents —C(=E)NR⁸R⁹, wherein E, R⁸ and R⁹ are as hereinbefore defined, may be prepared by reaction of a corresponding compound of formula I in which Y represents H, with a compound of formula VIII,

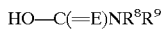    VIII, or a suitable (e.g. carboxylic acid) derivative thereof (e.g. an acid chloride), wherein E, R⁸ and R⁹ are as hereinbefore defined, or a compound of formula IX,

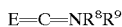    IX wherein E, R⁸ and R⁹ are as hereinbefore defined, for example (in both cases) at between room and reflux temperature in the presence of a suitable base (e.g. KOH, triethylamine and/or pyridine) and optionally in the presence of an appropriate solvent (e.g. THF, water, or a suitable mixture thereof).

6. Compounds of formula I in which Y represents C(O)R¹⁰ or C(O)OR¹⁰, wherein R¹⁰ is as hereinbefore defined, may be prepared by reaction of a corresponding compound of formula I in which Y represents H, with a compound of formula X,

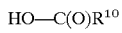    X, or a compound of formula XI,

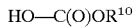    XI respectively, or suitable (e.g. carboxylic acid) derivatives thereof (e.g. acid halides or anhydrides), wherein R¹⁰ is as hereinbefore defined, under coupling conditions known to those skilled in the art.

7. Compounds of formula I in which Y represents C(O)CH(R$^{10a}$)N(G)(G$^a$), wherein R$^{10a}$, G and G$^a$ are as hereinbefore defined may be prepared by reaction of a corresponding compound of formula I in which Y represents H, with a compound of formula XII,

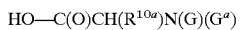    XII or a suitable (e.g. carboxylic acid) derivative thereof, wherein R$^{10a}$, G and G$^a$ are as hereinbefore defined, under coupling conditions known to those skilled in the art.

8. Compounds of formula I in which Y represents C(O)C($R^{13a}$)=C($R^{13b}$)$NH_2$ or C(O)CH($R^{13a}$)CH($NH_2$)($R^{13b}$), and $R^{13a}$ and $R^{13b}$ are as hereinbefore defined, may be prepared by reaction of a corresponding compound of formula I in which Y represents H, with a compound of formula XIII,

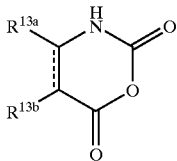

XIII wherein the dashed line represents an optional double bond, and $R^{13a}$ and $R^{13b}$ are as hereinbefore defined, for example at between room and reflux temperature in the presence of a suitable solvent (e.g. N,N-dimethylformamide) and an appropriate base (e.g. N,N-dimethyl-4-aminopyridine).

9. Compounds of formula I in which Y represents C(O)$R^{10}$, wherein $R^{10}$ represents phenyl substituted in the ortho-position by an amino group, and optionally substituted by one or more further substituents selected from OH, halo, $C_{1-4}$ alkanoyl, $C_{1-4}$ alkanoyloxy, N($R^8$)($R^9$), C(O)N($R^8$)($R^9$), $C_{1-4}$ alkyl and $C_{1-4}$ alkoxy (which latter two groups are optionally substituted by one or more halo atoms), and $R^8$ and $R^9$ are as hereinbefore defined, may be prepared by reaction of a corresponding compound of formula I in which Y represents H with a compound of formula XIV,

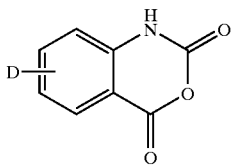

XIV wherein D represents one to four optional substituents selected from OH, halo, $C_{1-4}$ alkanoyl, $C_{1-4}$ alkanoyloxy, N($R^8$)($R^9$), C(O)N($R^8$)($R^9$), $C_{1-4}$ alkyl and $C_{1-4}$ alkoxy (which latter two groups are optionally substituted by one or more halo atoms), and $R^8$ and $R^9$ are as hereinbefore defined, for example at between room and reflux temperature in the presence of a suitable solvent (e.g. N,N-dimethylformamide) and an appropriate base (e.g. N,N-dimethyl-4-aminopyridine).

10. Compounds of formula I in which Y represents $R^{11}$, wherein $R^{11}$ is as hereinbefore defined, may be prepared by reaction of a corresponding compound of formula I in which Y represents H, with a compound of formula XV, $R^{11}$—$L^2$  XV wherein $L^2$ represents a leaving group such as halo, arenesulfonate, alkanesulfonate, perfluoroalkanesulfonate or diazo, and $R^{11}$ is as hereinbefore defined, for example under coupling conditions known to those skilled in the art (such as those described above in respect of process 2 above).

11. Compounds of formula I in which Y represents CH($R^{12b}$)C(O)O$R^{12a}$ or CH($R^{12b}$)OC(O)O$R^{12a}$, wherein $R^{12a}$ and $R^{12b}$ are as hereinbefore defined, may be prepared by reaction of a corresponding compound of formula I in which Y represents H, with a compound of formula XVI, $L^2$—CH($R^{12b}$)C(O)O$R^{12a}$  XVI or a compound of formula XVII, $L^2$—CH($R^{12b}$)OC(O)O$R^{12a}$  XVII wherein $R^{12a}$, $R^{12b}$ and $L^2$ are as hereinbefore defined, for example under coupling conditions known to those skilled in the art (such as those described in respect of process 2 above).

12. Compounds of formula I in which Y represents PO(O$R^{14}$)$_2$, wherein $R^{14}$ is as hereinbefore defined, may be prepared by reaction of a compound of formula I in which Y represents H, with a compound of formula XVIII,

H—PO(O$R^{14}$)$_2$  XVIII or a compound of formula XIX,

HO—PO(O$R^{14}$)$_2$  XIX or a suitable (e.g. phosphoric acid) derivative thereof (e.g. a pyrophosphate, cyanophosphate or chlorophosphate), wherein $R^{14}$ is as hereinbefore defined, for example at between −10° C. and reflux temperature in the presence of a suitable base (e.g. NaH, triethylamine) and an appropriate organic solvent (e.g. THF, dichloromethane or carbon tetrachloride).

13. Compounds of formula I in which X represents halo and optionally one or more further substituents hereinbefore defined in respect of X, may be prepared by reaction of a corresponding compound of formula XX,

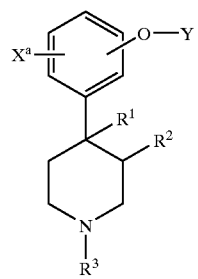

XX wherein $X^a$ represents one H and optionally one to three of the substituents hereinbefore defined in respect of X, and $R^1$, $R^2$, $R^3$ and Y are as hereinbefore defined, with a suitable halogenating agent (e.g. a solution of the halogen in acetic acid, or a fluorinating agent such as 3,5-dichloro-1-fluoropyridinium triflate or N-fluorobenzenesulfonimide), for example under conditions known to those skilled in the art.

Compounds of formula XX may be prepared by N-alkylation of a corresponding compound of formula XXI,

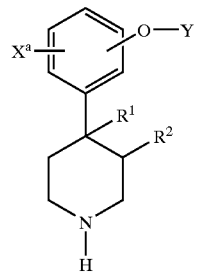

XXI wherein $R^1$, $R^2$, $X^a$ and Y are as hereinbefore defined, for example under conditions hereinbefore described for the preparation of compounds of formula I (see, for example, those described in respect of processes 2 to 4 above).

Compounds of formula XX in which $R^3$ represents $C_1$ alkyl, which, in place of being optionally substituted by the substituents as defined hereinbefore, is instead optionally substituted by $R^{31}$, wherein $R^{31}$ is as hereinbefore defined, may alternatively be prepared by reduction of a corresponding compound of formula XXII,

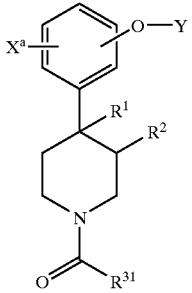

XXII wherein $R^1$, $R^2$, $R^{31}$, $X^a$ and Y are as hereinbefore defined, for example under conditions hereinbefore described for the preparation of compounds of formula I (see, for example, those described in respect of process 1 above).

Compounds of formula XXI and XXII may be prepared from appropriate precursors by analogy with other methods disclosed herein that describe the production of compounds of formula I.

14. Compounds of formula I in which X represents nitro and optionally one or more further substituents hereinbefore defined in respect of X, may be prepared by nitration of a corresponding compound of formula XX, as hereinbefore defined, under conditions known to those skilled in the art, for example by reaction with a suitable source of the nitronium ion (e.g. nitronium tetrafluoroborate) at between −10° C. and room temperature in the presence of a suitable solvent (e.g. acetonitrile).

15. Compounds of formula I in which X represents $S(O)_2OH$ and optionally one or more further substituents hereinbefore defined in respect of X, may be prepared by sulfonation of a corresponding compound of formula XX, as hereinbefore defined, under conditions known to those skilled in the art, for example by reaction with chlorosulfonic acid at between −10° C. and room temperature in the presence of thionyl chloride, followed by hydrolysis of the resulting sulfonyl chloride. The reaction may alternatively performed with sulfur trioxide, for example at between −10° C. and reflux temperature in the presence of pyridine.

16. Compounds of formula I in which X represents $S(O)_tR^{17a}$, wherein t is 0, and optionally one or more further substituents hereinbefore defined in respect of X, wherein $R^{17a}$ is as hereinbefore defined except that it does not represent $N(R^{20a})(R^{20b})$, wherein $R^{20a}$ and $R^{20b}$ are as hereinbefore defined, may be prepared by sulfenylation of a corresponding compound of formula XX, as hereinbefore defined, under conditions known to those skilled in the art, for example by reaction with a compound of formula XXIII,

  XXIII wherein $R^{21}$ represents $R^{17a}$ as hereinbefore defined except that it does not represent $N(R^{20a})(R^{20b})$, wherein $R^{20a}$ and $R^{20b}$ are as hereinbefore defined, at between −90° C. and room temperature in the presence of a suitable strong base (e.g. an alkyllithium reagent) and an appropriate organic solvent (e.g. N,N,N',N'-tetramethylethylenediamine), or by reaction with a compound of formula XXIV,

  XXIV wherein $R^{21}$ is as hereinbefore defined, at between 0° C. and reflux temperature in the presence of an appropriate organic solvent (e.g. dichloromethane) and optionally in the presence of a suitable catalyst (e.g. iron powder).

17. Compounds of formula I in which X represents $C(O)R^{16a}$ and optionally one or more further substituents hereinbefore defined in respect of X, wherein $R^{16a}$ is as hereinbefore defined except that it does not represent H, may be prepared by acylation of a corresponding compound of formula XX, as hereinbefore defined, under conditions known to those skilled in the art, for example by reaction with a compound of formula XXV,

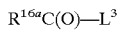  XXV wherein $L^3$ represents a leaving group (such as halo, OH, $OS(O)_2CF_3$ or $OC(O)R^{16a}$) and $R^{16a}$ is as hereinbefore defined except that it does not represent H, for example under Friedel-Crafts conditions (e.g. at between room and reflux temperature in the presence of a suitable solvent and optionally in the presence of an appropriate catalyst).

18. Compounds of formula I in which X represents C(O)H and optionally one or more further substituents hereinbefore defined in respect of X, may be prepared by reaction of a corresponding compound of formula XX, as hereinbefore defined, with dimethylformamide, for example under Vilsmeier-Haack conditions or at between −90° C. and room temperature in the presence of a suitable strong base (e.g. alkyllithium reagent) and an appropriate organic solvent (e.g. N,N,N',N'-tetramethylethylenediamine, THF, cyclohexane or mixtures thereof).

19. Compounds of formula I in which X represents $OC(O)R^{16c}$ and optionally one or more further substituents hereinbefore defined in respect of X, wherein $R^{16c}$ is as hereinbefore defined, may be prepared by oxidation of a corresponding compound of formula I in which X represents $C(O)RL^{6a}$, wherein $R^{16a}$ is as hereinbefore defined, for example under Baeyer-Villiger conditions, i.e. at between room and reflux temperature in the presence of an appropriate peroxy acid (e.g. 3-chloroperoxybenzoic acid) and a suitable organic solvent (e.g. dichloromethane).

20. Compounds of formula I in which X and/or OY represent OH may be prepared by reaction of a corresponding compound of formula I in which X represents $OC(O)R^{16c}$, wherein $R^{16c}$ is as hereinbefore defined, and/or Y represents $C(=E)NR^8R^9$, wherein $R^8$ and $R^9$ are as hereinbefore defined, under conditions well know to those skilled in the art (e.g. hydrolysis or reductive cleavage).

21. Compounds of formula I in which X represents $C_{1-10}$ alkyl, $C_{3-10}$ alkenyl, $C_{3-10}$ alkynyl, $C_{3-7}$ cycloalkyl (which four groups are optionally substituted as defined hereinbefore, and which alkenyl and alkynyl groups are fully saturated at 1-C (relative to the benzene ring)) and optionally one or more further substituents hereinbefore defined in respect of X, may be prepared by reaction of a corresponding compound of formula XX, as hereinbefore defined, with a compound of formula XXVI,

  XXVI wherein $R^{22}$ represents $C_{1-10}$ alkyl, $C_{2-10}$ alkenyl, $C_{2-10}$ alkynyl, $C_{3-7}$ cycloalkyl (which four groups are optionally substituted by one or more substituents selected from halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy or $N(R^{15a})(R^{15b})$ and which alkenyl and alkynyl groups are fully saturated at 1-C (relative to $L^2$)) and $L^2$, $R^{15a}$ and $R^{15b}$ are as hereinbefore defined, for example either under Friedel-Crafts alkylation conditions or at between −90° C. and room temperature in the presence of a suitable strong base (e.g. an alkyllithium reagent) and an appropriate organic solvent (e.g. N,N,N',N'-tetramethylethylenediamine, THF, cyclohexane or mixtures thereof).

22. Compounds of formula I in which X represents $C(O)N(R^{18c})(R^{18d})$, which group is in the ortho-position relative to OY, in which $R^{18c}$ and $R^{18d}$ independently represent $C_{1-4}$ alkyl or $C_{3-7}$ cycloalkyl, and Y represents H, may be prepared by rearrangement of a corresponding compound of formula XXVII,

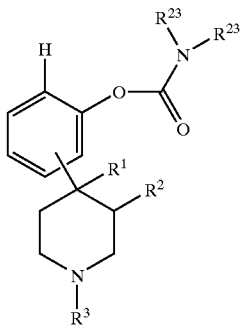 XXVII wherein $R^{23}$ represents $C_{1-4}$ alkyl or $C_{3-7}$ cycloalkyl, and $R^1$, $R^2$, and $R^3$ are as hereinbefore defined, for example at between −90° C. and room temperature in the presence of a suitable strong base (e.g. an alkyllithium reagent) and an appropriate organic solvent (e.g. N,N,N',N'-tetramethylethylenediamine, THF, cyclohexane or mixtures thereof).

23. Compounds of formula I in which X represents $C_{2-10}$ alkenyl and optionally one or more further substituents hereinbefore defined in respect of X, wherein the double bond of the alkenyl chain is α,β- to the benzene ring, may be prepared by reaction of a corresponding compound of formula XX, as hereinbefore defined, with a $C_{2-10}$ aldehyde or a $C_{2-10}$ ketone, for example at between −90° C. and room temperature in the presence of a suitable strong base (e.g. an alkyllithium reagent) and an appropriate organic solvent (e.g. N,N,N',N'-tetramethylethylenediamine, THF, cyclohexane or mixtures thereof).

24. Compounds of formula I in which X represents $C(O)N(H)R^{18c}$ and optionally one or more further substituents hereinbefore defined in respect of X, wherein $R^{18c}$ represents $C_{1-4}$ alkyl or $C_{3-7}$ cycloalkyl may be prepared by reaction of a corresponding compound of formula XX, as hereinbefore defined, with a compound of formula XXVIII, $$O=C=N-R^{23} \quad\quad XXVIII$$

wherein $R^{23}$ is as hereinbefore defined, for example at between −90° C. and room temperature in the presence of a suitable strong base (e.g. an alkyllithium reagent) and an appropriate organic solvent (e.g. N,N,N',N'-tetramethylethylenediamine, THF, cyclohexane or mixtures thereof).

25. Compounds of formula I in which X represents $B(OCH_3)_2$ and optionally one or more further substituents hereinbefore defined in respect of X, may be prepared by reaction of a corresponding compound of formula XX, as hereinbefore defined, with trimethyl borate, for example at between −90° C. and room temperature in the presence of a suitable strong base (e.g. an alkyllithium reagent) and an appropriate organic solvent (e.g. N,N,N',N'-tetramethylethylenediamine, THF, cyclohexane or mixtures thereof).

26. Compounds of formula I in which X represents $C_{2-10}$ alkenyl or $C_{2-10}$ alkynyl, which alkenyl and alkynyl groups contain a carbon-carbon multiple bond that is α,β to the benzene ring, and which alkenyl and alkynyl groups are optionally substituted as defined hereinbefore in respect of X, and optionally one or more further substituents hereinbefore defined in respect of X, may be prepared by reaction of a corresponding compound of formula I in which at least one X represents halo with a compound of formula XXIX, $$R^{24}-M \quad\quad XXIX$$

wherein $R^{24}$ represents $C_{2-10}$ terminal alkenyl or $C_{2-10}$ terminal alkynyl, which alkenyl and alkynyl groups are optionally substituted by one or more substituents selected from halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy or $N(R^{15a})(R^{15b})$, M represents (as appropriate) H, a tin-containing moiety (e.g. tributylstannyl), a boron derivative (e.g. a boronic acid), a zinc halide, a magnesium halide or an alkali metal (which latter three groups may be formed in situ from the corresponding halide), and $R^{15a}$ and $R^{15b}$ are as hereinbefore defined, for example at between room and reflux temperature in the presence of a suitable catalyst system (e.g. tetrakis(triphenylphosphine)palladium(0), bis (triphenylphosphine)palladium(II) acetate, or bis (triphenylphosphine)palladium(II) chloride combined with copper(I) iodide) and either (as appropriate) a suitable source of halide ion (e.g. lithium chloride) or a suitable base (e.g. triethylamine).

Compounds of formulae III to XIX, XXIII to XXIX, and derivatives thereof, when not commercially available or not subsequently described, is may be obtained either by analogy with the processes described herein, or by conventional synthetic procedures, in accordance with standard techniques, from readily available starting materials using appropriate reagents and reaction conditions (see, for example, "Comprehensive Organic Transformations—A Guide to Functional Group Preparations", R. C. Larrock, VCH (1989), or "Advanced Organic Chemistry—Reactions, Mechanism and Structure", $4^{th}$ edition, J. March, Wiley-Interscience (1992)). For example, compounds of formula XX in which both $X^a$ and Y represent H may be made according to or by analogy with the procedures disclosed in the publications mentioned above relating to 4-arylpiperidine-based compounds.

The skilled person will appreciate that certain groups falling within the definition of Y will serve as protective groups during the introduction and/or interconversion of certain X groups, for the synthesis of corresponding compounds in which Y represents H. For example, the group —C(=E)NR⁸R⁹ may serve to prevent reaction at phenolic oxygen under conditions such as those described in relation to processes 16, 18, 19, 21 and 23 to 25 above.

Substituents on alkyl, heterocyclic and aryl groups in the above-mentioned compounds may also be introduced, removed and interconverted, using techniques which are well known to those skilled in the art (including those specifically disclosed hereinbefore). For example, nitro may be reduced to amino, OH may be alkylated to give alkoxy, alkoxy and alkanoyloxy may be hydrolysed to OH, alkenes may be hydrogenated to alkanes, halo may be hydrogenated to H, etc.

The skilled person will also appreciate that other various standard substituent or functional group interconversions and transformations within compounds of formula I will provide other compounds of formula I. In particular, certain functional groups falling within the definitions of the group X may be converted to other such definitions. For example: amino may be converted to alkylamino, dialkylamino, alkylcarbonylamino, alkylsulfonylamino, aminocarbonylamino, alkoxycarbonylamino and aminosulfonylamino; sulfonate may be converted to aminosulfonyl; formyl may be converted to hydroxymethyl, aminomethyl, alkylaminomethyl, dialkylaminomethyl and alkoxycarbonyl; methyl may be converted to ethyl; alkoxycarbonyl may be converted to aminocarbonyl, alkylaminocarbonyl and dialkylaminocarbonyl; aminocarbonyl may be converted to alkanoyl; sulfanyl may be converted to sulfinyl or sulfonyl; and dialkyl borate may be converted to dihydroxyboryl, all of which transformations may be performed using techniques, and under reaction conditions, that are known to those skilled in the art. Also, certain groups representing Y may be converted to certain other groups representing Y.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, OH, amino and carboxylic acid. Suitable protective groups for oxo include acetals, ketals (e.g. ethylene ketals) and dithianes. Suitable protective groups for OH include trialkylsilyl and diarylalkylsilyl groups (e.g. tert-butyldimethylsilyl, tert-butyldiphenylsilyl or trimethylsilyl) and tetrahydropyranyl. Suitable protective groups for amino include tert-butyloxycarbonyl, 9-fluorenylmethoxycarbonyl or benzyloxycarbonyl. Suitable protective groups for carboxylic acid include $C_{1-6}$ alkyl or benzyl esters. Suitable protective groups for terminal alkynes include trialkylsilyl and diarylalkylsilyl groups (e.g. tert-butyldimethylsilyl, tert-butyldiphenylsilyl or trimethylsilyl). Suitable protective groups for arene protons include trialkylsilyl groups.

The protection and deprotection of functional groups may take place before or after any of the reaction steps described hereinbefore.

Protective groups may be removed in accordance with techniques which are well known to those skilled in the art.

The use of protecting groups is fully described in "Protective Groups in Organic Chemistry", edited by JWF McOmie, Plenum Press (1973), and "Protective Groups in Organic Synthesis", $2^{nd}$ edition, TW Greene & PGM Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

Pharmaceutically acceptable acid addition salts of the compounds of formula I which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I with the appropriate base, Both types of salt may be formed or interconverted using ion-exchange resin techniques.

The above procedures may be adapted as appropriate to the particular reactants and groups involved and other variants will be evident to the skilled chemist by reference to standard textbooks and to the examples provided hereafter to enable all of the compounds of formula I to be prepared.

Compounds of the invention may possess pharmacological activity as such. Compounds of the invention that may possess such activity include, but are not limited to, those in which Y represents H.

Other compounds of formula I (including, but not limited to, those in which Y does not represent H) may not possess such activity per se, but may be administered parenterally or orally, and thereafter metabolised in the body to form compounds that are pharmacologically active (including, but not limited to, corresponding compounds in which Y represents H). Such compounds (which also include compounds that may possess some pharmacological activity, but that activity is appreciably lower than that of the active compounds to which they are metabolised to), may therefore be described as "prodrugs".

Further, it will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may also therefore be described as "prodrugs". Further, certain compounds of formula I may act as prodrugs of other compounds of formula I.

It will be further appreciated by those skilled in the art, that certain moieties, known to those skilled in the art as "pro-moieties", for example as described in 'Design of Prodrugs' by H. Bundgaard, Elsevier, 1985 (the disclosure in which document is hereby incorporated by reference), may be placed on appropriate functionalities, when such functionalities are present within compounds of formula I.

All protected derivatives, and prodrugs, of compounds of formula I are included within the scope of the invention.

The compounds of the invention are useful because they possess pharmacological activity, and/or are metabolised in the body following oral or parenteral administration to form compounds which possess pharmacological activity. The compounds of the invention are therefore indicated as pharmaceuticals and, in particular, for use as animal medicaments.

According to a further aspect of the invention there is provided the compounds of the invention for use as medicaments, such as pharmaceuticals and animal medicaments.

By the term "treatment", we include both therapeutic (curative) or prophylactic treatment.

In particular, the compounds of the invention have been found to be useful in the treatment of pruritus, and conditions characterised by pruritus as a symptom.

Thus, according to a further aspect of the invention there is provided the use of the compounds of the invention in the manufacture of a medicament for the treatment of pruritus or a medical condition characterised by pruritus as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing pruritus or a medical condition characterised by pruritus as a symptom in an animal (e.g. a mammal), which comprises administering a therapeutically effective amount of a compound of the invention to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, e.g. fipronil, lufenuron, imidacloprid, avermectins (e.g. abamectin, ivermectin, doramectin), milbemycins, organophosphates, pyrethroids; antihistamines, e.g. chlorpheniramine, trimeprazine, diphenhydramine, doxylamine; antifungals, e.g. fluconazole, ketoconazole, itraconazole, griseofulvin, amphotericin B; antibacterials, e.g. enroflaxacin, marbofloxacin, ampicillin, amoxycillin; anti-inflammatories e.g. prednisolone, betamethasone, dexamethasone, carprofen, ketoprofen; dietary supplements, e.g. gamma-linoleic acid; and emollients. Therefore, the invention further provides a product containing a compound of the invention and a compound from the above list as a combined preparation for simultaneous, separate or sequential use in the treatment of pruritus.

The skilled person will also appreciate that compounds of the invention may be taken as a single dose on an "as required" basis (i.e. as needed or desired).

Thus, according to a further aspect of the invention there is provided a pharmaceutical, or veterinary, formulation including a compound of the invention in admixture with a pharmaceutically, or veterinarily, acceptable adjuvant, diluent or carrier.

Compounds of the invention may also have the advantage that, in the treatment of human and/or animal patients, they may be, or may be metabolised to form compounds that may be, more efficacious than, be less toxic than, have a broader range of activity than, be more potent than, produce fewer side effects than, be more easily absorbed than, or they may have other useful pharmacological properties over, compounds known in the prior art.

The biological activity of the compounds of the present invention was determined by the following test method.

Biological Test

The compounds of the invention are evaluated for their activity as antipruritic agents by measuring their ability to inhibit the hind leg scratching behaviour induced in rats by the administration of a known pruritogenic agent. These studies are based on the procedure described by Berendsen and Broekkamp in the European Journal of Pharmacology, 1991, 194, 201. The test is performed as follows:

Male Wistar rats (approximately 150 g body weight) are challenged with a pruritogen by subcutaneous injection of 5-methoxytryptamine hydrochloride (4 mg/3 mL/kg) dissolved in physiological saline into the scruff of the neck. At this dose a constant and quantifiable hindleg scratching response lasting up to 90 minutes is obtained.

The test compound is administered to the test animals by subcutaneous injection in an aqueous micelle formulation. The test compound is prepared in the following manner. The compound is dissolved in a vehicle (composition v/v %: glycerol formal, 24; tween 80, 17; benzyl alcohol, 1.5 and purified water to 100) then seven parts purified water is added to three parts of the above vehicle to give the aqueous micelle formulation. The compounds can be administered pre- or post-challenge or may be administered at the same time as the pruritogenic challenge.

After the pruritogen challenge has been administered, hindleg scratching is scored for each animal by recording the presence or absence of scratching during each 30 second interval as 1 or 0 scored respectively. The score for each animal is totalled after 25 minutes (maximum score 50). The efficacy of compounds is assessed by their ability to significantly reduce the score in treated groups compared to the control group.

The invention is illustrated by the following Preparations and Examples in which the following abbreviations may be used:
APCI=atmospheric pressure chemical ionisation
br (in relation to NMR)=broad
CI=chemical ionisation
DMF=N,N-dimethylformamide
DMSO=dimethylsulfoxide
d (in relation to time)=day
d (in relation to NMR)=doublet
dd (in relation to NMR)=doublet of doublets
EtOAc=ethyl acetate
EtOH=ethanol
ESI=electrospray ionisation
h=hour(s)
m (in relation to NMR)=multiplet
MeOH=methanol
min=minute
q (in relation to NMR)=quartet
s (in relation to NMR)=singlet
t (in relation to NMR)=triplet
td (in relation to NMR)=triplet of doublets
THF=tetrahydrofuran
TSI=thermospray ionisation When reverse phase HPLC is mentioned in the text the following 2 sets of conditions were employed.
Condition 1: A Phenomenex Magellen™ column, 150×21 mm, packed with 5 m $C_{18}$ silica, eluting with a gradient of acetonitrile:0.1 M aqueous ammonium acetate (30:70 to 95:5 over 10 mins, flow rate 20 mL per min).
Condition 2: A Dynamax™ column, 42×250 mm, packed with $8\mu$ $C_{18}$ silica, eluting with acetonitrile:0.1 M aqueous ammonium acetate (30:70) at 45 mL per minute.

In both cases, combination and evaporation of appropriate fractions, determined by analytical HPLC, provided the desired compounds as acetate salts.

Analytical HPLC conditions used to highlight appropriate fractions were Phenomenex Magellan™ column, 4.6×150 mm, packed with $5\mu$ $C_{18}$ silica, eluting with a gradient of acetonitrile:0.1 M aqueous heptanesulfonic acid (10:90 to 90:10 over 30 min, followed by a further 10 min at 90:10) at 1 mL per minute. Column oven temperature was 40° C., and ultraviolet detection of components was made at 220 nM.

When column chromatography is referred to this usually refers to a glass column packed with silica gel (40–63 $\mu$m). Pressure of about 165 kPa is generally applied and the ratio of crude product:silica gel required for purification is typically 50:1. Alternatively, an Isolute™ SPE (solid phase extraction) column or Waters Sep-Pak™ cartridge packed with silica gel may be used under atmospheric pressure. The ratio of crude product to silica gel required for purification is typically 100:1.

Nuclear magnetic resonance (NMR) spectral data were obtained using a Brucker AC3000, AM300 or AM400 spectrometer, the observed chemical shifts ($\delta$) being consistent with the proposed structures. Mass spectral (MS) data were obtained on a Finnigan Mat. TSQ 7000 or a Fisons Instruments Trio 1000 spectrometer. The calculated and observed ions quoted refer to the isotopic composition of lowest mass. HPLC means high performance liquid chromatography. Room temperature means 20 to 25° C.

EXAMPLES

Example 1

(±)-N-Hexyl-trans-3,4-dimethyl-4-(4-bromo-3-hydroxyphenyl)piperidine

To a stirred solution of (±)-N-hexyl-trans-3,4-dimethyl-4-(3-hydroxyphenyl)piperidine (Preparation 7, 49 mg, 0.17 mmol) in acetic acid (1 mL) at 10° C. was added bromine (9 $\mu$L, 0.17 mmol). After 5 minutes, the reaction mixture was diluted with water (10 mL), adjusted to pH 9 with 2N sodium hydroxide, and then extracted with dichloromethane (3×10 mL). The combined extracts were washed with brine (15 mL), dried over $Na_2SO_4$, filtered and concentrated in vacuo to give the crude product, which was purified via silica gel chromatography, eluting with a gradient of methanol-dichloromethane-0.880 ammonia (10:989:1 to 20:978:2), to give the title compound as a yellow oil (53 mg).

NMR ($C_6D_6$, selected data from the free base): 0.82 (d, 3H), 0.86 (t, 3H), 1.10 (s, 3H), 1.16–1.28 (m, 6H), 1.33 (m, 1H), 1.47 (m, 2H), 1.71 (m, 1H), 2.12–2.43 (m, 6H), 2.69 (m, 1H), 6.40 (dd, 1H), 6.94 (d, 1H), 7.33 (d, 1H) and 8.16 (br s, 1H).

MS (APCI$^+$): M/Z [MH$^+$] 368.2; $C_{19}H_{30}BrNO+H$ requires 368.2.

Example 2

(±)-N-Hexyl-trans-3,4-dimethyl-4-(3-hydroxy-4-nitrophenyl)piperidine

To a stirred solution of (±)-N-hexyl-trans-3,4-dimethyl-4-(3-hydroxyphenyl)piperidine (Preparation 7, 2.88 g, 9.96 mmol) in acetonitrile 85 mL) at 0° C. was added a solution of nitronium tetrafluoroborate (1.59 g, 12.0 mmol) in acetonitrile (15 mL). After 2 hours the reaction mixture was diluted with aqueous saturated sodium hydrogencarbonate (100 mL) and extracted with ethyl acetate (3×100 mL). The combined extracts were washed with brine (100 mL), dried ($Na_2SO_4$), filtered and concentrated in vacuo to give the crude product, which was purified via silica gel chromatography, eluting with methanol-dichloromethane-ammonium hydroxide (10:489:1), to give the title compound (1.07 g) as a yellow oil.

NMR ($C_6D_6$, selected data from the free base): 0.71 (d, 3H), 0.87 (t, 3H), 0.92 (s, 3 H), 1.02 (m, 1H), 1.23–1.32 (m, 6H), 1.42 (m, 2H), 1.52 (m, 1H), 1.93 (m, 2H), 2.18 (m, 3H), 2.33 (m, 1H), 2.55 (m, 1H), 6.28 (dd, 1H), 6.78 (d, 1H) and 7.62 (d, 1H).

MS (APCI$^+$): M/Z [MH$^+$] 335.3; $C_{19}H_{30}N_2O_3+H$ requires 335.2.

Example 3

(±)-N-Hexyl-trans-3,4-dimethyl-4-(2,4-dibromo-3-hydroxyphenyl)piperidine

Isolation of the slower eluting compound from Example 1 afforded the title compound (4 mg).

NMR (C$_6$D$_6$, selected data from the free base): 0.80 (d, 3H), 0.87 (t, 3H), 1.08–1.44 (m, 9H), 1.36 (s, 3H), 2.04 (m, 1H), 2.12–2.25 (m, 4H), 2.43 (m, 1H), 2.67 (m, 1H), 2.99 (m, 1H), 6.33 (d, 1H) and 7.05–7.11 (m, 1H).

MS (APCI$^+$): M/Z [MH$^+$] 446.1; C$_{19}$H$_{29}$Br$_2$NO+H requires 446.1.

Example 4

(±)-N-Hexyl-trans-3,4-dimethyl-4-(4-amino-3-hydroxyphenyl)piperidine

To a solution of (±)-N-hexyl-trans-3,4-dimethyl-4-(3-hydroxy-4-nitro-phenyl)piperidine (Example 2, 644 mg, 1.93 mmol) in tetrahydrofuran (15 mL) was added platinum (IV) oxide (9 mg, 0.039 mmol) and the reaction mixture was shaken under 345 kPa of hydrogen gas for 10 hours. The reaction mixture was purged with nitrogen, filtered under nitrogen and the crude product was routinely employed directly in the subsequent reaction. The product may be purified, after concentration in vacuo, via silica gel chromatography, eluting with methanol-dichloromethane-ammonium hydroxide (10:989:1), to give the title compound as an air-sensitive oil.

NMR (C$_6$D$_6$, selected data from the free base): 0.86 (t, 3H), 0.97 (d, 3H), 1.24–1.32 (m, 9H), 1.45 (m, 3H), 1.81 (m, 1H), 2.16–2.41 (m, 5H), 2.53 (m, 1H), 2.78 (m, 1H), 6.42–6.46 (m, 2H) and 6.64 (dd, 1H).

MS (APCI$^+$): M/Z [MH$^+$] 305.3; C$_{19}$H$_{32}$N$_2$O+H requires 305.3.

Example 5

(±)-N-Hexyl-trans-3,4-dimethyl-4-[3-hydroxy-4-(2-methylbutanoyl)phenyl]piperidine To a stirred solution of (±)-N-hexyl-trans-3,4-dimethyl-4-(3-N',N'-diethylcarbamyloxyphenyl)piperidine (Preparation 4, 97 mg, 0.25 mmol) and N,N,N',N'-tetramethylethylenediamine (45 µL, 0.30 mmol) in tetrahydrofuran (2 mL) at −78° C. was added s-butyllithium (0.46 mL of 1.3 M in cyclohexane, 0.60 mmol) and the reaction mixture was allowed to warm to room temperature overnight. The reaction mixture was diluted with water (25 mL) and extracted with dichloromethane (3×20 mL). The combined extracts were washed with brine (30 mL), dried over Na$_2$SO$_4$, filtered and concentrated in vacuo to give the crude product, which was purified via silica gel chromatography, eluting with a gradient of methanol-dichloromethane-0.880 ammonia (10:989:1 to 30:969:1), to give the title compound as a pale yellow oil (26 mg).

NMR (C$_6$D$_6$, selected data from the free base): 0.68 (t, 3H), 0.84–0.89 (m, 6H), 0.95 (d, 3H), 1.12 (s, 3H), 1.18–1.31 (m, 8H), 1.42 (m, 2H), 1.65–1.74 (m, 2H), 2.01–2.41 (m, 6H), 2.63 (m, 1H), 2.97 (m, 1H), 6.64 (dd, 1H), 7.04 (m, 1H) and 7.36 (d, 1H).

MS (APCI$^+$): M/Z [MH$^+$] 374.3; C$_{24}$H$_{39}$NO$_2$+H requires 374.3.

Example 6

(±)-N-Hexyl-trans-3,4-dimethyl-4-(4-allyl-3-hydroxyphenyl)piperidine

To a stirred solution of (±)-N-hexyl-trans-3,4-dimethyl-4-(4-allyl-3-N',N'-diethylcarbamyloxyphenyl)piperidine (Example 50, 0.107 g, 0.25 mmol) in tetrahydrofuran (2 mL) at 0° C. was added lithium aluminium hydride (0.5 mL of 1.0 M in tetrahydrofuran, 0.5 mmol) and the reaction mixture was allowed to warm to room temperature. After 4 hours, the reaction mixture was diluted sequentially with water (20 µL), 15% aqueous sodium hydroxide (20 µL) and water (60 µL), and then allowed to stir for 1 hour. The reaction mixture was filtered through Celite® with the aid of tetrahydrofuran and concentrated in vacuo to give the crude product, which was purified via silica gel chromatography, eluting with a gradient of methanol-dichloromethane-0.880 ammonia (10:989:1 to 30:969:1), to give the title compound as a pale yellow oil (56 mg).

NMR (C$_6$D$_6$, selected data from the free base): 0.85 (t, 3H), 0.90 (d, 3H), 1.23 (s, 3H), 1.23–1.27 (m, 6H), 1.47–1.50 (m, 3H), 1.82 (m, 1H), 2.15–2.51 (m, 6H), 2.80 (m, 1H), 3.38 (d, 2H), 5.00 (m, 2H), 5.98 (m, 1H), 6.71–6.73 (m, 2H) and 7.03 (d, 1H).

MS (APCI$^+$): M/Z [MH$^+$] 330.3; C$_{22}$H$_{35}$NO+H requires 330.3.

Example 7

(±)-N-Hexyl-trans-3,4-dimethyl-4-(3-hydroxy-4-methylphenyl)piperidine

To a stirred solution of (±)-N-hexyl-trans-3,4-dimethyl-4-(3-N',N'-diethylcarbamyloxy-4-methylphenyl)piperidine (Example 51, 45 mg, 0.11 mmol) in tetrahydrofuran (2 mL) at 0° C. was added lithium aluminium hydride (0.22 mL of 1.0 M in tetrahydrofuran, 0.22 mmol) and the reaction mixture was allowed to warm to room temperature. After 4 hours, the reaction mixture was diluted sequentially with water (8 µL), 15% aqueous sodium hydroxide (8 µL) and water (24 µL) and allowed to stir for 0.5 hours. The reaction mixture was filtered through Celite® with the aid of tetrahydrofuran and concentrated in vacuo to give the crude product, which was purified via silica gel chromatography, eluting with a gradient of methanol-dichloromethane-0.880 ammonia (10:989:1 to 30:969:1), to give the title compound as a pale yellow oil (20 mg).

NMR (C$_6$D$_6$, selected data from the free base): 0.85 (t, 3H), 0.93 (d, 3H), 1.23–1.29 (m, 6H), 1.24 (s, 3H), 1.46–1.50 (m, 3H), 1.83 (m, 1H), 2.16–2.53 (m, 6H), 2.18 (s, 3H), 2.80 (m, 1H), 6.61 (d, 1H), 6.68 (dd, 1H) and 6.98 (d, 1H).

MS (APCI$^+$): M/Z [MH$^+$] 304.3; C$_2$H$_{33}$NO+H requires 304.3.

Example 8

(±)-N-Hexyl-trans-3,4-dimethyl-4-(4-acetylamino-3-hydroxyphenyl)piperidine

To a stirred solution of (±)-N-hexyl-trans-3,4-dimethyl-4-(4-amino-3-hydroxyphenyl)piperidine (Example 4, 0.100 g, 0.33 mmol) and pyridine (53 µL, 0.66 mmol) in tetrahydrofuran (3 mL) was added acetic anhydride (34 µL, 0.36 mmol). After 12 h, additional pyridine (27 µL, 0.33 mmol) and acetic anhydride (34 µL, 0.36 mmol) were introduced. After an additional 12 h, the reaction mixture was diluted with aqueous saturated sodium hydrogencarbonate (10 mL) and extracted with dichloromethane (3×10 mL). The combined extracts were washed with brine (20 mL), dried over Na$_2$SO$_4$, filtered and concentrated in vacuo to give the crude product which was dissolved in methanol and allowed to stir for 48 h. The reaction mixture was concentrated in vacuo and purified via silica gel chromatography, eluting with methanol-dichloromethane-0.880 ammonia (2:97.8 0.2), to give the title compound as a yellow oil (42 mg).

NMR (C$_6$D$_6$, selected data from the free base): 0.86 (t, 3H), 0.93 (d, 3H), 1.19 (s, 3H), 1.21–1.34 (m, 6H), 1.40–1.51 (m, 3H), 1.53 (s, 3H), 1.82 (m, 1H), 2.12–2.47 (m, 6H), 2.71 (m, 1H), 6.72 (dd, 1H), 7.13 (d, 1H), 7.28 (d, 1H), 7.73 (s, 1H).

MS (APCI$^+$): M/Z [MH$^+$] 347.3; C$_{21}$H$_{34}$N$_2$O$_2$+H requires 347.3.

Example 9

(±)-N-Hexyl-trans-3,4-dimethyl-4-(3-hydroxy-4-hydroxymethylphenyl)piperidine

To a stirred solution of (±)-N-hexyl-trans-3,4-dimethyl-4-(3-N',N'-diethylcarbamyloxy-4-formylphenyl)piperidine (Example 55, 60 mg, 0.14 mmol) in tetrahydrofuran (2 mL) at 0° C. was added lithium aluminium hydride (0.36 mL of 1.0 M in tetrahydrofuran, 0.36 mmol) and the reaction mixture was allowed to warm to room temperature. After 14 hours, the reaction mixture was diluted sequentially with water (20 μL), 15% aqueous sodium hydroxide (20 μL) and water (60 μL) and allowed to stir for 0.5 hours. The reaction mixture was filtered through Celite® with the aid of tetrahydrofuran and concentrated in vacuo to give the crude product, which was purified via silica gel chromatography, eluting with methanol-dichloromethane-0.880 ammonia (20:479:1), to give the title compound as a pale yellow oil (37 mg).

NMR (C$_6$D$_6$, selected data from the free base): 0.84–0.89 (m, 6H), 1.20 (s, 3H), 1.23–1.31 (m, 6H), 1.38–1.44 (m, 3H), 1.80 (m, 1H), 2.10–2.43 (m, 6H), 2.65 (m, 1H), 3.29 (m, 1H), 4.47 (s, 2H), 6.69 (dd, 1H), 6.77 (d, 1H) and 6.99 (d, 1H).

MS (APCI$^+$): M/Z [MH$^+$] 320.2; C$_{21}$H$_{33}$NO$_2$+H requires 320.3.

Example 10

(±)-N-Hexyl-trans-3,4-dimethyl-4-(3-hydroxy-4-trifluoromethanesulfonylaminophenyl)piperidine To a stirred solution of (±)-N-hexyl-trans-3,4-dimethyl-4-(3-hydroxy-4-aminophenyl)piperidine (Example 4, 0.163 g, 0.54 mmol) and triethylamine (82 μL, 0.59 mmol) in dichloromethane (5 mL) at 0° C. was added trifluoromethanesulfonic anhydride (95 μL, 0.56 mmol). After 2 hours, the reaction mixture was diluted with aqueous saturated sodium hydrogencarbonate (10 mL) and extracted with dichloromethane (3×10 mL). The combined extracts were washed with brine (20 mL), dried over Na$_2$SO$_4$, filtered and concentrated in vacuo to give the crude product, which was purified via silica gel chromatography, eluting with a gradient of methanol-dichloromethane-0.880 ammonia (10:489:1 to 25:474:1), to give the title compound as a brown solid (53 mg).

NMR (CD$_3$OD, selected data from the free base): 0.77 (d, 3H), 0.93 (t, 3H), 1.20 (s, 3H), 1.20–1.61 (m, 9H), 1.93 (m, 1H), 2.20 (m, 1H), 2.49–2.94 (m, 6H), 6.60 (dd, 1H), 6.87 (d, 1H) and 7.51 (d, 1H).

MS (APCI$^+$): M/Z [MH$^+$] 437.2; C$_{20}$H$_{31}$F$_3$N$_2$O$_3$S+H requires 437.2.

Example 11

(±)-N-Hexyl-trans-3,4-dimethyl-4-(4-ethyl-3-hydroxyphenyl)piperidine

To a stirred solution of (±)-N-hexyl-trans-3,4-dimethyl-4-(3-N',N'-diethylcarbamyloxy-4-ethylphenyl)piperidine (Example 52, 94 mg, 0.23 mmol) in tetrahydrofuran (2.5 mL) at 0° C. was added lithium aluminium hydride (0.57 mL of 1.0 M in tetrahydrofuran, 0.57 mmol) and the reaction mixture was allowed to warm to room temperature. After 14 hours, the reaction mixture was diluted sequentially with water (8 μL), 15% aqueous sodium hydroxide (8 μL) and water (24 μL) and allowed to stir for 0.5 hours. The reaction mixture was filtered through Celite® with the aid of tetrahydrofuran and concentrated in vacuo to give the crude product, which was purified via silica gel chromatography, eluting with a gradient of methanol-dichloromethane-0.880 ammonia (10:989:1 to 50:949:1), to give the title compound as a pale yellow oil (43 mg).

NMR (C$_6$D$_6$, selected data from the free base): 0.85 (t, 3H), 0.92 (d, 3H), 1.18–1.25 (m, 12H), 1.46–1.51 (m, 3H), 1.84 (m, 1H), 2.16–2.53 (m, 6H), 2.66 (m, 2H), 2.82 (m, 1H), 6.61 (d, 1H), 6.73 (dd, 1H) and 7.03 (d, 1H).

MS (APCI$^+$): M/Z [MH$^+$] 318.3; C$_{21}$H$_{35}$NO+H requires 318.3.

Example 12

(±)-N-Hexyl-trans-3,4-dimethyl-4-[4-(2,2-dimethylpropanoylamino)-3-hydroxyphenyl]piperidine To a stirred solution of (±)-N-hexyl-trans-3,4-dimethyl-4-(4-amino-3-hydroxyphenyl)piperidine (Example 4, 0.129 g, 0.42 mmol) and triethylamine (65 μL, 0.47 mmol) in dichloromethane (5 mL) at 0° C. was added trimethylacetyl chloride (55 μL, 0.45 mmol) in three equivalent portions. Additional trimethylacetyl chloride was introduced after 1 hour (18 μL, 0.15 mmol) and 2.5 hour (8 μL, 0.065 mmol). After an additional 1 hour, the reaction mixture was diluted with aqueous saturated sodium hydrogencarbonate (20 mL) and extracted with dichloromethane (3×20 mL). The combined extracts were washed with brine (20 mL), dried over Na$_2$SO$_4$, filtered and concentrated in vacuo to give the crude product, which was purified via silica gel chromatography, eluting with a gradient of methanol-dichloromethane-0.880 ammonia (10:489:1 to 15:484:1), to give the title compound as a pale yellow oil (77 mg, 47%).

NMR (CD$_3$OD, selected data from the free base): 0.77 (d, 3H), 0.88 (t, 3H), 1.23–1.38 (m, 9H), 1.28 (s, 9H), 1.42–1.61 (m, 3H), 1.97 (m, 1H), 2.20–2.62 (m, 6H), 2.78 (m, 1H), 6.73 (m, 1H), 6.81 (m, 1H) and 7.69 (m, 1H).

MS (APCI$^+$): M/Z [MH$^+$] 389.3; C$_{24}$H$_{40}$N$_2$O$_2$+H requires 389.3.

Example 13

(±)-N-Hexyl-trans-3,4-dimethyl-4-(3-hydroxy-4-methylaminomethylphenyl)piperidine To a stirred solution of (±)-N-hexyl-trans-3,4-dimethyl-4-(4-formyl-3-hydroxyphenyl)piperidine (Example 34, 0.113 g, 0.36 mmol), methylamine (0.195 mL of 2.0 M in methanol, 0.39 mmol) and acetic acid (22.7 μL, 0.39 mmol) in 1,2-dichloroethane (2.5 mL) was added sodium triacetoxyborohydride (0.113 g, 0.53 mmol). After 2.5 hours, the reaction mixture was diluted with aqueous saturated sodium hydrogen-carbonate (25 mL) and extracted with dichloromethane (3×25 mL). The combined extracts were washed with brine (30 mL), dried over Na$_2$SO$_4$, filtered and concentrated in vacuo to give the crude product, which was purified via silica gel chromatography, eluting with a gradient of methanol-dichloromethane-0.880 ammonia (5:494:1 to 5:444:1), to give the title compound as a yellow oil (45 mg).

NMR ($C_6D_6$, selected data from the free base): 0.85 (t, 3H), 1.00 (d, 3H), 1.03–1.31 (m, 6H), 1.26 (s, 3H), 1.40–1.45 (m, 3H), 1.72 (s, 3H), 1.77 (m, 1H), 2.09–2.46 (m, 6H), 2.67 (m, 1H), 3.32 (s, 2H), 6.73 (dd, 1H), 6.80 (d, 1H) and 7.12 (d, 1H).

MS ($APCI^+$): M/Z [$MH^+$] 333.3; $C_{21}H_{36}N_2O+H$ requires 333.3.

Example 14

(±)-N-Hexyl-trans-3,4-dimethyl-4-(4-ethylaminomethyl-3-hydroxyphenyl)piperidine

To a stirred solution of (±)-N-hexyl-trans-3,4-dimethyl-4-(4-formyl-3-hydroxyphenyl)piperidine (Example 34, 0.139 g, 0.44 mmol), ethylamine (0.241 mL of 2.0 M in methanol, 0.48 mmol) and acetic acid (28 µL, 0.48 mmol) in 1,2-dichloroethane (3 mL) was added sodium triacetoxyborohydride (0.139 g, 0.66 mmol). After 2.5 hours, the reaction mixture was diluted with aqueous saturated sodium hydrogen-carbonate (25 mL) and extracted with dichloromethane (3×25 mL). The combined extracts were washed with brine (30 mL), dried over $Na_2SO_4$, filtered and concentrated in vacuo to give the crude product, which was purified via silica gel chromatography, eluting with a gradient of methanol-dichloromethane-0.880 ammonia (5:494:1 to 5:444:1), to give the title compound as a yellow oil (64 mg).

NMR ($C_6D_6$, selected data from the free base): 0.59 (t, 3H), 0.84 (t, 3H), 1.00 (d, 3H), 1.16–1.31 (m, 6H), 1.27 (s, 3H), 1.38–1.45 (m, 3H), 1.86 (m, 1H), 2.04 (q, 2H), 2.10–2.46 (m, 6H), 2.68 (m, 1H), 3.41 (s, 2H), 6.74 (dd, 1H), 6.82 (d, 1H) and 7.12 (d, 1H).

MS ($APCI^+$): M/Z [$MH^+$] 347.3; $C_{22}H_{38}N_2O+H$ requires 347.3.

Example 15

(±)-N-Hexyl-trans-3,4-dimethyl-4-(4-dimethylaminomethyl-3-hydroxyphenyl)piperidine To a stirred solution of (±)-N-hexyl-trans-3,4-dimethyl-4-(4-formyl-3-hydroxyphenyl)piperidine (Example 34, 0.101 g, 0.32 mmol), dimethylamine (0.175 mL of 2.0 M in methanol, 0.35 mmol) and acetic acid (20 µL, 0.35 mmol) in 1,2-dichloroethane (3 mL) was added sodium triacetoxyborohydride (0.101 g, 0.48 mmol). After 2.5 hours, the reaction mixture was diluted with aqueous saturated sodium hydrogen-carbonate (25 mL) and extracted with dichloromethane (3×25 mL). The combined extracts were washed with brine (30 mL), dried over $Na_2SO_4$, filtered and concentrated in vacuo to give the crude product, which was purified via silica gel chromatography, eluting with a gradient of methanol-dichloromethane-0.880 ammonia (5:494:1 to 25:474:1), to give the title compound as a yellow oil (54 mg).

NMR ($C_6D_6$, selected data from the free base): 0.85 (t, 3H), 1.00 (d, 3H), 1.23–1.29 (m, 6H), 1.26 (s, 3H), 1.38–1.44 (m, 3H), 1.71 (s, 6H), 1.86 (m, 1H), 2.12–2.43 (m, 6H), 2.66 (m, 1H), 3.15 (s, 2H), 6.74 (dd, 1H), 6.79 (d, 1H) and 7.15 (d, 1H).

MS ($APCI^+$): M/Z [$MH^+$] 347.3; $C_{22}H_{38}N_2O+H$ requires 347.3.

Example 16

(±)-N-Hexyl-trans-3,4-dimethyl-4-(3-hydroxy-2-methylphenyl)piperidine

A mixture of (±)-N-hexyl-trans-3,4-dimethyl-4-(3-hydroxy-2-methyl-4-trimethylsilylphenyl)piperidine (Preparation 2, 51 mg, 0.11 mmol) and 20% aqueous hydrochloric acid (2.5 mL) was allowed to stir at room temperature for 1 hour. The reaction mixture was diluted with water (10 mL) adjusted to pH 9 with 5N sodium hydroxide and extracted with dichloromethane (3×20 mL). The combined extracts were concentrated in vacuo to give the crude product, which was purified via silica gel chromatography, eluting with a gradient of methanol-dichloromethane-0.880 ammonia (5:494:1 to 15:484:1), to give the title compound as a yellow oil (27 mg).

NMR ($C_6D_6$, selected data from the free base): 0.85 (t, 3H), 0.92 (d, 3H), 1.21 (s, 3H), 1.21–1.29 (m, 6H), 1.37–1.44 (m, 3H), 1.83 (m, 1H), 2.09–2.45 (m, 6H), 2.66 (m, 1H), 3.33 (s, 3H), 6.59 (dd, 1H), 6.82 (d, 1H), 6.95 (s, 1H) and 7.10–7.14 (m, 1H).

MS ($APCI^+$): M/Z [$MH^+$] 304.4; $C_{20}H_{33}NO+H$ requires 304.3.

Example 17

(±)-N-Hexyl-trans-3,4-dimethyl-4-(3-hydroxy-4-methoxycarbonylphenyl)piperidine

To a stirred solution of (±)-N-hexyl-trans-3,4-dimethyl-4-(4-formyl-3-hydroxyphenyl)piperidine (Example 34, 93 mg, 0.29 mmol) and acetic acid (10 µL, 0.18 mmol) in methanol (10 mL) was added sodium cyanide (26 mg, 0.53 mmol) and manganese(IV) oxide (0.291 g, 3.51 mmol). After 36 hours, the reaction mixture was filtered through Celite® with the aid of methanol and concentrated in vacuo to give the crude product, which was purified via silica gel chromatography, eluting with a gradient of methanol-dichloromethane-0.880 ammonia (5:494:1 to 15:484:1), to give the title compound as a yellow oil (42 mg).

NMR ($C_6D_6$, selected data from the free base): 0.84–0.88 (m, 6H), 1.09 (s, 3H), 1.21–1.31 (m, 6H), 1.37–1.42 (m, 3H), 1.70 (m, 1H), 1.99–2.39 (m, 6H), 2.60 (m, 1H), 3.28 (s, 3H), 6.63 (dd, 1H), 7.03 (d, 1H) and 7.72 (d, 1H).

MS ($APCI^+$): M/Z [$MH^+$] 348.3; $C_{22}H_{33}NO_3+H$ requires 348.3.

Example 18

(±)-N-Hexyl-trans-3,4-dimethyl-4-(4-ethoxycarbonyl-3-hydroxyphenyl)piperidine

To a stirred solution of (±)-N-hexyl-trans-3,4-dimethyl-4-(4-formyl-3-hydroxyphenyl)piperidine (Example 34, 93 mg, 0.29 mmol) and acetic acid (10 µL, 0.18 mmol) in ethanol (10 mL) was added sodium cyanide (26 mg, 0.53 mmol) and manganese(IV) oxide (0.291 g, 3.51 mmol). After 36 hours, the reaction mixture was filtered through Celite® with the aid of methanol and concentrated in vacuo to give the crude product, which was purified via silica gel chromatography, eluting with a gradient of methanol-dichloromethane-0.880 ammonia (5:494:1 to 15:484:1), to give the title compound as a yellow oil (48 mg).

NMR ($C_6D_6$, selected data from the free base): 0.84–0.89 (m, 9H), 1.10 (s, 3H), 1.22–1.31 (m, 6H), 1.37–1.44 (m, 3H), 1.70 (m, 1H), 1.99–2.39 (m, 6H), 2.60 (m, 1H), 3.92 (q, 2H), 6.65 (dd, 1H), 7.04 (d, 1H) and 7.77 (d, 1H).

MS ($APCI^+$): M/Z [$MH^+$] 362.3; $C_{22}H_{35}NO_3+H$ requires 362.3.

Example 19

(±)-N-Hexyl-trans-3,4-dimethyl-4-(4-N'-methylaminocarbonyl-3-hydroxyphenyl)piperidine A stirred solution of (±)-N-hexyl-trans-3,4-dimethyl-4-(3-N',N'-diethylcarbamyloxy-4-N"-methylaminocarbonylphenyl)piperidine (Example 53, 0.163 g, 0.37 mmol) in methanol (2.5 mL) was treated with methylamine (5.5 mL of 2.0 M in methanol, 11 mmol). After 24 hours, the reaction mixture was concentrated in vacuo to give the crude product, which was purified via silica gel chromatography, eluting with a gradient of methanol-dichloromethane-0.880 ammonia (5:494:1 to 15:484:1), to give the title compound as a pale yellow oil (28 mg).

NMR ($C_6D_6$, selected data from the free base): 0.86 (t, 3H), 0.91 (d, 3H), 1.15 (s, 3H), 1.25–1.32 (m, 6H), 1.39–1.44 (m, 3H), 1.76 (m, 1H), 2.04–2.40 (m, 9H), 2.64 (m, 1H), 5.31 (br s, 1H), 6.61 (dd, 1H), 6.69 (d, 1H) and 7.07 (d, 1H).

MS (APCI$^+$): M/Z [MH$^+$] 347.3; $C_{21}H_{34}N_2O_2$+H requires 347.3.

Example 20

(±)-N-Hexyl-trans-3,4-dimethyl-4-(4-N',N'-dimethylaminocarbonyl-3-hydroxyphenyl)piperidine To a stirred solution of (±)-N-hexyl-trans-3,4-dimethyl-4-(3-N',N'-dimethylcarbamyloxyphenyl)piperidine (Preparation 5, 0.285 g, 0.71 mmol) and N,N,N',N'-tetramethylethylenediamine (0.118 mL, 0.78 mmol) in tetrahydrofuran (5 mL) at −78° C. was added s-butyllithium (0.6 mL of 1.3 M in cyclohexane, 0.78 mmol) and the reaction mixture was allowed to warm to room temperature overnight. The reaction mixture was diluted with water (25 mL) and extracted with ethyl acetate (3×25 mL). The combined extracts were washed with brine (30 mL), dried over $Na_2SO_4$, filtered and concentrated in vacuo to give the crude product, which was purified via silica gel chromatography, eluting with a gradient of methanol-dichloromethane-0.880 ammonia (10:989:1 to 30:969:1), to give the title compound as a yellow oil (65 mg).

NMR ($C_6D_6$, selected data from the free base): 0.86 (t, 3H), 0.92 (d, 3H), 1.17 (s, 3H), 1.21–1.34 (m, 7H), 1.42 (m, 2H), 1.78 (m, 1H), 2.05–2.33 (m, 6H), 2.43 (s, 6H), 2.64 (m, 1H), 6.61 (dd, 1H), 6.96 (m, 1H) and 7.13 (m, 1H).

MS (APCI$^+$): M/Z [MH$^+$] 361.3; $C_{24}H_{36}N_2O_2$+H requires 361.3.

Example 21

(±)-N-Hexyl-trans-3,4-dimethyl-4-(4-N',N'-diethylaminocarbonyl-3-hydroxyphenyl)piperidine To a stirred solution of (±)-N-hexyl-trans-3,4-dimethyl-4-(3-N',N'-diethylcarbamyloxyphenyl)piperidine (Preparation 4, 0.109 g, 0.28 mmol) and N,N,N',N'-tetramethylethylenediamine (47 μL, 0.31 mmol) in tetrahydrofuran (5 mL) at −78° C. was added s-butyllithium (0.238 mL of 1.3 M in cyclohexane, 0.31 mmol) and the reaction mixture was allowed to warm to room temperature overnight. The reaction mixture was diluted with water (25 mL) and extracted with ethyl acetate (3×25 mL). The combined extracts were washed with brine (30 mL), dried over $Na_2SO_4$, filtered and concentrated in vacuo to give the crude product, which was purified via silica gel chromatography, eluting with a gradient of methanol-dichloromethane-0.880 ammonia (10:989:1 to 30:969:1), to give the title compound as a yellow oil (38 mg).

NMR ($C_6D_6$, selected data from the free base): 0.80 (t, 6H), 0.86 (t, 3H), 0.93 (d, 3H), 1.18 (s, 3H), 1.24–1.34 (m, 7H), 1.41 (m, 2H), 1.77 (m, 1H), 2.05–2.43 (m, 6H), 2.65 (m, 1H), 3.00 (q, 4H), 6.62 (dd, 1H), 7.06 (d, 1H) and 7.16 (d, 1H).

MS (APCI$^+$): M/Z [MH$^+$] 389.3; $C_{24}H_{40}N_2O_2$+H requires 389.3.

Example 22

(±)-N-Hexyl-trans-3,4-dimethyl-4-(3-hydroxy-4-propionylaminophenyl)piperidine

To a stirred solution of (±)-N-hexyl-trans-3,4-dimethyl-4-(3-hydroxy-4-aminophenyl)piperidine (Example 4, 0.185 g, 0.61 mmol) and pyridine (0.108 mL, 1.28 mmol) in tetrahydrofuran (8 mL) at 0° C. was added propionyl chloride (0.109 mL, 1.25 mmol) and the reaction mixture was allowed to warm to room temperature overnight. The reaction mixture was then cooled again to 0° C. and additional pyridine (54 μL, 0.64 mmol) and propionyl chloride (25 μL, 0.31 mmol) were introduced. After an additional 4 hours, the reaction mixture was diluted with aqueous saturated sodium hydrogencarbonate (10 mL) and extracted with dichloromethane (3×10 mL). The combined extracts were washed with brine (20 mL), dried over $Na_2SO_4$, filtered and concentrated in vacuo to give the crude product, which was purified via silica gel chromatography, eluting with a gradient of methanol-dichloromethane-0.880 ammonia (10:989:1 to 30:967:3), to give the title compound as a pale yellow oil (38 mg).

NMR ($C_6D_6$, selected data from the free base): 0.84–0.90 (m, 6H), 0.93 (d, 3H), 1.22 (s, 3H), 1.22–1.29 (m, 6H), 1.39–1.46 (m, 3H), 1.75 (q, 2H), 1.81 (m, 1H), 2.11–2.47 (m, 6H), 2.69 (m, 1H), 6.72 (dd, 1H), 7.12–7.17 (m, 2H) and 7.38 (m, 1H).

MS (APCI$^+$): M/Z [MH$^+$] 361.4; $C_{22}H_{36}N_2O_2$+H requires 361.3.

Example 23

(±)-N-Hexyl-trans-3,4-dimethyl-4-(4-N',N'-dimethylaminocarbonylamino-3-hydroxyphenyl)piperidine To a stirred solution of (±)-N-hexyl-trans-3,4-dimethyl-4-(4-amino-3-hydroxyphenyl)piperidine (Example 4, 0.189 g, 0.62 mmol) in pyridine (5 mL) at 0° C. was added dimethylcarbamyl chloride (0.12 mL, 1.3 mmol) and the reaction mixture was allowed to warm to room temperature overnight. The reaction mixture was diluted with aqueous saturated sodium hydrogencarbonate (10 mL) and extracted with dichloromethane (3×10 mL). The combined extracts were washed with brine (20 mL), dried over $Na_2SO_4$, filtered and concentrated in vacuo to give the crude product, which was purified via silica gel chromatography, eluting with a gradient of methanol-dichloromethane-0.880 ammonia (10:989:1 to 40:969:1), to give the title compound as a pale yellow oil (52 mg).

NMR ($C_6D_6$, selected data from the free base): 0.85 (t, 3H), 0.97 (d, 3H), 1.22 (s, 3H), 1.22–1.25 (m, 6H), 1.38–1.41 (m, 3H), 1.80 (m, 1H), 2.11–2.43 (m, 6H), 2.48 (s, 3H), 2.54 (s, 3H), 2.65 (m, 1H), 3.18 (s, 1H), 6.46 (m, 1H), 6.86 (m, 1H) and 7.15 (m, 1H).

MS (APCI$^+$): M/Z [MH$^+$] 376.3; $C_{22}H_{37}N_3O_2$+H requires 376.3.

Example 24

(±)-N-Hexyl-trans-3,4-dimethyl-4-(3-hydroxy-4-N'-methylaminocarbonylaminophenyl)piperidine To a stirred solution of (±)-N-hexyl-trans-3,4-dimethyl-4-(4-amino-3-hydroxyphenyl)piperidine (Example 4, 0.283 g, 0.93 mmol) and pyridine (0.23 mL, 2.9 mmol) in tetrahydrofuran (8 mL) at 0° C. was added methyl isocyanate (58 µL, 0.98 mmol) and the reaction mixture was allowed to warm to room temperature overnight. The reaction mixture was diluted with aqueous saturated sodium hydrogencarbonate (10 mL) and extracted with dichloromethane (3×10 mL). The combined extracts were washed with brine (20 mL), dried over $Na_2SO_4$, filtered and concentrated in vacuo to give the crude product, which was purified via silica gel chromatography, eluting with a gradient of ethyl acetate-dichloromethane (10:90 to 60:40), to give the title compound as a pale yellow oil (28 mg).

NMR ($C_6D_6$, selected data from the free base): 0.87 (t, 3H), 0.93 (d, 3H), 1.24 (s, 3H), 1.24–1.31 (m, 6H), 1.42–1.51 (m, 3H), 1.87 (m, 1H), 2.24–2.51 (m, 6H), 2.46 (s, 3H), 2.74 (m, 1H), 5.69 (br s, 1H), 6.70 (m, 1H), 7.10–7.12 (m, 1H), 7.32 (m, 1H) and 7.74 (br s, 1H).

MS ($APCI^+$): M/Z [$MH^+$] 362.3; $C_{21}H_{35}N_3O_2$+H requires 362.3.

Example 25

(±)-N-Hexyl-trans-3,4-dimethyl-4-(3-hydroxy-4-methoxycarbonylaminophenyl)piperidine To a stirred solution of (±)-N-hexyl-trans-3,4-dimethyl-4-(4-amino-3-hydroxyphenyl)piperidine (Example 4, 0.183 g, 0.60 mmol) in tetrahydrofuran (10 mL) was added methyl chloroformate (50 µL, 0.66 mmol). After 6 hours, the reaction mixture was diluted with water (20 mL) and extracted with ethyl acetate (3×20 mL). The combined extracts were washed with brine (20 mL), dried over $Na_2SO_4$, filtered and concentrated in vacuo to give the crude product, which was purified via silica gel chromatography, eluting with a gradient of ethyl acetate-dichloromethane-0.880 ammonia (150:349:1 to 200:299:1), to give the title compound as a pale yellow oil (44 mg).

NMR ($C_6D_6$, selected data from the free base): 0.83–0.86 (m, 6H), 1.17 (s, 3H), 1.21–1.34 (m, 6H), 1.37–1.45 (m, 3H), 1.74 (m, 1H), 2.08–2.43 (m, 6H), 2.70 (m, 1H), 3.25 (s, 3H), 6.66 (m, 1H), 6.77 (br s, 1H), 6.93 (s, 1H) and 7.45 (m, 1H).

MS ($APCI^+$): M/Z [$MH^+$] 363.4; $C_{21}H_{34}N_2O_3$+H requires 363.3.

Example 26

(±)-N-Hexyl-trans-3,4-dimethyl-4-(4-formylamino-3-aminophenyl)piperidine

To a stirred solution of formic acid (26 µL, 0.69 mmol) and acetyl chloride (49 µL, 0.69 mmol) in tetrahydrofuran (5 mL) at 0° C. was added pyridine (55 µL, 0.69 mmol). After 0.5 hours, a solution of (±)-N-hexyl-trans-3,4-dimethyl-4-(4-amino-3-hydroxyphenyl)piperidine (Example 4, 0.200 g, 0.66 mmol) and pyridine (55 µL, 0.69 mmol) in tetrahydrofuran (5 mL) was added to the reaction vessel. After a further 4 hours, the reaction mixture was diluted with aqueous saturated sodium hydrogen-carbonate (20 mL) and extracted with dichloromethane (3×20 mL). The combined extracts were washed with brine (20 mL), dried over $Na_2SO_4$, filtered and concentrated in vacuo to give the crude product, which was purified via silica gel chromatography, eluting with ethyl acetate-dichloromethane-0.880 ammonia (150:349:12), to give the title compound as a pale yellow oil (22 mg).

NMR ($C_6D_6$, selected data from the free base): 0.82–0.88 (m, 6H), 1.16 (s, 3H), 1.21–1.33 (m, 6H), 1.36–1.42 (m, 3H), 1.76 (m, 1H), 2.10–2.45 (m, 6H), 2.68 (m, 1H), 6.65 (m, 1H), 7.06–7.10 (m, 1H), 7.21 (m, 1H), 7.55 (s, 1H) and 8.46 (br s, 1H).

MS ($APCI^+$): M/Z [$MH^+$] 333.4; $C_{20}H_{32}N_2O_2$+H requires 333.3.

Example 27

(±)-N-Hexyl-trans-3,4-dimethyl-4-(4-N',N'-dimethylaminosulfonylamino-3-hydroxyphenyl)piperidine To a stirred solution of (±)-N-hexyl-trans-3,4-dimethyl-4-(3-hydroxy-4-aminophenyl)piperidine (Example 4, 0.194 g, 0.64 mmol) and pyridine (0.108 mL, 1.34 mmol) in tetrahydrofuran (10 mL) was added dimethylsulfamyl chloride (0.144 mL, 1.34 mmol). The reaction was then heated to reflux overnight. Upon cooling, the reaction mixture was diluted with aqueous saturated sodium hydrogencarbonate (20 mL) and extracted with dichloromethane (3×20 mL). The combined extracts were washed with brine (20 mL), dried over $Na_2SO_4$, filtered and concentrated in vacuo to give the crude product, which was purified via silica gel chromatography, eluting with a gradient of ethyl acetate-dichloromethane-0.880 ammonia (150:349:1 to 200:299:1), to give the title compound as a pale yellow oil (77 mg).

NMR ($C_6D_6$, selected data from the free base): 0.81 (d, 3H), 0.87 (t, 3H), 1.18 (s, 3H), 1.23–1.27 (m, 6H), 1.38–1.49 (m, 3H), 1.80 (m, 1H), 2.18–2.44 (m, 6H), 2.51 (s, 6H), 2.83 (m, 1H), 6.62 (m, 1H), 6.97 (s, 1H), 7.56 (d, 1H) and 7.82 (br s, 1H).

MS ($APCI^+$): M/Z [$MH^+$] 412.2; $C_{21}H_{37}N_3O_3S$+H requires 412.3.

Example 28

(±)-N-Hexyl-trans-3,4-dimethyl-4-(3-hydroxy-4-pentanoylaminophenyl)piperidine

To a stirred solution of (±)-N-hexyl-trans-3,4-dimethyl-4-(3-hydroxy-4-aminophenyl)piperidine (Example 4, 0.155 g, 0.51 mmol) and pyridine (43 µL, 0.53 mmol) in tetrahydrofuran (5 mL) at 0° C. was added valeryl chloride (63 µL, 0.53 mmol). After 2 hours, the reaction mixture was diluted with aqueous saturated sodium hydrogencarbonate (10 mL) and extracted with dichloromethane (3×10 mL). The combined extracts were washed with brine (20 mL), dried over $Na_2SO_4$, filtered and concentrated in vacuo to give the crude product, which was purified via silica gel chromatography, eluting with a gradient of methanol-dichloromethane-0.880 ammonia (10:989:1 to 30:967:3), to give the title compound as a pale yellow oil (96 mg).

NMR ($C_6D_6$, selected data from the free base): 0.72 (t, 3H), 0.85 (t, 3H), 0.93 (d, 3H), 1.07–1.16 (m, 2H), 1.22 (s, 3H), 1.22–1.25 (m, 6H), 1.42–1.50 (m, 5H), 1.83 (m, 1H), 1.90–1.94 (m, 2H), 2.14–2.48 (m, 6H), 2.71 (m, 1H), 6.73 (dd, 1H), 7.10–7.12 (m, 1H), 7.46 (d, 1H) and 7.98 (s, 1H).

MS ($APCI^+$): M/Z [$MH^+$] 389.3; $C_{24}H_{40}N_2O_2$+H requires 389.3.

Example 29

(±)-N-Hexyl-trans-3,4-dimethyl-4-(2,4-dichloro-3-hydroxyphenyl)piperidine

To a solution of (±)-N-hexyl-trans-3,4-dimethyl-4-(3-hydroxyphenyl)piperidine (Preparation 7, 662 mg, 2.28 mmol) in acetic acid (20 mL) was added dropwise a solution of chlorine (324 mg, 4.56 mmol) in acetic acid (6 mL). The reaction was monitored by mass spectrometry for the formation of the title compound, as well as for the loss of starting material and monochlorinated product. The acetic acid was then removed in vacuo and the residue washed with saturated sodium hydrogencarbonate solution then extracted with dichloromethane. The solvent was removed in vacuo and the residue purified by preparative silica thin layer chromatography eluting with hexane-ethyl acetate (2:1) to give the title compound (150 mg) from the faster running band.

NMR (CDCl$_3$, selected data from the free base): 0.77 (d, 3H), 0.88 (t, 3H), 1.28 (s, 3H), 6.83 (d, 1H) and 7.20 (d, 1H).

MS (APCI$^+$): M/Z [MH$^+$] 358.4; $C_{19}H_{29}Cl_2NO+H$ requires 358.2.

Example 30

(±)-N-Hexyl-trans-3,4-dimethyl-4-[3-hydroxy-4-(2-methylpropionylamino)phenyl]piperidine To a stirred solution of (±)-N-hexyl-trans-3,4-dimethyl-4-(3-hydroxy-4-aminophenyl)piperidine (Example 4, 0.188 g, 0.62 mmol) and pyridine (52 μL, 0.65 mmol) in tetrahydrofuran (10 mL) at 0° C. was added isobutyryl chloride (68 μL, 0.65 mmol). After 1.5 hours, the reaction mixture was diluted with aqueous saturated sodium hydrogencarbonate (10 mL) and extracted with dichloromethane (3×10 mL). The combined extracts were washed with brine (20 mL), dried over Na$_2$SO$_4$, filtered and concentrated in vacuo to give the crude product, which was purified via silica gel chromatography, eluting with a gradient of methanol-dichloromethane-0.880 ammonia (10:989:1 to 30:967:3), to give the title compound as a pale yellow oil (0.112 g).

NMR (C$_6$D$_6$, selected data from the free base): 0.85 (t, 3H), 0.91 (d, 3H), 0.95 (d, 6H), 1.21 (s, 3H), 1.21–1.27 (m, 6H), 1.40–1.45 (m, 3H), 1.81 (m, 1H), 2.02 (m, 1H), 2.12–2.46 (m, 6H), 2.70 (m, 1H), 6.70 (dd, 1H), 7.09–7.10 (m, 1H), 7.43 (d, 1H) and 7.81 (s, 1H).

MS (APCI$^+$): M/Z [MH$^+$] 375.3; $C_{23}H_{38}N_2O_2+H$ requires 375.3.

Example 31

(±)-N-Hexyl-trans-3,4-dimethyl-4-[3-hydroxy-4-(2-methylbutanoyl)phenyl]piperidine To a stirred solution of (±)-N-hexyl-trans-3,4-dimethyl-4-(3-hydroxy-4-aminophenyl)piperidine (Example 4, 0.183 g, 0.60 mmol) and pyridine (51 μL, 0.63 mmol) in tetrahydrofuran (5 mL) at 0° C. was added isovaleryl chloride (77 μL, 0.63 mmol). After 2.5 hours, the reaction mixture was diluted with aqueous saturated sodium hydrogencarbonate (10 mL) and extracted with dichloromethane (3×15 mL). The combined extracts were washed with aqueous saturated sodium hydrogencarbonate (10 mL) and brine (15 mL), dried over Na$_2$SO$_4$, filtered and concentrated in vacuo to give the crude product, which was purified via silica gel chromatography, eluting with methanol-dichloromethane-0.880 ammonia (10:489:1), to give the title compound as a pale yellow oil (0.100 g).

NMR (C$_6$D$_6$, selected data from the free base): 0.76 (d, 6H), 0.85 (t, 3H), 0.92 (d, 3H), 1.22 (s, 3H), 1.22–1.28 (m, 6H), 1.40–1.46 (m, 3H), 1.79–1.83 (m, 3H), 2.02–2.09 (m, 1H), 2.13–2.47 (m, 6H), 2.70 (m, 1H), 6.72 (dd, 1H), 7.09–7.11 (m, 1H), 7.46 (d, 1H) and 7.94 (s, 1H).

MS (APCI$^+$): M/Z [MH$^+$] 389.4; $C_{24}H_{40}N_2O_2+H$ requires 389.3.

Example 32

(±)-N-Hexyl-trans-3,4-dimethyl-4-(3-hydroxy-4-butanoylaminophenyl)piperidine

To a stirred solution of (±)-N-hexyl-trans-3,4-dimethyl-4-(3-hydroxy-4-aminophenyl)piperidine (Example 4, 0.188 g, 0.62 mmol) and pyridine (52 μL, 0.65 mmol) in tetrahydrofuran (10 mL) at 0° C. was added butyryl chloride (67 μL, 0.65 mmol). After 2.5 hours, the reaction mixture was diluted with aqueous saturated sodium hydrogencarbonate (10 mL) and extracted with dichloromethane (3×15 mL). The combined extracts were washed with aqueous saturated sodium hydrogencarbonate (10 mL) and brine (15 mL), dried over Na$_2$SO$_4$, filtered and concentrated in vacuo to give the crude product, which was purified via silica gel chromatography, eluting with a gradient of methanol-dichloromethane-0.880 ammonia (10:489:1 to 15:484:1), to give the title compound as a pale yellow oil (0.104 g).

NMR (C$_6$D$_6$, selected data from the free base): 0.68 (t, 3H), 0.85 (t, 3H), 0.93 (d, 3H), 1.21 (s, 3H), 1.23–1.30 (m, 6H), 1.37–1.47 (m, 5H), 1.68–1.72 (m, 2H), 1.80 (m, 1H), 2.10–2.46 (m, 6H), 2.68 (m, 1H), 6.72 (dd, 1H), 7.04 (d, 1H) and 7.09–7.20 (m, 2H).

MS (APCI$^+$): M/Z [MH$^+$] 375.3; $C_{23}H_{38}N_2O_2+H$ requires 375.3.

Example 33

(±)-N-Hexyl-trans-3,4-dimethyl-4-(3-hydroxy-4-methanesulfonylaminophenyl)piperidine To a stirred solution of (±)-N-hexyl-trans-3,4-dimethyl-4-(3-hydroxy-4-aminophenyl)piperidine (Example 4, 0.129 g, 0.42 mmol) and pyridine (38 μL, 0.47 mmol) in dichloromethane (5 mL) at 0° C. was added methanesulfonyl chloride (34 μL, 0.45 mmol). Additional methane-sulfonyl chloride was introduced at 0.5 hours (12 μL, 0.16 mmol), 1 hour (12 μL, 0.16 mmol), 3 hours (10 μL, 0.13 mmol) and 4 hours (6 μL, 8 μmol) and the reaction was allowed to warm to room temperature while stirring overnight. The reaction mixture was diluted with aqueous saturated sodium hydrogencarbonate (10 mL) and extracted with dichloromethane (3×10 mL). The combined extracts were washed with brine (20 mL), dried over Na$_2$SO$_4$, filtered and concentrated in vacuo to give the crude product, which was purified via silica gel chromatography, eluting with a gradient of methanol-dichloromethane-0.880 ammonia (10:489:1 to 15:484:1), to give the title compound as a brown solid (11 mg).

NMR (C$_6$D$_6$, selected data from the free base): 0.82 (d, 3H), 0.87 (t, 3H), 1.23 (s, 3H), 1.26–1.28 (m, 6H), 1.44–1.49 (m, 3H), 1.78 (m, 1H), 2.15–2.52 (m, 6H), 2.44 (s, 3H), 2.81 (m, 1H), 6.38 (br s, 2H), 6.63 (m, 1H), 6.98 (m, 1H) and 7.39 (m, 1H).

MS (APCI$^+$): M/Z [MH$^+$] 383.2; $C_{20}H_{34}N_2O_3S+H$ requires 383.2.

Example 34

(±)-N-Hexyl-trans-3,4-dimethyl-4-(4-formyl-3-hydroxy-phenyl)piperidine

To a stirred solution of (±)-N-hexyl-trans-3,4-dimethyl-4-(3-N',N'-diethylcarbamyloxyphenyl)piperidine (Preparation 4, 0.495 g, 1.27 mmol) and N,N,N',N'-tetramethylethylenediamine (0.231 mL, 1.53 mmol) in tetrahydrofuran (5 mL) at −78° C. was added s-butyllithium (1.18 mL of 1.3 M in cyclohexane, 1.53 mmol). After 1 hour, DMF (0.493 mL, 6.37 mmol) was added and the reaction mixture was allowed to warm to room temperature overnight. The reaction mixture was diluted with aqueous saturated sodium hydrogencarbonate (25 mL) and extracted with dichloromethane (3×30 mL). The combined extracts were washed with brine (15 mL), dried over $Na_2SO_4$, filtered and concentrated in vacuo to give the crude product, which was purified via silica gel chromatography, eluting with a gradient of methanol-dichloromethane-0.880 ammonia (2:197:1 to 4:195:1), to give the title compound as a pale yellow oil (0.308 g).

NMR ($C_6D_6$, selected data from the free base): 0.79 (d, 3H), 0.86 (t, 3H), 1.04 (s, 3H), 1.16–1.33 (m, 6H), 1.38–1.42 (m, 3H), 1.66 (m, 1H), 1.99–2.39 (m, 6H), 2.59 (m, 1H), 6.57 (dd, 1H), 6.78 (d, 1H), 6.88 (d, 1H) and 9.25 (s, 1H).

MS ($APCI^+$): M/Z [$MH^+$] 318.2; $C_{20}H_{31}NO_2$+H requires 318.2.

Example 35

(±)-N-Hexyl-trans-3,4-dimethyl-4-(3-hydroxy-2,4,6-trichlorophenyl)piperidine

To a solution of (±)-N-hexyl-trans-3,4-dimethyl-4-(3-hydroxyphenyl)piperidine (Preparation 7, 100 mg, 0.345 mmol) in acetic acid (2 mL) was added dropwise a solution of chlorine (98 mg, 1.38 mmol) in acetic acid (1 mL). The reaction was monitored by mass spectrometry for the formation of the title compound. The acetic acid was then removed in vacuo and the residue washed with saturated sodium hydrogencarbonate solution, which solution was then extracted with dichloromethane. The dichloromethane was removed in vacuo and the residue was chromatographed on Merck 230–400 mesh silica gel, eluting with ethyl acetate-hexane (1:25), to give the title compound (18 mg).

NMR ($CDCl_3$, selected data from the free base): 0.80 (d, 3H), 0.88 (t, 3H), 1.29 (s, 3H) and 7.15 (s, 1H).

MS ($APCI^+$): M/Z [$MH^+$] 392.1; $C_{19}H_{28}Cl_3NO$+H requires 392.1.

Example 36

(±)-N-Hexyl-trans-3,4-dimethyl-4-(3-aminosulfonyl-3-hydroxyphenyl)piperidine

A solution of (±)-N-hexyl-trans-3,4-dimethyl-4-(3-N',N'-diethylcarbamyl-oxyphenyl)piperidine (Preparation 4, 200 mg, 0.51 mmol) in chlorosulfonic acid (0.5 mL) was cooled to 0° C. before thionyl chloride (0.2 mL) was added and the reaction mixture stirred at room temperature overnight. To the reaction mixture was added a mixture of ice and water (50:50, 10 mL), and the resulting cream precipitate was filtered off and dried under vacuum. This crude intermediate (0.10 g, 0.20 mmol) was dissolved in methylamine (5 mL of 2 M in tetrahydrofuran, excess) and the reaction mixture was stirred overnight. The solvents were removed in vacuo and the residue was chromatographed on silica gel, eluting with methanol and dichloromethane (5:95), to give the product as a white powder (25 mg).

NMR (DMSO, selected data from the free base): 0.7 (d, 3H), 0.85 (t, 3H), 1.2–1.4 (m, 10H), 2.45 (s, 3H), 6.6 (s, 1H), 6.75 (d, 1H), 7.4 (d, 1H) and 10.5 (s, 1H).

MS (ES+): M/Z [$MH^+$] 383.3; $C_{20}H_{34}N_2O_3S$+H requires 383.2.

Example 37

(±)-N-Hexyl-trans-3,4-dimethyl-4-(4,6-dichloro-3-hydroxyphenyl)piperidine

Isolation of the slowest running compound from Example 29 followed by preparative silica thin layer chromatography, eluting with hexane-ethyl acetate (2:1), gave the title compound (56 mg).

NMR ($CDCl_3$, selected data from the free base): 0.75 (d, 3H), 0.91 (t, 3H), 1.32 (s, 3H), 6.95 (s, 1H) and 7.28 (s, 1H).

MS ($APCI^+$): M/Z [$MH^+$] 358.3; $C_{19}H_{29}Cl_2NO$+H requires 358.2.

Example 38

(±)-N-Hexyl-trans-3,4-dimethyl-4-(3-hydroxy-4-N'-isopropylaminocarbonylphenyl)piperidine A solution of (±)-N-hexyl-trans-3,4-dimethyl-4-(3-hydroxy-4-methoxy-carbonylphenyl)piperidine (Example 17, 20 mg, 0.055 mmol) in isopropylamine (5 mL) was heated at 100° C. overnight in a Wheaton vial. The solution was then cooled and evaporated to dryness in vacuo to yield the desired product (20 mg) as a colourless oil.

NMR ($CDCl_3$, selected data from the free base): 0.95 (d, 3H), 1.30 (d, 6H), 1.33 (s, 3H), 4.28 (m, 1H), 6.22 (br s, 1H), 6.75 (d, 1H), 6.85 (s, 1H) and 7.35 (d, 1H).

MS ($CI^+$): M/Z [$MH^+$] 375.3; $C_{23}H_{38}N_2O_2$+H requires 375.6.

Example 39

(±)-N-Hexyl-trans-3,4-dimethyl-4-(4-chloro-3-hydroxy-phenyl)piperidine

Isolation of a slower running compound from Example 29 followed by preparative HPLC, eluting with 0.05 M aqueous ammonium acetate-methanol (3:7), gave the title compound (10 mg) as its acetate salt.

NMR ($CDCl_3$, selected data from the free base): 0.88 (d, 3H), 0.92 (t, 3H), 1.31 (s, 3H), 6.77 (d, 1H), 6.97 (s, 1H) and 7.23 (d, 1H).

MS ($APCI^+$): M/Z [$MH^+$] 324.0; $C_{19}H_{30}ClNO$+H requires 324.2.

Example 40

(±)-N-Hexyl-trans-3,4-dimethyl-4-(6-chloro-3-hydroxy-phenyl)piperidine

To a solution of (±)-N-hexyl-trans-3,4-dimethyl-4-(3-triisopropylsilyl-oxyphenyl)piperidine (Preparation 3, 151.8 mg, 0.340 mmol) in acetic acid (2 mL) was added dropwise a solution of chlorine (36 mg, 0.510 mmol) in acetic acid (0.5 mL). The reaction was monitored by mass spectrometry for the loss of starting material, the acetic acid was then removed in vacuo and the residue washed with saturated sodium hydrogencarbonate solution then extracted with dichloromethane. The dichloromethane was removed in vacuo, the residue dissolved in tetrahydrofuran (3 mL) and stirred overnight with tetrabutylammonium fluoride solution (0.66 mL of 1 M in tetrahydrofuran, 0.66 mmol).The reaction mixture was washed with saturated sodium hydrogencarbonate solution, the solvents removed in vacuo, and the solid mixture of monochlorophenols purified by preparative HPLC on a Beckmann Ultrasphere™ column, 250 mm×10 mm; Flow 20 mL min$^{-1}$; employing UV detection at 220 nm; eluant methanol-0.05 M aqueous ammonium acetate (30:70) to give the title compound (6 mg) as its acetate salt.

NMR ($CDCl_3$, selected data from the free base): 0.84 (d, 3H), 0.91 (t, 3H), 1.28 (s, 3H), 6.67 (d, 1H), 6.90 (s, 1H) and 7.13 (d, 1H).

MS ($APCI^+$): M/Z [$MH^+$] 323.9; $C_{19}H_{30}ClNO$+H requires 324.2.

Example 41

(±)-N-Hexyl-trans-3,4-dimethyl-4-(4aminocarbonyl-3-hydroxyphenyl)piperidine

A solution of (±)-N-hexyl-trans-3,4-dimethyl-4-(3-hydroxy-4-methoxy-carbonylphenyl)piperidine (Example 17, 40 mg, 0.11 mmol) in ammoniacal 1,4-dioxan (4 mL of 0.5 M $NH_3$, 2.0 mmol). The solution was heated at 100° C. overnight in a Wheaton vial. The solution was then cooled, evaporated to dryness in vacuo and the crude residue was chromatographed on Merck 230–400 mesh silica gel (10 g), using hexane-ethyl acetate (1:1) as eluant, to yield an oil (30 mg). This oil was dissolved in dichloromethane (5 mL) and extracted into 2N hydrochloric acid (5 mL). The aqueous phase was then evaporated to dryness in vacuo to yield the desired product (10 mg) as an oil.

NMR ($CD_3OD$, selected data from the free base): 0.85 (d, 3H), 1.33 (s, 3H), 6.82 (d, 1H), 6.85 (s, 1H) and 7.75 (d, 1H).

MS ($CI^+$): M/Z [$MH^+$] 333.5; $C_{20}H_{32}N_2O_2$+H requires 333.5.

Example 42

(±)-N-Hexyl-trans-3,4-dimethyl-4-(4-fluoro-3-hydroxy-phenyl)piperidine

To a stirred solution of (±)-N-hexyl-trans-3,4-dimethyl-4-(3-N',N'-diethylthiocarbamyloxy-4-fluorophenyl)piperidine (Example 54, 35 mg, 0.08 mmol) in tetrahydrofuran (2.5 mL) at 0° C. was added lithium triethylborohydride (0.82 mL of 1.0 M in tetrahydrofuran, 0.82 mmol) and the reaction mixture was allowed to warm to room temperature. After 72, 96 and 120 hours, additional lithium triethylborohydride (1.6 mL of 1.0 M in tetrahydrofuran, 1.6 mmol) was introduced and stirring was continued at reflux. After an additional 24 hours, the reaction mixture was diluted with water (20 mL) and extracted with dichloromethane (3×20 mL). The combined extracts were dried over $Na_2SO_4$, filtered and concentrated in vacuo to give the crude product, which was purified via silica gel chromatography, eluting with a gradient of methanol-dichloromethane-0.880 ammonia (10:989:1 to 50:949:1), to give the title compound as a pale yellow oil (13 mg).

NMR ($C_6D_6$, selected data from the free base): 0.83–0.86 (m, 6H), 1.10 (s, 3H), 1.18–1.24 (m, 6H), 1.42–1.46 (m, 3H), 1.70 (m, 1H), 2.07–2.44 (m, 6H), 2.67 (m, 1H), 6.44 (m, 1H), 6.80 (m, 1H) and 6.93 (m, 1H).

MS ($APCI^+$): M/Z [$MH^+$] 308.3; $C_{19}H_{30}FNO$+H requires 308.2.

Example 43

(±)-N-Hexyl-trans-3,4-dimethyl-4-(2-fluoro-3-hydroxy-phenyl)piperidine

To a solution of (±)-N-hexyl-trans-3,4-dimethyl-4-(3-hydroxyphenyl)piperidine (Preparation 7, 100 mg, 0.26 mmol) in dichloromethane (5 mL) at room temperature was added 3,5-dichloro-1-fluoropyridinium triflate (481 mg, 1.54 mmol). The mixture was heated at reflux for 3 hours and then cooled to room temperature. The solution was poured onto water (5 mL) and the two layers were separated. The aqueous layer was extracted with dichloromethane (3×5 mL) and the combined organics were dried over $MgSO_4$, filtered and concentrated in vacuo to give the crude product. This was chromatographed on Merck 230–400 mesh silica gel, eluting with hexane-ethyl acetate (4:1), to give the title compound (10 mg) as a colourless oil.

1H-NMR ($CDCl_3$) (selected data from free base): 0.90 (m, 3H), 0.96 (d, 3H), 1.20–1.36 (m, 7H), 1.38 (s, 3H), 1.40–1.50 (m, 2H), 2.10–2.53 (m, 7H), 2.70 (m, 1H), 6.54 (td, 1H), 6.67 (td, 1H) and 6.77 (td, 1H).

MS ($TSI^+$): M/Z [$MH^+$] 308.0; $C_{19}H_{30}FNO$+H requires 308.2.

Example 44

(±)-N-3-Cyclohexylpropyl-trans-3,4-dimethyl-4-(3-hydroxy-4-nitrophenyl)piperidine To a stirred solution of (±)-N-(3-cyclohexylpropyl)-trans-3,4-dimethyl-4-(3-hydroxyphenyl)piperidine (Preparation 8, 0.997 g, 3.02 mmol) in acetonitrile (9 mL) and dichloromethane (1 mL) at 0° C. was added nitronium tetrafluoroborate (0.341 g, 3.02 mmol) and the reaction mixture was allowed to warm to room temperature. After 2 hours, the reaction mixture was diluted with aqueous saturated sodium hydrogencarbonate (30 mL) and extracted with dichloromethane (3×30 mL). The combined extracts were washed with brine (30 mL), dried over $Na_2SO_4$ and concentrated in vacuo to give the crude product, which was purified via silica gel chromatography, eluting with ethyl acetate-dichloromethane-0.880 ammonia (300:699:1), to give the title compound as a yellow oil (0.213 g).

NMR ($C_6D_6$, selected data from the free base): 0.78 (d, 3H), 0.78–0.87 (m, 2H), 1.07–1.23 (m, 6H), 1.28 (s, 3H), 1.41–1.47 (m, 2H), 1.59–1.67 (m, 6H), 2.01 (m, 1H), 2.23–2.39 (m, 4H), 2.48–2.61 (m, 2H), 2.83 (m, 1H), 6.92 (dd, 1H), 7.01 (d, 1H) and 8.00 (d, 1H).

MS ($APCI^+$): M/Z [$MH^+$] 375.3; $C_{22}H_{34}N_2O_3$+H requires 375.3.

Example 45

(±)-N-(3-Cyclohexylpropyl)-trans-3,4-dimethyl4-(4-amino-3-hydroxyphenyl)piperidine To a solution of (±)-N-(3-cyclohexylpropyl)-trans-3,4-dimethyl-4-(3-hydroxy-4-nitrophenyl)piperidine (Example 44, 0.213 g, 0.57 mmol) in tetrahydrofuran (4 mL) was added platinum(IV) oxide (2 mg, 0.57 mmol) and the reaction mixture was shaken under 345 kPa of hydrogen gas for 14 hours. The reaction mixture was purged with nitrogen, filtered under nitrogen and the air-sensitive product was employed without further purification.

MS ($APCI^+$): M/Z [$MH^+$] 345.2; $C_{22}H_{36}N_2O$+H requires 345.3.

Example 46

(±)-N-(3-Cyclohexylpropyl)-trans-3,4-dimethyl-4-(3-hydroxy-4-acetylaminophenyl)piperidine To a stirred solution of (±)-N-(3-cyclohexylpropyl)-trans-3,4-dimethyl-4-(4-amino-3-hydroxyphenyl)piperidine (Example 45, 0.106 g, 0.30 mmol) and pyridine (27 μL, 0.33 mmol) in tetrahydrofuran (7 mL) at 0° C. was added acetyl chloride (45 μL, 0.63 mmol). After 1.5 hours, the reaction mixture was diluted with aqueous saturated sodium hydrogencarbonate (10 mL) and extracted with dichloromethane (3×10 mL). The combined extracts were washed with brine (20 mL), dried over $Na_2SO_4$, filtered and concentrated in vacuo to give a residue which was dissolved in methanol (10 mL) and allowed to stir for 18 hours. The reaction mixture was concentrated in vacuo to give the crude product, which was purified via silica gel chromatography, eluting with a gradient of methanol-dichloromethane-0.880 ammonia (10:989:1 to 30:967:3), to give the title compound as a pale yellow oil (33 mg).

NMR ($C_6D_6$, selected data from the free base): 0.82–0.88 (m, 2H), 0.94 (d, 3H), 1.10–1.22 (m, 6H), 1.22 (s, 3H), 1.39–1.49 (m, 3H), 1.42 (s, 3H), 1.58–1.69 (m, 5H), 1.82 (m, 1H), 2.15–2.48 (m, 6H), 2.71 (m, 1H), 6.72 (dd, 1H), 7.00 (d, 1H), 7.14 (d, 1H) and 7.16 (br s, 1H).

MS (APCI$^+$): M/Z [MH$^+$] 387.3; $C_{24}H_{38}N_2O_2$+H requires 387.3.

Example 47

(±)-N-(3-Cyclohexylpropyl)-trans-3,4-dimethyl4-(3-hydroxy-4-propionylaminophenyl)piperidine To a stirred solution of (±)-N-(3-cyclohexylpropyl)-trans-3,4-dimethyl-4-(4-amino-3-hydroxyphenyl)piperidine (Example 45, 0.106 g, 0.30 mmol) and pyridine (27 µL, 0.33 mmol) in tetrahydrofuran (7 mL) at 0° C. was added propionyl chloride (28 µL, 0.33 mmol). After 1.5 hours, the reaction mixture was diluted with aqueous saturated sodium hydrogen-carbonate (10 mL) and extracted with dichloromethane (3×10 mL). The combined extracts were washed with brine (20 mL), dried over $Na_2SO_4$, filtered and concentrated in vacuo to give a residue which was dissolved in methanol (10 mL) and allowed to stir for 18 hours. The reaction mixture was concentrated in vacuo to give the crude product, which was purified via silica gel chromatography, eluting with a gradient of methanol-dichloromethane-0.880 ammonia (10:989:1 to 30:967:3), to give the title compound as a pale yellow oil (33 mg).

NMR ($C_6D_6$, selected data from the free base): 0.82–0.88 (m, 2H), 0.84 (t, 3H), 0.94 (d, 3H), 1.07–1.21 (m, 6H), 1.21 (s, 3H), 1.39–1.51 (m, 3H), 1.58–1.69 (m, 7H), 1.81 (m, 1H), 2.12–2.48 (m, 6H), 2.70 (m, 1H), 6.71 (dd, 1H), 6.84 (s, 1H), 6.86 (d, 1H) and 7.15 (d, 1H).

MS (APCI$^+$): M/Z [MH$^+$] 401.4; $C_{25}H_{40}N_2O_2$+H requires 401.3.

Example 48

(±)-N-Hexyl-trans-3,4-dimethyl4-(4-N',N'-dimethyl-amino-3-hydroxyphenyl)piperidine To a stirred solution of (±)-N-hexyl-trans-3,4-dimethyl-4-(3-hydroxy-4-aminophenyl)piperidine (Example 4, 0.100 g, 0.33 mmol) and formic acid (41 µL, 1.09 mmol) in chloroform (3 mL) was added formaldehyde (82 µL of 37% aqueous w/w solution, 1.09 mmol) and the reaction mixture was heated to reflux. Additional formaldehyde (82 µL of 37% aqueous w/w solution) and formic acid (41 µL, 1.09 mmol) was introduced after 12 and 36 hours and the reaction was stirred at reflux for an additional 4 hours. Upon cooling, the reaction mixture was diluted with water (10 mL), adjusted to pH 11 with 5N sodium hydroxide and extracted with 3:1 n-butanol-toluene (3×10 mL). The combined extracts were dried over $Na_2SO_4$, filtered and concentrated in vacuo to give the crude product, which was purified via silica gel chromatography, eluting with methanol-dichloromethane-0.880 ammonia (10:489:1), to give the title compound as a pale yellow oil (5 mg).

NMR ($C_6D_6$, selected data from the free base): 0.85 (t, 3H), 0.95 (d, 3H), 1.21 (s, 3H), 1.21–1.27 (m, 6H), 1.40–1.44 (m, 3H), 1.81 (m, 1H), 2.06–2.41 (m, 6H), 2.18 (s, 6H), 2.66 (m, 1H), 6.74 (m, 1H), 6.88 (m, 1H) and 7.13 (m, 1H).

MS (APCI$^+$): M/Z [MH$^+$] 333.4; $C_{21}H_{36}N_2O$+H requires 333.3.

Example 49

(±)-N-Hexyl-trans-3,4-dimethyl-4-(3-hydroxy-4-isopropenylphenyl)piperidine

To a stirred solution of (±)-N-hexyl-trans-3,4-dimethyl-4-(3-N',N'-diethylcarbamyloxyphenyl)piperidine (Preparation 4, 0.103 g, 0.27 mmol) and N,N,N',N'-tetramethylethylenediamine (48 µL, 0.32 mmol) in tetrahydrofuran (1 mL) at −78° C. was added s-butyllithium (0.25 mL of 1.3 M in cyclohexane, 0.32 mmol). After 1 hour, acetone (98 µL, 1.33 mmol) was added and the reaction mixture was allowed to warm to room temperature overnight. The reaction mixture was diluted with aqueous saturated sodium hydrogencarbonate (25 mL) and extracted with dichloromethane (3×30 mL). The combined extracts were washed with brine (15 mL), dried over $Na_2SO_4$, filtered and concentrated in vacuo to give the crude product, which was purified via silica gel chromatography, eluting with a gradient of methanol-dichloromethane-0.880 ammonia (2:197:1 to 4:195:1), to give the title compound as a pale yellow oil (64 mg).

NMR ($C_6D_6$, selected data from the free base): 0.85 (t, 3H), 0.94 (d, 3H), 1.19–1.28 (m, 6H), 1.21 (s, 3H), 1.38–1.46 (m, 3H), 1.81 (m, 1H), 1.89 (s, 3H), 2.10–2.46 (m, 6H), 2.69 (m, 1H), 5.01 (m, 2H), 6.73 (dd, 1H), 6.91 (d, 1H) and 7.04 (d, 1H).

MS (APCI$^+$): M/Z [MH$^+$] 330.3; $C_{22}H_{35}NO$+H requires 330.3.

Example 50

(±)-N-Hexyl-trans-3,4-dimethyl-4-(4-allyl-3-N',N'-diethylcarbamyloxyphenyl)piperidine To a stirred solution of (±)-N-hexyl-trans-3,4-dimethyl-4-(3-N',N'-diethylcarbamyloxyphenyl)piperidine (Preparation 4, 0.104 g, 0.27 mmol) and N,N,N',N'-tetramethylethylenediamine (48 µL, 0.32 mmol) in tetrahydrofuran (1 mL) at −78° C. was added s-butyllithium (0.246 mL of 1.3 M in cyclohexane, 0.32 mmol). After 1 hour, allyl bromide (0.115 mL, 1.33 mmol) was added and stirring was continued for an additional 1 hour. The reaction mixture was diluted with water (25 mL) and extracted with dichloromethane (3×20 mL). The combined organic extracts were washed with brine (30 mL), dried over $Na_2SO_4$, filtered and concentrated in vacuo to give the crude product, which was employed without further purification (0.107 g).

NMR ($C_6D_6$, selected data from the free base): 0.84–0.95 (m, 12H), 1.17 (s, 3H), 1.19–1.24 (m, 6H), 1.32–1.41 (m, 3H), 1.76 (m, 1H), 2.05–2.40 (m, 6H), 2.63 (m, 1H), 3.08 (m, 4H), 3.33 (d, 2H), 4.98 (m, 2H), 5.93 (m, 1H), 6.96 (dd, 1H), 7.07–7.10 (d, 1H) and 7.23 (d, 1H).

MS (APCI$^+$): M/Z [MH$^+$] 429.3; $C_{27}H\therefore N_2O_2$+H requires 429.3.

Example 51

(±)-N-Hexyl-trans-3,4-dimethyl(3-N',N'-diethylcarbamyloxy-4-methylphenyl)piperidine To a stirred solution of (±)-N-hexyl-trans-3,4-dimethyl-4-(3-N',N'-diethylcarbamyloxyphenyl)piperidine (Preparation 4, 0.215 g, 0.55 mmol) and N,N,N',N'-tetramethylethylenediamine (0.100 mL, 0.67 mmol) in tetrahydrofuran (1 mL) at −78° C. was added s-butyllithium (0.511 mL of 1.3 M in cyclohexane, 0.67 mmol). After 1 hour, methyl iodide (0.173 mL, 2.77 mmol) was added and stirring was continued for an additional 1 hour. The reaction mixture was diluted with water (25 mL) and extracted with dichloromethane (3×20 mL). The combined extracts were washed with brine (30 mL), dried over $Na_2SO_4$, filtered and concentrated in vacuo to give the crude product, which was employed without further purification (0.213 g).

NMR ($C_6D_6$, selected data from the free base): 0.80–1.04 (m, 12H), 1.17 (s, 3H), 1.20–1.24 (m, 6H), 1.32–1.41 (m, 3H), 1.76 (m, 1H), 2.05–2.40 (m, 6H), 2.11 (s, 3H), 2.63 (m, 1H), 3.08 (m, 4H), 6.90 (m, 1H), 6.99 (m, 1H) and 7.10–7.15 (m, 1H).

MS (APCI$^+$): M/Z [MH$^+$] 403.4; $C_{25}H_{42}N_2O_2$+H requires 403.3.

Example 52

(±)-N-Hexyl-trans-3,4-dimethyl-4-(3-N',N'-diethylcarbamyloxy-4-ethylphenyl) piperidine To a stirred solution of (±)-N-hexyl-trans-3,4-dimethyl-4-(3-N',N'-diethylcarbamyloxy-4-methylphenyl)piperidine (Example 51, 0.260 g, 0.65 mmol) and N,N,N',N'-tetramethylethylenediamine (0.117 mL, 0.78 mmol) in tetrahydrofuran (2 mL) at −78° C. was added s-butyllithium (0.597 mL of 1.3 M in cyclohexane, 0.78 mmol). After 1 hour, methyl iodide (0.201 mL, 3.23 mmol) was added and stirring was continued for an additional 1 hour. The reaction mixture was diluted with water (25 mL) and extracted with dichloromethane (3×20 mL). The combined extracts were washed with brine (30 mL), dried over $Na_2SO_4$, filtered and concentrated in vacuo to give the crude product, which was purified via silica gel chromatography, eluting with a gradient of methanol-dichloromethane-0.880 ammonia (5:494:1 to 10:489:1), to give the title compound as a pale yellow oil (90 mg).

NMR ($C_6D_6$, selected data from the free base): 0.86 (t, 3H), 0.90–0.96 (m, 12H), 1.08 (s, 3H), 1.10–1.26 (m, 6H), 1.43–1.58 (m, 3H), 1.71 (m, 1H), 2.08–2.62 (m, 6H), 2.29 (q, 2H), 2.71 (m, 1H), 3.09 (m, 4H), 6.86 (dd, 1H), 7.04 (d, 1H) and 7.10–7.13 (d, 1H).

MS (APCI$^+$): M/Z [MH$^+$] 417.3; $C_{26}H_{44}N_2O_2$+H requires 417.3.

Example 53

(±)-N-Hexyl-trans-3,4-dimethyl-4-(3-N',N'-diethylcarbamyloxy-4-N''-methylaminocarbonylphenyl)piperidine To a stirred solution of (±)-N-hexyl-trans-3,4-dimethyl-4-(3-N',N'-diethylcarbamyloxyphenyl)piperidine (Preparation 4, 0.111 g, 0.29 mmol) and N,N,N',N'-tetramethylethylenediamine (52 μL, 0.34 mmol) in tetrahydrofuran (1 mL) at −78° C. was added s-butyllithium (0.263 mL of 1.3 M in cyclohexane, 0.34 mmol). After 1 hour, methyl isocyanate (84 μL, 1.43 mmol) was added and stirring was continued for an additional 1 hour. The reaction mixture was diluted with water (25 mL) and extracted with dichloromethane (3×20 mL). The combined extracts were washed with brine (30 mL), dried over $Na_2SO_4$, filtered and concentrated in vacuo to give the crude product, which was employed without further purification (0.113 g).

MS (APCI$^+$): M/Z [MH$^+$] 446.3; $C_{26}H_{43}N_3O_3$+H requires 446.3.

Example 54

(±)-N-Hexyl-trans-3,4-dimethyl-4-(3-N',N'-diethylthiocarbamyloxy-4-fluorophenyl)piperidine To a stirred solution of (±)-N-hexyl-trans-3,4-dimethyl-4-(3-N',N'-diethylthiocarbamyloxyphenyl)piperidine (Preparation 6, 0.104 g, 0.26 mmol) and N,N,N',N'-tetramethylethylenediamine (78 μL, 0.51 mmol) in tetrahydrofuran (2 mL) at −78° C. was added s-butyllithium (0.395 mL of 1.3 M in cyclohexane, 0.51 mmol). After 1 hour, a solution of N-fluorobenzenesulfonimide (0.405 g, 1.28 mmol) in tetrahydrofuran (1 mL) was added and stirring was continued for an additional 3 hours. The reaction mixture was diluted with saturated aqueous sodium hydrogencarbonate (25 mL) and extracted with dichloromethane (3×20 mL). The combined extracts were dried over $Na_2SO_4$, filtered and concentrated in vacuo to give the crude product, which was purified via silica gel chromatography, eluting with a gradient of ethyl acetate-dichloromethane (30:70 to 50:50), to give the title compound as a yellow oil (40 mg).

NMR ($C_6D_6$, selected data from the free base): 0.83–0.97 (m, 12H), 1.12 (s, 3H), 1.18–1.27 (m, 6H), 1.37–1.42 (m, 3H), 1.68 (m, 1H), 2.07–2.39 (m, 6H), 2.62 (m, 1H), 3.12 (m, 2H), 3.50 (m, 2H), 6.73 (m, 1H), 6.83 (m, 1H) and 7.14 (m, 1H).

MS (APCI$^+$): M/Z [MH$^+$] 423.3; $C_{24}H_{39}FN_2OS$+H requires 423.3.

Example 55

(±)-N-Hexyl-trans-3,4-dimethyl-4-(3-N',N'-diethylcarbamyloxy4-formylphenyl)piperidine To a stirred solution of (±)-N-hexyl-trans-3,4-dimethyl-4-(3-N',N'-diethylcarbamyloxyphenyl)piperidine (Preparation 4, 0.515 g, 1.32 mmol) and N,N,N',N'-tetramethylethylenediamine (0.240 mL, 1.59 mmol) in tetrahydrofuran (5 mL) at −78° C. was added s-butyllithium (1.22 mL of 1.3 M in cyclohexane, 1.59 mmol). After 1 hour, N,N-dimethyl-formamide (0.513 mL, 6.62 mmol) was added and stirring was continued for an additional 1 hour. The reaction mixture was diluted with saturated aqueous sodium hydrogencarbonate (25 mL) and extracted with dichloromethane (3×20 mL). The combined extracts were dried over $Na_2SO_4$, filtered and concentrated in vacuo to give the crude product which was used without further purification (0.456 g).

NMR ($C_6D_6$, selected data from the free base): 0.77 (d, 3H), 0.82–0.94 (m, 9H), 1.04 (s, 3H), 1.18–1.34 (m, 6H), 1.37–1.40 (m, 3H), 1.66 (m, 1H), 1.99–2.38 (m, 6H), 2.58 (m, 1H), 3.07 (q, 4H), 6.57 (dd, 1H), 6.86–6.89 (m, 2H) and 9.32 (s, 1H).

MS (APCI$^+$): M/Z [MH$^+$] 417.3; $C_{25}H_{40}N_2O_3$+H requires 417.3.

Example 56

Compounds according to the present invention, for example the compound of Example 8, were found to display anti-pruritic activity when tested in accordance with the above procedure.

Preparation of Starting Materials

Preparation 1

(±)-N-Hexyl-trans-3,4-dimethyl-4-(3-N',N'-diethylcarbamyloxy-4-trimethylsilylphenyl)piperidine To a stirred solution of (±)-N-hexyl-trans-3,4-dimethyl-4-(3-N',N'-diethylcarbamyloxyphenyl)piperidine (Preparation 4, 0.206 g, 0.53 mmol) and N,N,N',N'-tetramethylethylenediamine (96 μL, 0.66 mmol) in tetrahydrofuran (2 mL) at −78° C. was added s-butyllithium (0.489 mL of 1.3 M in cyclohexane, 0.66 mmol). After 1 hour, chlorotrimethylsilane (0.336 mL, 2.65 mmol) was added and stirring was continued for an additional 10 minutes. The reaction mixture was diluted with saturated aqueous sodium hydrogencarbonate (25 mL) and extracted with dichloromethane (3×20 mL). The combined extracts were dried over $Na_2SO_4$, filtered and concentrated in vacuo to give the crude product, which was used without further purification (0.241 g).

NMR ($C_6D_6$, selected data from the free base): 0.28 (s, 9H), 0.83 (t, 3H), 0.91–0.96 (m, 9H), 1.18 (s, 3H), 1.21–1.27 (m, 6H), 1.35–1.38 (m, 3H), 1.79 (m, 1H), 2.06–2.40 (m, 6H), 2.62 (m, 1H), 3.14 (m, 4H), 7.03 (dd, 1H), 7.18 (d, 1H) and 7.39 (d, 1H).

MS ($APCI^+$): M/Z [$MH^+$] 461.3; $C_{27}H_{48}N_2O_2Si+H$ requires 461.3.

Preparation 2

(±)-N-Hexyl-trans-3,4-dimethyl-4-(3-hydroxy-2-methyl-4-trimethylsilylphenyl)piperidine To a stirred solution of (±)-N-hexyl-trans-3,4-dimethyl-4-(3-N',N'-diethylcarbamyloxy-4-trimethylsilylphenyl)piperidine (Preparation 1, 0.251 g, 0.51 mmol) and N,N,N',N'-tetramethylethylenediamine (99 μL, 0.65 mmol) in tetrahydrofuran (2 mL) at −78° C. was added s-butyllithium (0.503 mL of 1.3 M in cyclohexane, 0.65 mmol). After 1 hour, methyl iodide (0.170 mL, 2.72 mmol) was added and stirring was continued for an additional 2 hours. The reaction mixture was diluted with saturated aqueous sodium hydrogencarbonate (25 mL) and extracted with dichloromethane (3×20 mL). The combined extracts were dried over $Na_2SO_4$, filtered and concentrated in vacuo to give the crude product, which was purified via silica gel chromatography, eluting with a gradient of methanol-dichloromethane-0.880 ammonia (5:494:1 to 20:479:1), to give the title compound as a yellow oil (71 mg).

NMR ($C_6D_6$, selected data from the free base): 0.36 (s, 9H), 0.87 (t, 3H), 1.02 (d, 3H), 1.21 (s, 3H), 1.21–1.32 (m, 6H), 1.46–1.79 (m, 3H), 2.03 (m, 1H), 2.44–2.82 (m, 6H), 3.03 (m, 1H), 3.39 (s, 3H), 6.60 (s, 1H), 6.73 (d, 1H) and 7.36 (d, 1H).

MS ($APCI^+$): M/Z [$MH^+$] 376.3; $C_{23}H_{41}NOSi+H$ requires 376.3.

Preparation 3

(±)-N-Hexyl-trans-3,4-dimethyl-4-(3-triisopropylsilyl-oxyphenyl)piperidine

To a solution of (±)-N-hexyl-trans-3,4-dimethyl-4-(3-hydroxyphenyl)piperidine (Preparation 7, 100 mg, 0.345 mmol) in N,N-dimethyl-formamide (1 mL) was added imidazole (47 mg, 0.690 mmol) and chlorotriisopropylsilane (106 mg, 0.552 mmol). The reaction was stirred under nitrogen for 60 hours then washed with saturated sodium hydrogencarbonate solution and extracted with dichloromethane. The solvents were removed in vacuo and the residue was dissolved in hexane, filtered and the hexane removed in vacuo to give the title compound as an oil (152 mg).

NMR ($CDCl_3$, selected data from the free base): 0.77 (3H, d), 0.87 (3H, t), 1.09 (21H, m), 1.31 (3H, s), 6.67 (1H, d), 6.80 (1H, s), 6.87 (1H, d) and 7.13 (1H, t).

MS ($APCI^+$): M/Z [$MH^+$] 446.1; $C_{28}H_{51}NOSi+H$ requires 446.4.

Preparation 4

(±)-N-Hexyl-trans-3,4-dimethyl-4-(3-N',N'-diethyl-carbamyloxyphenyl)piperidine

To a solution of (±)-N-hexyl-trans-3,4-dimethyl-4-(3-hydroxyphenyl)piperidine (Preparation 7, 8.0 g, 28 mmol) in pyridine (32 mL) was added 1-[(chlorocarbonyl)(ethyl)amino]ethane (3.8 mL, 30.0 mmol), and the reaction mixture was stirred overnight. Water (200 mL) was added to the reaction mixture and the product was extracted with dichloromethane (3×200 mL). The organics were dried ($Na_2SO_4$) and then concentrated in vacuo. The crude residue was chromatographed on silica gel, eluting with ethyl acetate-hexane (20:80), to give the product as a colourless oil (4.0 g).

NMR ($CDCl_3$, selected data from the free base): 0.8 (d, 3H), 0.9 (t, 3H), 1.2–1.4 (m, 14H), 3.3–3.5 (m, 4H), 6.9 (d, 1H), 7.0 (s, 1H), 7.1 (d, 1H and 7.3 (t, 1H).

MS ($ESI^+$): M/Z [$MH^+$] 389.2; $C_{24}H_{40}N_2O_2+H$ requires 389.3.

Preparation 5

(±)-N-Hexyl-trans-3,4-dimethyl-4-(3-N',N'-dimethyl-carbamyloxyphenyl)piperidine

To a stirred solution of (±)-N-hexyl-trans-3,4-dimethyl-4-(3-hydroxyphenyl)piperidine (Preparation 7, 0.289 g, 1.00 mmol) and dimethylcarbamyl chloride (0.101 mL, 1.1 mmol) in tetrahydrofuran (2 mL) and pyridine (2 mL) was added triethylamine (0.279 mL, 2 mmol). After 24 hours, the reaction mixture was diluted with water (20 mL) and extracted with dichloromethane (3×20 mL). The combined extracts were washed with brine (30 mL), dried ($Na_2SO_4$), filtered and concentrated in vacuo to give the crude product, which was chromatographed on silica gel, eluting with a gradient of methanol-dichloromethane-0.880 ammonia (10:989:1 to 30:967:3), to give the title compound as a yellow oil (0.329 g).

NMR ($C_6D_6$, selected data from the free base) : 0.85 (t, 3H), 0.90 (d, 3H), 1.17 (s, 3H), 1.19–1.29 (m, 6H), 1.33–1.43 (m, 3H), 1.78 (m, 1H), 2.05–2.40 (m, 6H), 2.51 (s, 3H), 2.55 (s, 3H), 2.63 (m, 1H), 6.93 (m, 1H), 7.04–7.12 (m, 2H) and 7.24 (m, 1H).

MS ($APCI^+$): M/Z [$MH^+$] 361.3; $C_{22}H_{36}N_2O_2+H$ requires 361.3.

Preparation 6

(±)-N-Hexyl-trans-3,4-dimethyl-4-(3-N',N'-diethyl-thiocarbamyloxyphenyl)piperidine To a stirred solution (±)-N-hexyl-trans-3,4-dimethyl-4-(3-hydroxy-phenyl)piperidine (Preparation 7, 0.710 g, 2.45 mmol) and potassium hydroxide (0.137 g, 2.45 mmol) in water (5 mL) and tetrahydrofuran (5 mL) was added diethylthiocarbamyl chloride (0.485 g, 3.2 mmol). After 24 hours, additional potassium hydroxide (0.137 g, 2.45 mmol) and diethylthiocarbamyl chloride (0.485 g, 3.2 mmol) was introduced. After an additional 24 hours, the reaction mixture was diluted with water (20 mL) and extracted with ethyl acetate (3×25 mL). The combined extracts were washed with brine (30 mL), dried over $Na_2SO_4$, filtered and concentrated in vacuo to give the crude product, which was chromatographed on silica gel, eluting with a gradient of methanol-dichloromethane-0.880 ammonia (10:989:1 to 30:967:3), to give the title compound as a yellow oil (0.627 g).

NMR ($C_6D_6$, selected data from the free base): 0.83–0.88 (m, 6H), 0.95–1.01 (m, 6H), 1.20 (s, 3H), 1.23–1.42 (m, 9H), 1.77 (m, 1H), 2.05–2.42 (m, 6H), 2.64 (m, 1H), 3.10 (q, 2H), 3.55 (q, 2H), 6.91 (m, 1H), 6.98 (m, 1H), 7.05–7.13 (m, 1H) and 7.19 (m, 1H).

MS ($APCI^+$): M/Z [$MH^+$] 405.3; $C_{24}H_{40}N_2OS+H$ requires 405.3.

Preparation 7

(±)-N-Hexyl-trans-3,4-dimethyl-4-(3-hydroxyphenyl)piperidine

To a stirred solution of (±)-trans-3,4dimethyl-4-(3-hydroxyphenyl)piperidine (J. A. Werner et al., *J. Org. Chem.*, 1996, 61, 587: 2.0 g, 9.8 mmol) in N,N-dimethylformamide (50 mL) was added sodium hydrogen-carbonate (1.76 g, 20.95 mmol) and bromohexane (1.64 g, 9.9 mmol). The reaction mixture was heated under reflux for 3 hours and then cooled to room temperature. The reaction mixture was diluted with water (100 mL) and extracted with dichloromethane (4×50 mL). The combined extracts were washed with brine (100 mL), dried ($MgSO_4$), filtered and concentrated in vacuo to give the crude product. The crude product was chromatographed on silica gel (50 g), eluting with ethyl acetate-hexane-0.880 ammonia (30:69:1), to give the title compound as a light brown oil (2.68 g).

NMR ($CDCl_3$, selected data from the free base): 0.75 (d, 3H), 0.85 (t, 3H), 1.15–1.25 (m, 6H), 1.3 (s, 3H), 2.0 (m, 1H), 2.35 (m, 4H), 2.6 (m, 2H) and 6.55–7.2 (m, 4H).

MS ($TSI^+$): M/Z [$MH^+$] 290.2; $C_{19}H_{31}NO+H$ requires 290.3.

Preparation 8

(±)-N-(3-Cyclohexylpropyl)-trans-3,4-dimethyl-4-(3-hydroxyphenyl)piperidine

A mixture of (±)-trans-3,4-dimethyl-4-(3-hydroxyphenyl) piperidine (J. A. Werner et al., *J. Org. Chem.*, 1996, 61, 587: 82 mg, 0.4 mmol), 3-(cyclohexyl)chloropropane (71 mg, 0.4 mmol), sodium hydrogen-carbonate (37 mg, 0.44 mmol), sodium iodide (3 mg, 0.02 mmol) and dimethylformamide (5 mL) was heated at 70° C. for 8 hours, then it was cooled to room temperature and quenched with water (30 mL). The resultant mixture was extracted with dichloromethane (30 mL), and the organic layer retained. The aqueous layer was re-extracted with dichloromethane (2×20 mL), and the organic portions were combined, washed with brine (40 mL), dried ($Na_2SO_4$), filtered and concentrated in vacuo, to afford the crude material. This was chromatographed on silica gel, eluting with a gradient system of methanol-dichloromethane-0.880 ammonia (10:989:1 to 20:978:2), to give the title compound as a colourless viscous oil (56 mg).

NMR ($C_6D_6$, selected data from the free base): 0.90 (d, 3H), 1.20 (s, 3H), 1.80 (m, 1H), 2.80 (m, 1H) and 6.60–7.10 (m, 4H).

MS ($APCI^+$): M/Z [$MH^+$] 330.3; $C_{22}H_{35}NO+H$ requires 330.5.

What is claimed is:
1. A compound of formula I,

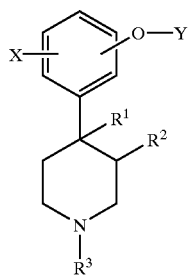

I wherein $R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —$N(R^{4a})(R^{4b})$ or $C_{1-10}$ alkyl, wherein said alkyl group is optionally substituted, and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and W—$A^1$—$N(R^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group —$N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$;

or $R^{5b}$ and $R^{5c}$ together represent unbranched $C_{2-4}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic, and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents one or more substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy, and $N(R^{15a})(R^{15b})$), $C(O)R^{16a}$, $C(O)OR^{16b}$, $OC(O)R^{16c}$, $S(O)_rOR^{16d}$, $S(O)_rR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms); or pharmaceutically, or veterinarily, acceptable derivatives thereof.

2. A compound as claimed in claim 1, wherein the group OY is attached to the benzene ring in the position meta-relative to the piperidine group.

3. A compound as claimed in claim 1, wherein the substituent(s) X is/are attached to the benzene ring in position(s) that are ortho- and/or para- relative to the piperidine group.

4. A compound as claims in claim 1 wherein $R^1$ represents $C_{1-2}$ alkyl.

5. A compound as claimed in claim 1 wherein $R^2$ represents H or $C_{1-2}$ alkyl.

6. A compound as claimed in claim 1 wherein $R^3$ represents $C_{1-8}$ alkyl, wherein said alkyl group is optionally substituted and/or terminated by one or more substituents selected from the group consisting of $C_{3-8}$ cycloalkyl, $OR^{4c}$, CN, $Het^1$ and aryl (which latter group is optionally substituted by one or more substituents selected from the group consisting of OH, $C_{1-2}$ alkyl, $C_{1-2}$ alkoxy or halo).

7. A compound as claimed in claim 1 wherein $R^{4c}$ represents H, $C_{1-6}$, alkyl, $C_{4-6}$ cycloalklyl, aryl, or $Het^2$.

8. A compound as claimed in claim 1 wherein $Het^1$ and $Het^2$ independently represent 5- to 7-membered heterocyclic groups, which groups contain at least one heteroatom selected from the group consisting of oxygen, sulfur and nitrogen, and which groups are optionally substituted by one or more $C_{1-2}$ alkyl group (which alkyl groups are optionally substituted by one or more halo atoms).

9. A compound as claimed in claim 1 wherein X represents one to three substituents selected from the group consisting of halo, nitro, $C_{2-6}$ alkenyl, $C_{1-6}$ alkyl (which alkyl group is optionally substituted and/or terminated by a substituent selected from the group consisting of OH, $C_{1-4}$ alkoxy and $N(R^{15a})(R^{15b})$), $C(O)R^{16a}$, $C(O)OR^{16b}$, $S(O)_t R^{17a}$, $N(R^{18a})(R^{18b})$, $C(O)N(R^{18c})(R^{18d})$, $N(R^{18g})C(O)R^{16f}$, $N(R^{18h})C(O)OR^{19}$, $N(R^{18i})C(O)N(R^{18j})(R^{18k})$ and $N(R^{18m})S(O)_2R^{17b}$.

10. A compound as claimed in claim 1 wherein $R^{15a}$ and $R^{15b}$ independently represent H or $C_{14}$ alkyl; $R^{16a}$ and $R^{16f}$ independently represent H or $C_{1-6}$ alkyl (which latter group is optionally substituted by one or more halo atoms); $R^{17a}$ and $R^{17b}$ independently represent $C_{1-4}$ alkyl (optionally substituted by one or more halo atoms) or $N(R^{20a})(R^{20b})$; $R^{18a}$ to $R^{18m}$ independently represent H, $C_{1-6}$ alkyl, or $R^{18j}$ and $R^{18k}$ together represent unbranced $C_{3-6}$ alkylene optionally interrupted by oxygen; $R^{19}$ represents $C_{1-4}$ alkyl; and/or $R^{20a}$ and $R^{20b}$ independently represent H or $C_{1-4}$ alkyl.

11. A compound as claimed in claim 1 wherein the substituent(s) X is/are attached to the benzene ring in the position(s) that are ortho and/or para- relative to the OY group.

12. A pharmaceutical composition comprising a pharmaceutically effective amount of compound as defined in any one of claims 1–11, in admixture with a pharmaceutically, or a veterinarily, acceptable adjuvant, diluent or carrier.

13. The pharmaceutical composition as claimed in claim 1, which is a veterinary formulation.

14. A method of treating or preventing pruritus, which comprises administering a therapeutically effective amount of a compound as defined in any one of claims 1–11 to a patient in need of such treatment.

15. A process for the preparation of a compound of formula I

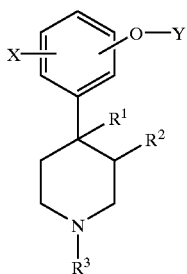

which comprises:
reducing, using reducing agents, a compound of formula II,

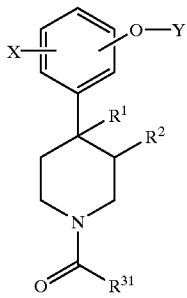

wherein
$R^1$ and $R^2$ are each independently H or $C_{1-4}$ alkyl;
$R^3$ represents $C_1$ alkyl wherein said alkyl group is optionally substituted by $C_{3-8}$ cycloalkyl, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)); n is 0, 1 or 2;
$R^{31}$ represents H, $C_{3-8}$ cycloalkyl, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms));
$R^6$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;
$Het^1$ represents 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);
Y represents $R^{11}$;
$R^{11}$ represents H;
X represents one or more substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy, and $N(R^{15a})(R^{15b})$), $C(O)R^{16a}$, $C(O)OR^{16b}$, $OC(O)R^{16c}$, $S(O)_rOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;
$R^{15a}$ to $R^{15c}$ independently represent H, $C_{1-6}$ alkyl or $C_{3-7}$ cycloalkyl (which latter two groups are optionally substituted by one or more halo atoms);
$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;
$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;
provided that $R^{17a}$ does not represent $N(R^{20a})(R^{20b})$ when t is 1;
$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;
$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;
$R^{20a}$ to $R^{20c}$ independently represent H, $C_{1-4}$ alkyl or $C_{3-7}$ cycloalkyl (which latter two groups are optionally substituted by one or more halo atoms);
r is 1 or 2;
t is 0, 1 or 2; and
$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

16. A process for the preparation of a compound of Formula I:

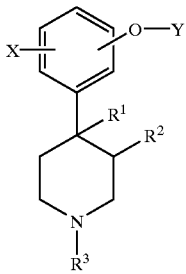

which comprises reducing a compound of Formula II using reducing agents,

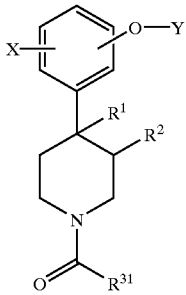

wherein $R^1$ and $R^2$ are each independently H or $C_{1-4}$ alkyl;

$R^3$ is $C_{2-10}$ alkyl wherein said alkyl group is optionally substituted by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, Het$^1$, aryl adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and W—$A^1$—N$(R^{5b})(R^{5c})$, which alkyl group is attached to the piperidine nitrogen atom via a $CH_2$ group;

$R^{31}$ represents $C_{1-9}$ alkyl which is unsubstituted or optionally substituted by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})$—$S(O)_2R^6$, Het$^1$, aryl and adamantyl which latter two groups are optionally substituted by one or more substituents selected from the group consisting of OH, nitro, amino, halo, CN, $CH_2CN$, $CONH_2$, $C_{1-4}$alkyl, $C_4$alkoxy and $C_{1-5}$ alkanoyl) which latter three groups are optionally substituted by one or more halo atoms)), or W—$A^1$—N$(R^{5b})(R^{5c})$;

W represents a single bond, CO or $S(O)_p$; $A^1$ represents a single bond or $C_{1-10}$ alkylene;

p is 0, 1 or 2;

n is 0, 1 or 2;

$R^{4c}$ and $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or Het$^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or Het$^3$ or $R^{5b}$ and $R^{5c}$ together represent unbranched $C_{2-6}$ alkylene group which alkylene group is optionally interrupted by O, S or $NR^7$ group and is optionally substituted by one or more $C_{1-4}$ alkyl groups;

$R^6$ represents $C_{1-4}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ is H, $C_{1-6}$ alkyl, $C_{3-8}$ cycloalkyl, $A^2$—($C_{3-8}$ cycloalkyl) or $A^2$ aryl;

$A^2$ represents $C_{1-6}$ alkylene;

Het$^1$, Het$^2$ and Het$^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents one or more substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_nOR^{16d}$, $S(O)_nR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or Het$^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl or $C_{1-4}$ alkoxy), Het$^9$ or $N(R^{20a})(R^{20b})$;

provided that R[17a] does not represent N(R[20a])(R[20b]) when t is 1;

R[18a] to R[18m] independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or Het[10], or R[18j] and R[18k] together represent unbranched $C_{3-6}$ alkylene, which alkylene group is optionally interrupted by oxygen, sulfur or an NR[20c] group;

R[19] represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl or $C_{1-4}$ alkoxy) or Het[11];

R[20a] to R[20c] independently represent H, $C_{1-4}$ alkyl or $C_{3-7}$ cycloalkyl (which latter two groups are optionally substituted by one or more halo atoms);

r is 1 or 2;

t is 0, 1 or 2;

Het[8] to Het[11] represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

17. A process for preparing a compound of the formula:

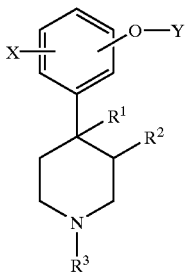

I which comprises reacting a compound of formula III,

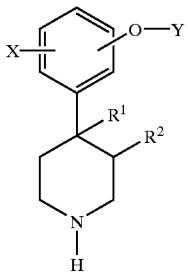

III with a compound of formula V,

R[3]—L[1]    V wherein
L[1] represents a leaving group;
R[1] and R[2] are each independently H or $C_{1-4}$ alkyl
R[3] represents aryl (optionally substituted by one or more substituents selected from the group consisting of OH, nitro, halo CN, $CH_2$, CN, $CONH_2$, $C_{1-4}$ alkyl, $C_{1-4}$ alkoxy, $C_{1-5}$ alkanoyl (which latter three groups are optionally substituted by one or more halo atoms) and —N(R[4a])(R[4b])) or $C_{1-10}$ alkyl, wherein said alkyl, group is optionally substituted and/or terminated by one or more substituents selected from the group consisting of OR[4c], S(O)$_n$R[4d], CN, halo, $C_{1-6}$ alkoxy carbonyl, $C_{2-6}$ alkanoyl, $C_{2-6}$alkanoyloxy, $C_{3-8}$ cycloalkyl, $C_{4-9}$ cycloalkanoyl, N(R[5a])S(O)$_2$R[6], Het[1], aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and W—A[1]—N(R[5b])(R[5c]);

n is 0, 1 or 2;

W represents a single bond, C(O) or S(O)$_p$;

A[1] represents a single bond or $C_{1-10}$ alkylene;

provided that when both W and A[1] represent single bonds, then the group —N(R[5b])(R[5c]) is not directly attached to an unsaturated carbon atom;

p is 0, 1, or 2;

R[4a] to R[4d] each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or Het[2];

provided that R[4d] does not represent H when n represents 1 or 2;

R[5a] to R[5c] each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or Het[3];

or R[5b] and R[5c] together represent unbranched $C_{2-6}$ alkylene group which alkylene group is optionally interrupted by O, S or NR[7] group and optionally substituted by one or more $C_{1-4}$ alkyl groups;

R[6] represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

R[7] represents H, $C_{1-6}$ alkyl, $C_{3-8}$ cycloalkyl, A[2] ($C_{3-8}$ cycloalkyl) or A[2]-aryl;

A[2] represents $C_{1-6}$ alkylene;

Het[1], Het[2] and Het[3] independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents R[11];

R[11] represents H;

X represents one or more substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl or $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl or $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

18. A process for preparing a compound of the Formula:

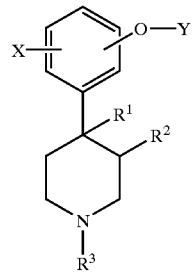

I which comprises reacting a corresponding compound of formula III,

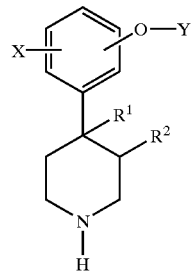

III with a compound of formula VI, $R^{31}CHO$         VI in the presence of a reducing agent, wherein $R^3$ is $C_1$ alkyl optionally substituted by $R^{31}$;

$R^{31}$ represents H, $C_{3-8}$ cycloalkyl, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and $W-A^1-N(R^{5b})(R^{5c})$;

$R^1$ and $R^2$ are each independently H or $C_{1-4}$ alkyl;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group $-N(R^{5b})(R^{5c})$ is not directly attached to an unsaturated carbon atom;

p is 0, 1, or 2;

$R^{4c}$ and $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alylkene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-4}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents one or more substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rOR^{16d}$, $S(O)_rR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more, halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ and $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

19. A process for preparing a compound of formula I

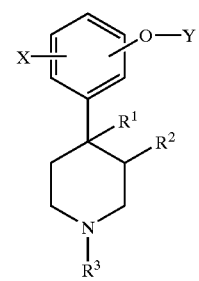

I which comprises reacting a compound of Formula III,

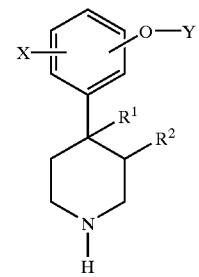

III with a compound of formula VII,

 $R^{3a}$—Z

VII wherein $R^1$ and $R^2$ are each independently H or $C_{1-4}$ alkyl;

$R^3$ is a $C_{1-10}$ alkyl, and which $R^3$ group is substituted at 2-C (relative to the piperidine N-atom) by $SOR^{4d}$, $S(O)_2R^{4d}$, alkanoyl, cycloalkenoyl, alkoxy carbonyl, CN, C(O)—A'—N($R^{5b}$), S(O)—$A^1$ N($R^{5b}$)($R^{5c}$) or $S(O)_2A^1$—N($R^{5b}$)($R^{5c}$);

$R^{3a}$ is a $C_{1-10}$ alkyl group that additionally contains a carbon-carbon double bond α, β to the Z-substituent, wherein said alkyl group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the groups consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and $WA^1$—N($R^{5b}$)($R^{5c}$);

W represents a single bond, CO or $S(O)_p$;

p is 0, 1 or 2;

$A^1$ represents a single bond or $C_{1-10}$ alkylene;

n is 0, 1 or 2;

$R^{4c}$ and $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene which alkylene group is optionally interrupted by O, S, or an $N(R^7)$ group and is optionally substituted by one or more $C_{1-4}$ alkyl groups; $R^7$ is H, $C_{1-6}$ alkyl, $C_{3-8}$ cycloalkyl, $A^2$—($C_{3-8}$ cycloalkyl) or $A^2$ aryl; $A^2$ is $C_{1-6}$ alkylene;

$R^6$ represents $C_{1-6}$ alkyl, $C_{3-8}$ cycloalkyl, $C_{1-4}$ alkylphenyl or aryl, which four groups are optionally substituted by or one or more substituents selected from the group selected from the group consisting of $C_{1-4}$ alkyl, $C_{1-4}$ alkoxy, OH, nitro, amino and halo;

$Het^1$, $Het^2$ and $Het^3$ independently represent 3- to 8-membered heterocyclic groups, which groups contain at least one heteroatom selected from the group consisting of oxygen, sulfur and of nitrogen, which groups are optionally fused to a benzene ring, and which groups are optionally substituted in the heterocyclic and/or fused benzene ring part, by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents one or more substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rOR^{16d}$, $S(O)_rR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl or $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$; to $R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms);

and Z represents $S(O)R^{4d}$, $S(O)_2R^{4d}$, alkanoyl, cycloalkanoyl, alkoxy carbonyl, CN, —C(O)—$A^1$—N($R^{5b}$)($R^{5c}$), —S(O)—$A^1$—N($R^{5b}$)($R^{5c}$), or —$S(O)_2$—$A^1$—N($R^{5b}$)($R^{5c}$).

20. A process for forming a compound of formula

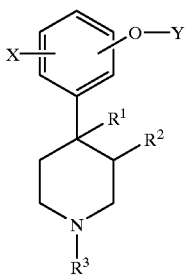

I which comprises reacting a compound of formula XX,

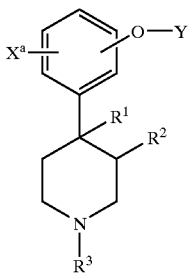

XX with a halogenating agent;
wherein $X^a$ represents one H and optionally one to three of the optional substituents of X;
$R^1$ and $R^2$ are each independently H or $C_{1-4}$ alkyl;
$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$)or $C_{1-10}$ alkyl, wherein said alkyl group is optionally substituted, and/or terminated by one or more substituents selected from $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and $WA^1-N(R^{5b})(R^{5c})$;
n is 0, 1 or 2;
W represents a single bond, C(O) or $S(O)_p$;
$A^1$ represents a single bond or $C_{1-10}$ alkylene;
provided that when both W and $A^1$ represent single bonds, then the group $-N(R^{5b})(R^{5c})$ is not directly attached to an unsaturated carbon atom;
p is 0, 1, or 2;
$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^3$;
provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$,
or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;
$R^6$ represents $C_{1-6}$ alkyl, $C_{3-8}$ cycloalkyl, $C_{1-4}$ amylphenyl or aryl, which four groups are optionally substituted by or one or more substituents selected from the group consisting of $C_{1-4}$ alkyl, $C_{1-4}$ alkoxy, OH, nitro, amino and halo;
$R^7$ represents H, $C_{1-6}$ alkyl, $C_{3-8}$ cycloalkyl, $A^2$ ($C_{3-8}$ cycloalkyl) or $A^2$-aryl;
$A^2$ represents $C_{1-6}$ alkylene;
$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);
Y represents $R^{11}$;
$R^{11}$ represents H;
X represents one or more substituents on the benzene ring, wherein X is halo, and optionally is one or more further subsituents which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rR^{16d}$, $S(O)_t R^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;
$R^{15a}$ to $R^{15c}$ independently represent H, $C_{1-6}$ alkyl or $C_{3-7}$ cycloalkyl (which latter two groups are optionally substituted by one or more halo atoms);
$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;
$R^{17a}$ and $R^{17b}$ independently represent $C_{1-10}$ alkyl, $C_{2-10}$ alkenyl, $C_{2-10}$ alkynyl; $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;
provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7-membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

21. A process for preparing a compound of formula I

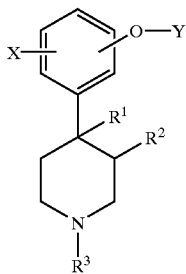

which comprises nitrating a compound of formula XX

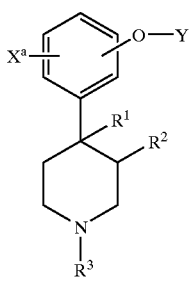

wherein $X^a$ represents one H and optionally one to three of the optional substituents of X;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —$N(R^{4a})(R^{4b})$)or $C_{1-10}$ alkyl, wherein said alkyl, group is optionally substituted and/or terminated or substituted and terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and W—$A^1$—$N(R^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group —$N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo, $R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents nitro and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7-membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

22. A process for preparing a compound of formula I

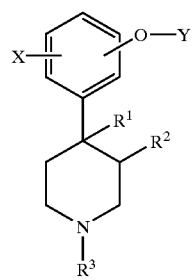

I which comprises sulfonating a compound of formula XX,

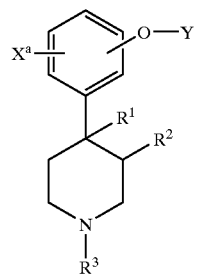

XX wherein $X^a$ represents one H and optionally one to three of the optional substituents of X;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$)or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and $W-A^1-N(R^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group $-N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that R$^{4d}$ does not represent H when n represents 1 or 2;

R$^{5a}$ to R$^{5c}$ each independently represent H, C$_{1-10}$ alkyl C$_{3-10}$ alkenyl, C$_{3-10}$ alkynyl, C$_{3-8}$ cycloalkyl, C$_{1-4}$ alkylphenyl, aryl (which latter six groups are optionally substituted by or one or more substituents selected from the group consisting of OH, nitro, amino, halo, CN, CH$_2$CN, CONH$_2$, C$_{1-4}$ alkyl, C$_{1-4}$ alkoxy and C$_{1-5}$ alkanoyl (which latter three groups are optionally substituted by one or more halo atoms)), or Het$^3$, or R$^{5b}$ and R$^{5c}$ together represent unbranched C$_{2-6}$ alkylene group which alkylene group is optionally interrupted by O, S or NR$^7$ group and optionally substituted by one or more C$_{1-4}$ alkyl groups;

R$^6$ represents C$_{1-6}$ alkyl, C$_{3-8}$ cycloalkyl, C$_{1-4}$ alkylphenyl or aryl, which four groups are optionally substituted by or one or more substituents selected from the group consisting of C$_{1-4}$ alkyl, C$_{1-4}$ alkoxy, OH, nitro, amino and halo;

R$^7$ represents H, C$_{1-6}$ alkyl, C$_{3-8}$ cycloalkyl, A$^2$ (C$_{3-8}$ cycloalkyl) or A$^2$-aryl;

A$^2$ represents C$_{1-6}$ alkylene;

Het$^1$, Het$^2$ and Het$^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group selected from OH, =O, nitro, amino, halo, CN, aryl, C$_{1-4}$ alkyl, C$_{1-4}$ alkoxy and C$_{1-5}$ alkanoyl (which latter three groups are optionally substituted by one or more halo atoms);

Y represents R$^{11}$;

R$^{11}$ represents H;

X represents SO$_2$OH and optionally one or more further substituents on the benzene ring, which substituents are independently selected from the group consisting of halo, CN, nitro, C$_{1-10}$ alkyl, C$_{2-10}$ alkenyl, C$_{2-10}$ alkynyl, C$_{3-7}$ cycloalkyl (which latter four groups are optionally substituted and/or terminated by one or more substituents selected from the group consisting of halo, CN, nitro, OH, C$_{3-7}$ cycloalkyl, C$_{1-6}$ alkoxy, C$_{3-7}$ cycloalkoxy, C$_{1-6}$ alkanoyl, C$_{4-8}$ cycloalkanoyl, C$_{2-6}$ alkoxycarbonyl, C$_{2-6}$ alkanoyloxy and N(R$^{15a}$)(R$^{15b}$)), C(O)R$^{16a}$, C(O)OR$^{16b}$, OC(O)R$^{16c}$, S(O)$_r$OR$^{16d}$, S(O)$_r$R$^{17a}$, OR$^{16e}$, N(R$^{18a}$)(R$^{18b}$), C(O)N(R$^{18c}$)(R$^{18d}$), OC(O)N(R$^{18e}$)(R$^{18f}$), N(R$^{18g}$)C(O)R$^{16f}$, N(R$^{18h}$)C(O)OR$^{19}$, N(R$^{18i}$)C(O)N(R$^{18j}$)(R$^{18k}$), N(R$^{18m}$)S(O)$_2$R$^{17b}$ and B(OR$^{15c}$)$_2$;

R$^{15a}$ to R$^{15c}$ independently represent H, C$_{1-6}$ alkyl or C$_{3-7}$ cycloalkyl (which latter two groups are optionally substituted by one or more halo atoms);

R$^{16a}$ to R$^{16f}$ independently represent H, C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy) or Het$^8$;

R$^{17a}$ and R$^{17b}$ independently represent C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy), Het$^9$ or N(R$^{20a}$)(R$^{20b}$);

provided that R$^{17a}$ does not represent N(R$^{20a}$)(R$^{20b}$) when t is 1;

R$^{18a}$ to R$^{18m}$ independently represent H, C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy), or Het$^{10}$, or R$^{18j}$ and R$^{18k}$ together represent unbranched C$_{3-6}$ alkylene, which alkylene group is optionally interrupted by oxygen, sulfur or an NR$^{20c}$ group;

R$^{19}$ represents C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy) or Het$^{11}$;

R$^{20a}$ to R$^{20c}$ independently represent H, C$_{1-4}$ alkyl or C$_{3-7}$ cycloalkyl (which latter two groups are optionally substituted by one or more halo atoms);

r is 1 or 2;

t is 0, 1 or 2;

Het$^8$ to Het$^{11}$ represent 4- to 7-membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, C$_{1-4}$ alkyl, C$_{1-4}$ alkoxy, C$_{1-6}$ cycloalkyl and C$_{1-5}$ alkanoyl (which latter four groups are optionally substituted by one or more halo atoms).

23. A process for preparing a compound of Formula I

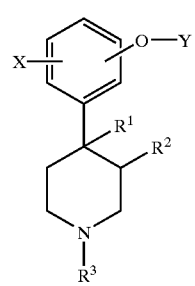

I which comprises sulfenylation of a compound of formula XX

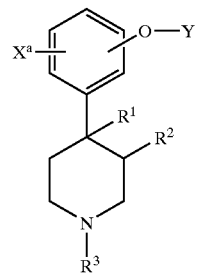

XX wherein

X$^a$ represents one H and optionally one to three of the optional substituents of X;

R$^1$ and R$^2$ are each independently H or C$_{1-4}$ alkyl;

R$^3$ represents aryl (optionally substituted by one or more substituents selected from the group consisting of OH, nitro, halo, CN, CH$_2$CN, CONR$^2$, C$_{1-4}$ alkyl, C$_{1-4}$ alkoxy, C$_{1-5}$ alkanoyl (which latter three groups are optionally substituted by one or more halo atoms) and —N($R^{4a}$)($R^{4b}$))or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, N($R^{5a}$)S(O)$_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and W—$A^1$—N($R^{5b}$)($R^{5c}$);

n is 0, 1 or 2;

W represents a single bond, C(O) or S(O)$_p$;

$A^1$ represents a single bond or $C_{1-10}$ alkylene;

provided that when both W and $A^1$ represent single bonds, then the group —N($R^{5b}$)($R^{5c}$) is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkenyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ tkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy, and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl; which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $S(O)_rR^{17a}$, and optionally one or more further substituents on the benzene ring, which optional substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and N($R^{15a}$)($R^{15b}$)), C(O)$R^{16a}$, C(O)O$R^{16b}$, OC(O)$R^{16c}$, $S(O)_rOR^{16d}$, $S(O)_rR^{17a}$, $OR^{16e}$, N($R^{18a}$)($R^{18b}$), C(O)N($R^{18c}$)($R^{18d}$), OC(O)N($R^{18e}$)($R^{18f}$), N($R^{18g}$)C(O)$R^{16f}$, N($R^{18h}$)C(O)O$R^{19}$, N($R^{18i}$)C(O)N($R^{18j}$)($R^{18k}$), N($R^{18m}$)S(O)$_2R^{17b}$ and B(O$R^{15c}$)$_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ is $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^9$;

$R^{17b}$ is $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or N($R^{20a}$)($R^{20b}$);

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20b}$ independently represent H, $C_{1-4}$ alkyl or $C_{3-7}$ cycloalkyl (which latter two groups are optionally substituted by one or more halo atoms);

r is 1 or 2;

t is 0;

$Het^8$ to $Het^{11}$ represent 4- to 7-membered heterocyclic rings, which rings contain at least one heteroatom selected from the group consisting of oxygen, sulfur and nitrogen, and which rings are optionally substituted by one or more substituents selected from OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

24. A process for preparing a compound of formula I

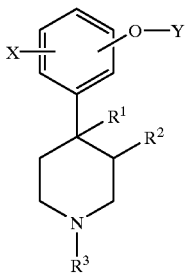

which comprises acylating a compound of Formula XX

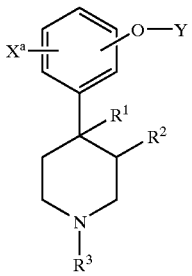

wherein
$X^a$ represents H and optionally one to three of the optional substituents of X;
$R^1$ and $R^2$ are each independently H or $C_{1-4}$ alkyl;
$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{45a})(R^{4b})$)or $C_{1-10}$ alkyl, wherein said alkyl, group is optionally substituted, and/or terminated, by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and $W-A^1-N(R^{5a})(R^{5b})$;
n is 0, 1 or 2;
W represents a single bond, C(O) or $S(O)_p$;
$A^1$ represents a single bond or $C_{1-10}$ alkylene;
provided that when both W and $A^1$ represent single bonds, then the group $-N(R^{5b})(R^{5c})$ is not directly attached to an unsaturated carbon atom;
p is 0, 1 or 2;
$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;
$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$,
or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;
$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;
$R^7$ represents H, $C_{1-6}$ alkyl, $C_{3-8}$ cycloalkyl, $A^2$ ($C_{3-8}$ cycloalkyl) or $A^2$-aryl;
$A^2$ represents $C_{1-6}$ alkylene;
$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);
Y represents $R^{11}$;
$R^{11}$ represents H;
X represents $C(O)R^{16a}$ and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{5b})$), $C(O)R^{16a}$, $C(O)OR^{16b}$, $OC(O)R^{16c}$, $S(O)_tOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;
$R^{15a}$ to $R^{15c}$ independently represent H, $C_{1-6}$ alkyl or $C_{3-7}$ cycloalkyl (which latter two groups are optionally substituted by one or more halo atoms);
$R^{16a}$ is $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;
$R_{16b}$ to $R^{16f}$ independently represent H, $C_{1-10}$ alkyl, $C_{2-10}$ alkenyl, $C_{2-10}$ alkyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;
$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18a}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7-membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

25. A method for preparing a compound of the formula

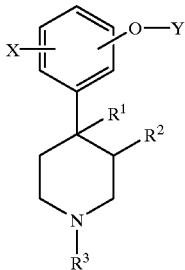

I which comprises reacting a compound of Formula XX

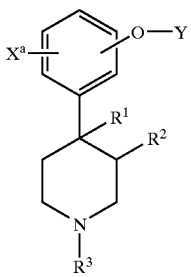

XX with dimethylformamide wherein $X^a$ represents hydrogen and optionally one to three of the optional substituents of X;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —$N(R^{4a})(R^{4b})$) or $C_{1-10}$ alkyl, wherein said alkyl, group is optionally substituted, and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and W—$A^1$—$N(R^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group —$N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents C(O)H and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7-membered heterocyclic rings, which rings contain at least one heteroatom selected from the group consisting of oxygen, sulfur and nitrogen, and which rings are optionally substituted by one or more substituents selected from OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

26. A process for preparing a compound of Formula I

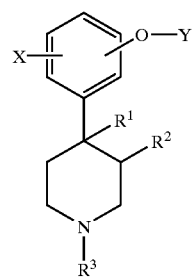

which comprises oxidizing a compound of the formula

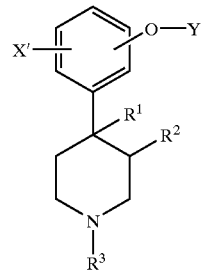

where
X' is $C(O)R^{16a}$ and optionally one or more optional substituents of X;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$)or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and $W-A^1-N(R^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group $-N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ aLkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $OCOR^{16}$ and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_rOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alky, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $NR^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7-membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

27. A process for preparing a compound of Formula I

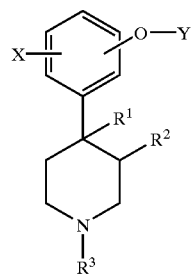

I which comprises subjecting a compound of the Formula

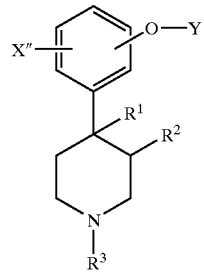

to hydrolysis or reductive cleavage, wherein X" is $OC(O)R^{16c}$;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$) or $C_{1-10}$ alkyl, wherein said alkyl group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, Het$^1$, aryl, adamnantyl (which latter two groups are optionally substituted by one or more substituents selected from the group consisting of OH, nitro, amino, halo, CN, CH$_2$CN, CONH$_2$, $C_{1-4}$ alkyl, $C_{1-4}$ alkoxy and $C_{1-5}$ alkanoyl (which latter three groups are optionally substituted by one or more halo atoms)), and W—A$^1$—N—(R$^{5b}$)(R$^{5c}$);

n is 0, 1 or 2;

W represents a single bond, C(O) or S(O)$_p$;

A$^1$ represents a single bond or $C_{1-10}$ alkylene;

provided that when both W and A$^1$ represent single bonds, then the group —N(R$^{5b}$)(R$^{5c}$) is not directly attached to an unsaturated carbon atom;

p is 0, 1 or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, CH$_2$CN, CONH$_2$, $C_{1-4}$ alkyl, $C_{1-4}$ alkoxy and $C_{1-5}$ alkanoyl (which latter three groups are optionally substituted by one or more halo atoms)) or Het$^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, CH$_2$CN, CONH$_2$, $C_{1-4}$ alkyl, $C_{1-4}$ alkoxy and $C_{1-5}$ alkanoyl (which latter three groups are optionally substituted by one or more halo atoms)), or Het$^3$, or $R^{5b}$ and $R^{5c}$ together represent unbranched $C_{2-6}$ alkylene group which alkylene group is optionally interrupted by O, S or NR$^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, A$^2$ ($C_{3-8}$ cycloalkyl) or A$^2$-aryl;

A$^2$ represents $C_{1-4}$ alkylene;

Het$^1$, Het$^2$ and Het$^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or Biased benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents R$^{11}$;

R$^{11}$ represents H;

X represents OH;

$R^{16c}$ is H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and/or $C_{1-4}$ alkoxy) or Het$^8$;

Het$^8$ represents 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

28. A process for preparing a compound of Formula I

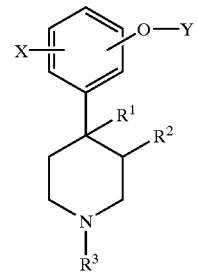

I which comprises reacting a compound of Formula XX

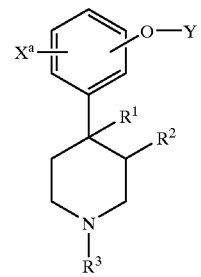

XX with a compound of Formula XXVI $R^{22}$—L$^2$   XXVI under conditions effective to form a compound of Formula I, wherein $R^{22}$ represents $C_{1-10}$ alkyl, $C_{2-10}$ alkenyl, $C_{2-10}$ alkynyl or $C_{3-7}$ cycloalkyl (which four groups are optionally substituted by one or more substituents selected from the group consisting of halo, CN, nitro, OH, $C_{3-7}$ cycloalkyl, $C_{1-6}$ alkoxy, $C_{3-7}$cycloalkoxy, $C_{1-6}$ alkanoyl, $C_{4-8}$ cycloalkanoyl, $C_{2-6}$ alkoxycarbonyl, $C_{2-6}$ alkanoyloxy and N(R$^{15a}$)(R$^{15b}$) and which alkenyl and alkynyl groups when present are fully saturated at 1-C (relative to L$^2$));

L$^2$ represents a leaving group;

X$^a$ represents Hydrogen and optionally one to three of the optional substituents of X;

R$^1$ and R$^2$ are each independently H or $C_{1-4}$ alkyl;

R$^3$ represents aryl (optionally substituted by one or more substituents selected from the group consisting of OH, nitro, halo, CN, CH$_2$CN, CONH$_2$, $C_{1-4}$ alkyl, $C_{1-4}$ alkoxy, $C_{1-5}$ alkanoyl (which latter three groups are optionally substituted by one or more halo atoms) and —N(R$^{4a}$)(R$^{4b}$)) or $C_{1-10}$ alkyl, wherein said alkyl group is optionally substituted and/or terminated by one or more substituents selected from the group consisting of OR$^{4c}$, S(O)$_n$R$^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, N(R$^{5a}$)S(O)$_2$R$^6$, Het$^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and W—$A^1$—N($R^{5b}$)($R^{5c}$);

n is 0, 1 or 2;

W represents a single bond, C(O) or $S(O)_p$;

$A^1$ represents a single bond or $C_{1-10}$ alkylene;

provided that when both W and $A^1$ represent single bonds, then the group —N($R^{5b}$)($R^{5c}$) is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $C_{1-10}$ alkyl, $C_{3-10}$ alkenyl, $C_{3-10}$ alkynyl, $C_{3-7}$ cycloalkyl, (which latter four groups are optionally substituted by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and N($R^{15a}$)($R^{15b}$)), and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated, by one or more substituents selected from the group consisting of halo, CN, nitro, OH, $C_{3-7}$ cycloalkoxy, $C_{1-6}$ alkanoyl, $C_{4-8}$ cycloalkanoyl, $C_{2-6}$ alkanoyloxy and N($R^{15a}$)($R^{16b}$), $C(O)R^{16a}$, $C(O)OR^{16b}$, $OC(O)R^{16c}$, $S(O)_rOR^{16d}$, $S(O)_tR^{17a}$, $OR^{16e}$, N($R^{18a}$)($R^{18b}$), $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$; which alkenyl and alkenyl groups are fully saturated at 1-C relative to the benzene ring;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or N($R^{20a}$)($R^{20b}$);

provided that $R^{17a}$ does not represent N($R^{20a}$)($R^{20b}$) when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

29. A process for preparing a compound of Formula I

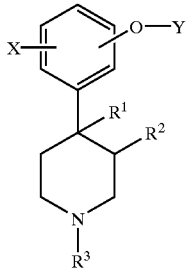

I which comprises performing a rearrangement on a compound of formula XXVII,

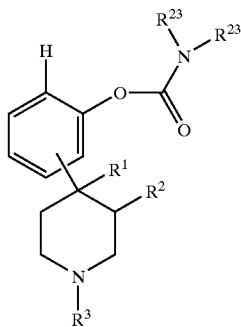

XXVII wherein
$R^{23}$ represents $C_{1-4}$ alkyl or $C_{3-7}$ cycloalkyl,
$R^1$ and $R^2$ are each independently H or $C_{1-4}$ alkyl;
$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —$N(R^{4a})(R^{4b})$) or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and W—$A^1$—N($R^{5b}$)($R^{5c}$);
n is 0, 1 or 2;
W represents a single bond, C(O) or $S(O)_p$;
$A^1$ represents a single bond or $C_{1-10}$ alkylene;
provided that when both W and $A^1$ represent single bonds, then the group —$N(R^{5b})(R^{5c})$ is not directly attached to an unsaturated carbon atom;
p is 0, 1 or 2;
$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;
$R^{11}$ represents H;
X represents one $CON(R^{18c})(R^{18d})$, which group is in the ortho position relative to OY on the phenyl ring, in which $R^{18c}$ and $R^{18d}$ are independently $C_{1-4}$ alkyl or $C_{3-7}$ cycloalkyl.

30. A process for preparing a compound of Formula I

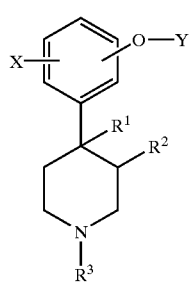

I which comprises reacting a compound of Formula XX

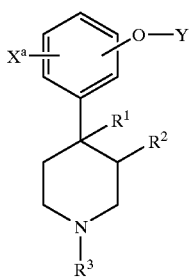

XX with a $C_{2-10}$ aldehyde or $C_{2-10}$ ketone, wherein $X^a$ is hydrogen and optionally one to three of the optional substituents of X, $R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$) or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) and $W-A^1-N(R^{5a})(R^{5b})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group $-N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $C_{2-10}$ alkenyl and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_sOR^{16d}$, $S(O)_tR^{17a}$, $OR^{16e}$, $NR^{18a})(R^{18b})$ $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$, wherein the double bond of the alkenyl chain is α, β to the benzene ring;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20a})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

31. A process for preparing a compound of Formula I

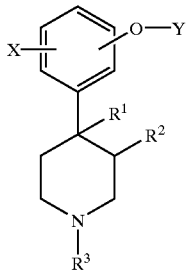

which comprises reacting a compound of Formula XX

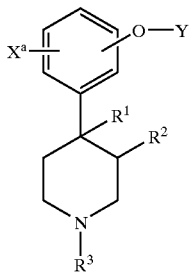

with a compound of formula XXVIII,

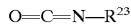   XXVIII wherein $R^{23}$ is $C_{1-4}$ alkyl or $C_{3-7}$ cycloalkyl, $X^a$ is H and optionally one to three of the optional substituents of X;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{4a})(R^{4b})$) or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and $W-A^1-N(R^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group $-N(R^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $CONHR^{18c}$ and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)OR^{16a}$, C(O)OR$^{16b}$, OC(O)R$^{16c}$, S(O)$_r$R$^{16d}$, S(O)$_r$R$^{17a}$, OR$^{16e}$, N(R$^{18a}$)(R$^{18b}$), C(O)N(R$^{18c}$)(R$^{18d}$), OC(O)N(R$^{18e}$)(R$^{18f}$), N(R$^{18g}$)C(O)R$^{16f}$, N(R$^{18h}$)C(O)OR$^{19}$, N(R$^{18i}$)C(O)N(R$^{18j}$)(R$^{18k}$), N(R$^{18m}$)S(O)$_2$R$^{17b}$ and B(OR$^{15c}$)$_2$;

R$^{15a}$ to R$^{15c}$ independently represent H, C$_{1-6}$ alkyl or C$_{3-7}$ cycloalkyl (which latter two groups are optionally substituted by one or more halo atoms);

R$^{16a}$ to R$^{16f}$ independently represent H, C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy) or Het$^8$;

R$^{17a}$ and R$^{17b}$ independently represent C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy), Het$^9$ or N(R$^{20a}$)(R$^{20b}$);

provided that R$^{17a}$ does not represent N(R$^{20a}$)(R$^{20b}$) when t is 1;

R$^{18a}$ R$^{18b}$, R$^{18d}$ to R$^{18m}$ independently represent H, C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy), or Het$^{10}$, or R$^{18j}$ and R$^{18k}$ together represent unbranched C$_{3-6}$ alkylene, which alkylene group is optionally interrupted by oxygen, sulfur or an NR$^{20c}$ group;

R$^{18c}$ is C$_{1-4}$ alkyl or C$_{3-7}$ cycloalkyl;

R$^{19}$ represents C$_{1-10}$ alkyl, C$_{2-10}$ alkenyl, C$_{2-10}$ alkynyl, C$_{3-7}$ cycloalkyl (which latter four groups are optionally substituted by one or more substituents selected from the group consisting of halo, nitro, OH, C$_{1-4}$ alkyl and C$_{1-4}$ alkoxy) or Het$^{11}$;

R$^{20a}$ to R$^{20c}$ independently represent H, C$_{1-4}$ alkyl or C$_{3-7}$ cycloalkyl (which latter two groups are optionally substituted by one or more halo atoms);

r is 1 or 2;

t is 0, 1 or 2;

Het$^8$ to Het$^{11}$ represent 4- to 7-membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, C$_{1-4}$ alkyl, C$_{1-4}$ alkoxy, C$_{1-6}$ cycloalkyl and C$_{1-5}$ alkanoyl (which latter four groups are optionally substituted by one or more halo atoms).

32. A process for preparing a compound of Formula I

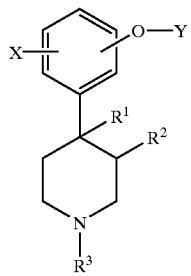

which comprises reacting a compound of Formula XX

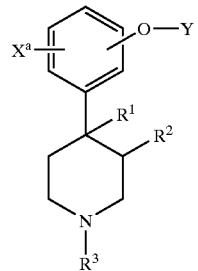

with trimethyl borate wherein X$^a$ represents H and optionally one to three of the optional substituents of X;

R$^1$ and R$^2$ are each independently H or C$_{1-4}$ alkyl;

R$^3$ represents aryl (optionally substituted by one or more substituents selected from the group consisting of OH, nitro, halo, CN, CH$_2$CN, CONH$_2$, C$_{1-4}$ alkyl, C$_{1-4}$ alkoxy, C$_{1-5}$ alkanoyl (which latter three groups are optionally substituted by one or more halo atoms) and —N(R$^{4a}$)($^{4b}$)) or C$_{1-10}$ alkyl, wherein said alkyl, group is optionally substituted and/or terminated by one or more substituents selected from the group consisting of OR$^{4c}$, S(O)$_n$R$^{4d}$, CN, halo, C$_{1-6}$ alkoxy carbonyl, C$_{2-6}$ alkanoyl, C$_{2-6}$ alkanoyloxy, C$_{3-8}$ cycloalkyl, C$_{4-9}$ cycloalkanoyl, N(R$^{5a}$)S(O)$_2$R$^6$, Het$^1$, aryl, adamantyl (which latter two groups are optionally substituted by one or more substituents selected from the group consisting of OH, nitro, amino, halo, CN, CH$_2$CN, CONH$_2$, C$_{1-4}$ alkyl, C$_{1-4}$ alkoxy and C$_{1-5}$ alkanoyl (which latter three groups are optionally substituted by one or more halo atoms)), and W—A$^1$—N(R$^{5a}$)(R$^{5b}$);

n is 0, 1 or 2;

W represents a single bond, C(O) or S(O)$_p$;

A$^1$ represents a single bond or C$_{1-10}$ alkylene;

provided that when both W and A$^1$ represent single bonds, then the group —N(R$^{5b}$)(R$^{5c}$) is not directly attached to an unsaturated carbon atom;

p is 0, 1, or 2;

R$^{4a}$ to R$^{4d}$ each independently represent H, C$_{1-10}$ alkyl, C$_{3-10}$ alkenyl, C$_{3-10}$ alkynyl, C$_{3-8}$ cycloalkyl, C$_{1-4}$ alkylphenyl, aryl (which latter six groups are optionally substituted by or one or more substituents selected from the group consisting of OH, nitro, amino, halo, CN, CH$_2$CN, CONH$_2$, C$_{1-4}$ alkyl, C$_{1-4}$ alkoxy and C$_{1-5}$ alkanoyl (which latter three groups are optionally substituted by one or more halo atoms)) or Het$^2$;

provided that R$^{4d}$ does not represent H when n represents 1 or 2;

R$^{5a}$ to R$^{5c}$ each independently represent H, C$_{1-10}$ alkyl, C$_{3-10}$ alkenyl, C$_{3-10}$ alkyl, C$_{3-8}$ cycloalkyl, C$_{1-4}$ alkylphenyl, aryl (which latter six groups are optionally substituted by or one or more substituents selected from the group consisting of OH, nitro, amino, halo, CN, CH$_2$CN, CONH$_2$, C$_{1-4}$ alkyl, C$_{1-4}$ alkoxy and C$_{1-5}$ alkanoyl (which latter three groups are optionally substituted by one or more halo atoms)), or Het$^3$, or R$^{5b}$ and R$^{5c}$ together represent unbranched C$_{2-6}$ alkylene group which alkylene group is optionally interrupted by O, S or NR$^7$ group and optionally substituted by one or more C$_{1-4}$ alkyl groups;

R$^6$ represents C$_{1-6}$ alkyl, C$_{3-8}$ cycloalkyl, C$_{1-4}$ alkylphenyl or aryl, which four groups are optionally substituted by or one or more substituents selected from the group consisting of $C_{1-4}$ alkyl, $C_{1-4}$ alkoxy, OH, nitro, amino and halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $B(OCH_3)_2$ and optionally one or more further substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting to halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{5b})$), $C(O)R^{16a}$, $C(O)OR^{16b}$, $OC(O)R^{16c}$, $S(O)_rOR^{17a}$, $S(O)_rR^{16d}$, $OR^{16e}$, $N(R^{18a})(R^{18b})$, $C(O)N(R^{18c})(R^{18d})$, $OC(O)N(R^{18e})(RW^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{7b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

33. A process for preparing a compound of Formula I

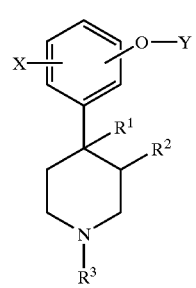

which comprise reacting a compound of the Formula

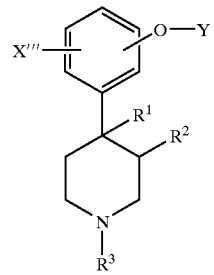

with a compound of formula XXIX $R^{24}$—M                                                         XXIX wherein $R^{24}$ represents $C_{2-10}$ terminal alkenyl or $C_{2-10}$ terminal alkynyl, which alkenyl and alkynyl groups are optionally substituted by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$;

M represents H, a tin-containing moiety, a boron derivative, a zinc halide, a magnesium halide or an alkali metal (which latter three groups may be formed in situ from the corresponding halide);

X''' is halo;

$R^1$ and $R^2$ are each independently H or $C_{1-4}$ alkyl;

$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —$N(R^{4a})(R^{4b})$) or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamnantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and $W—A^1—N(^{5b})(R^{5c})$;

n is 0, 1 or 2;

W represents a single bond, C(O) or $S(O)_p$;

$A^1$ represents a single bond or $C_{1-10}$ alkylene;

provided that when both W and $A^1$ represent single bonds, then the group $—N(^{5b})(R^{5c})$ is not directly attached to an unsaturated carbon atom;

p is 0, 1, or 2;

$R^{4a}$ to $R^{4d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

provided that $R^{4d}$ does not represent H when n represents 1 or 2;

$R^{5a}$ to $R^{5c}$ each independently represent $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$, or $R^{5b}$ and $R^{5c}$ together represent unbranched $C_{2-6}$alkylene group which alkylene group is optionally interrupted by O, S or $NR^7$ group and optionally substituted by one or more $C_{1-4}$ alkyl groups;

$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino or halo;

$R^7$ represents H, $C_{1-6}$ alkyl, $C_{3-8}$ cycloalkyl, $A^2$ ($C_{3-8}$ cycloalkyl) or $A^2$-aryl;

$A^2$ represents $C_{1-6}$ alkylene;

$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

Y represents $R^{11}$;

$R^{11}$ represents H;

X represents $C_{2-10}$ alkenyl or $C_{2-10}$ alkynyl, which alkenyl and alkynyl groups contain a carbon-carbon multiple bond that is α, β to the benzene ring, which alkenyl and alkynyl groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$, and optionally X is further substituted by one or more substituents on the benzene ring, which optional substituents are CN, nitro, $C_{1-10}$ alkyl, $C_{2-10}$ alkenyl, $C_{2-10}$ alkynyl, or $C_{3-7}$ cycloalkyl, (which latter four groups are optionally substituted with CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy or $N(R^{15a})(R^{15b})$), $C(O)R^{16a}$, $C(O)OR^{16b}$, $OC(O)R^{16c}$, $S(O)_rOR^{16d}$, $S(O)_rR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ or $B(OR^{15c})_2$;

$R^{15a}$ to $R^{15c}$ independently represent H, $C_{1-6}$ alkyl or $C_{3-7}$ cycloalkyl (which latter two groups are optionally substituted by one or more halo atoms);

$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;

$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;

provided that $R^{17a}$ does not represent $N(R^{20a})(R^{20b})$ when t is 1;

$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, or 2;

$Het^8$ to $Het^{11}$ represent 4 to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

34. A compound of Formula XX,

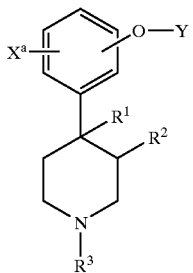

XX wherein
$R^1$ and $R^2$ are each independently H or $C_{1-4}$ alkyl;
$R^3$ represents aryl (optionally substituted by one or more substituents selected from the group consisting of OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —$N(R^{4a})(R^{4b})$) or $C_{1-10}$ alkyl, wherein said alkyl, group is optionally substituted and/or terminated by one or more substituents selected from the group consisting of $OR^{4c}$, $S(O)_nR^{4d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{5a})S(O)_2R^6$, $Het^1$, aryl, adamantyl (which latter two groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), and W—$A^1$—N$(R^{5b})(R^{5c})$;
n is 0, 1 or 2;
W represents a single bond, C(O) or $S(O)_p$;
$A^1$ represents a single bond or $C_{1-10}$ alkylene;
provided that when both W and $A^1$ represent single bonds, then the group —$N(R^{5b})(R^{5c})$ is not directly attached to an unsaturated carbon atom;
p is 0, 1, or 2;
$R^{4a}$ to $R^{4d}$ each independently represent H, $C_{1-10}$ alkyl, $C_{3-10}$ alkenyl, $C_{3-10}$ alkenyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;
provided that $R^{4d}$ does not represent H when n represents 1 or 2;
$R^{5a}$ to $R^{5c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $Het^3$,
or $R^{5b}$ and $R^{5c}$ together represent unbranched $C_{2-6}$ alkylene group which alkylene group is optionally interrupted by O, S or $NR^7$ group and optionally substituted by one or more $C_{1-4}$ alkyl groups;
$R^6$ represents $C_{1-6}$ alkyl, $C_{3-8}$ cycloalkyl, $C_{1-4}$ alkylphenyl or aryl, which four groups are optionally substituted by or one or more substituents selected from the group consisting of $C_{1-4}$ alkyl, $C_{1-4}$ alkoxy, OH, nitro, amino or halo;
$R^7$ represents H, $C_{1-6}$ alkyl, $C_{3-8}$ cycloalkyl, $A^2$ ($C_{3-8}$ cycloalkyl) or $A^2$-aryl;
$A^2$ represents $C_{1-6}$ alkylene;
$Het^1$, $Het^2$ and $Het^3$ independently represent 3- to 8-membered heterocyclic groups, which groups contain at least one heteroatom selected from the group consisting of oxygen, sulfur and nitrogen, which groups are optionally fused to a benzene ring, and which groups are optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);
Y represents $R^{11}$;
$R^{11}$ represents H;
$X^a$ represents H and optionally further represents one to three substituents on the benzene ring, which substituents are independently selected from the group consisting of halo, CN, nitro, $C_{1-10}$ alkyl, $C_{2-10}$ alkenyl, $C_{2-10}$ alkynyl, $C_{3-7}$ cycloalkyl (which latter four groups are optionally substituted and/or terminated by one or more substituents selected from the group consisting of halo, CN, nitro, OH, $C_{3-7}$ cycloalkyl, $C_{1-6}$ alkoxy, $C_{3-7}$ cycloalkoxy, $C_{1-6}$ alkanoyl, $C_{4-8}$ cycloalkanoyl, $C_{2-6}$ alkoxycarbonyl, $C_{2-6}$ alkanoyloxy and $N(R^{15a})(R^{15b})$), $C(O)R^{16a}$, $C(O)OR^{16b}$, $OC(O)R^{16c}$, $S(O)_sOR^{16d}$, $S(O)_tR^{17a}$, $OR^{16e}$, $N(R^{18a})(R^{18b})$, $C(O)N(R^{18c})(R^{18d})$, $OC(O)N(R^{18e})(R^{18f})$, $N(R^{18g})C(O)R^{16f}$, $N(R^{18h})C(O)OR^{19}$, $N(R^{18i})C(O)N(R^{18j})(R^{18k})$, $N(R^{18m})S(O)_2R^{17b}$ and $B(OR^{15c})_2$;
$R^{15a}$ to $R^{15b}$ independently represent H, $C_{1-6}$ alkyl or $C_{3-7}$ cycloalkyl (which latter two groups are optionally substituted by one or more halo atoms);
$R^{16a}$ to $R^{16f}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^8$;
$R^{17a}$ and $R^{17b}$ independently represent $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), $Het^9$ or $N(R^{20a})(R^{20b})$;
provided that $R^{17a}$ does not represent $N(R^{20a})(R^{20b})$ when t is 1;
$R^{18a}$ to $R^{18m}$ independently represent H, $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy), or $Het^{10}$, or $R^{18j}$ and $R^{18k}$ together represent unbranched $C_{3-6}$ alkylene, which alkylene group is optionally interrupted by oxygen, sulfur or an $NR^{20c}$ group;

$R^{19}$ represents $C_{1-10}$ alkyl, $C_{2-10}$ alkenyl, $C_{2-10}$ alkynyl, $C_{3-7}$ cycloalkyl (which latter four groups are optionally substituted by one or more substituents selected from the group consisting of halo, nitro, OH, $C_{1-4}$ alkyl and $C_{1-4}$ alkoxy) or $Het^{11}$;

$R^{20a}$ to $R^{20c}$ independently represent H, $C_{1-4}$ alkyl or $C_{3-7}$ cycloalkyl (which latter two groups are optionally substituted by one or more halo atoms);

r is 1 or 2;

t is 0, 1 or 2;

$Het^8$ to $Het^{11}$ $^1$ represent 4- to 7- membered heterocyclic rings, which rings contain at least one heteroatom selected from the group consisting of oxygen, sulfur and nitrogen, and which rings are optionally substituted by one or more substituents selected from the group consisting of OH, =O, nitro, amino, halo, CN, aryl, $C_{1-4}$ alkyl, $C_{1-4}$ alkoxy, $C_{1-6}$ cycloalkyl and $C_{1-5}$ alkanoyl (which latter four groups are optionally substituted by one or more halo atoms).

* * * * *